(12) United States Patent
Mostafavi et al.

(10) Patent No.: US 10,646,188 B2
(45) Date of Patent: May 12, 2020

(54) METHOD AND SYSTEM FOR RADIATION APPLICATION

(71) Applicant: VARIAN MEDICAL SYSTEMS, INC., Palo Alto, CA (US)

(72) Inventors: Hassan Mostafavi, Los Altos, CA (US); Lisa Ann Hampton, Sunnyvale, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

(21) Appl. No.: 14/246,705

(22) Filed: Apr. 7, 2014

(65) Prior Publication Data
US 2014/0371581 A1    Dec. 18, 2014

Related U.S. Application Data

(60) Division of application No. 10/678,741, filed on Oct. 3, 2003, now Pat. No. 8,788,020, which is a
(Continued)

(51) Int. Cl.
*A61B 5/11*    (2006.01)
*A61B 6/00*    (2006.01)
(Continued)

(52) U.S. Cl.
CPC ............ *A61B 6/541* (2013.01); *A61B 5/0077* (2013.01); *A61B 5/02028* (2013.01);
(Continued)

(58) Field of Classification Search
USPC ........................................ 600/407
See application file for complete search history.

(56) References Cited

U.S. PATENT DOCUMENTS 3,800,125 A * 3/1974 Cleary, Jr. ................ G01S 1/02
342/401
3,861,807 A 1/1975 Lescrenier
(Continued)

FOREIGN PATENT DOCUMENTS

DE    43 41 324 A1    6/1995
DE    19856467    5/2000
(Continued)

OTHER PUBLICATIONS

Adams, W.B. et al. "Correlator Compensation Requirements for Passive Time-Delay Estimation with Moving Source or Receivers" IEEE (Apr. 1980) ASSP-28(2):158-168.
(Continued)

*Primary Examiner* — Patricia J Park
(74) *Attorney, Agent, or Firm* — Vista IP Law Group, LLP

(57) ABSTRACT

A method for generating one or more images includes collecting data samples representative of a motion of an object, acquiring image data of at least a part of the object over a time interval, synchronizing the data samples and the image data to a common time base, and generating one or more images based on the synchronized image data. A method for generating one or more images includes acquiring image data of at least a part of an object over a time interval, associating the image data with one or more phases of a motion cycle, and constructing one or more images using the image data that are associated with the respective one or more phases.

18 Claims, 22 Drawing Sheets

Related U.S. Application Data continuation-in-part of application No. 09/893,122, filed on Jun. 26, 2001, now Pat. No. 6,937,696.

(60) Provisional application No. 60/415,992, filed on Oct. 5, 2002.

(51) Int. Cl.

| | |
|---|---|
| *A61B 5/113* | (2006.01) |
| *A61B 6/03* | (2006.01) |
| *A61B 5/00* | (2006.01) |
| *A61N 5/10* | (2006.01) |
| *A61B 5/02* | (2006.01) |
| *A61B 5/055* | (2006.01) |
| *A61B 90/00* | (2016.01) |

(52) U.S. Cl.
CPC .......... *A61B 5/113* (2013.01); *A61B 5/1128* (2013.01); *A61B 5/7285* (2013.01); *A61B 5/741* (2013.01); *A61B 5/743* (2013.01); *A61B 6/032* (2013.01); *A61B 6/461* (2013.01); *A61B 6/463* (2013.01); *A61B 6/465* (2013.01); *A61B 6/5288* (2013.01); *A61N 5/1049* (2013.01); *A61B 5/0064* (2013.01); *A61B 5/055* (2013.01); *A61B 5/1127* (2013.01); *A61B 5/7289* (2013.01); *A61B 6/4085* (2013.01); *A61B 6/4417* (2013.01); *A61B 90/39* (2016.02); *A61B 2090/371* (2016.02); *A61N 5/1064* (2013.01); *A61N 5/1067* (2013.01); *A61N 2005/1059* (2013.01)

(56) References Cited

U.S. PATENT DOCUMENTS

| | | | |
|---|---|---|---|
| 3,871,360 A | 3/1975 | Van Horn et al. | |
| 3,952,201 A | 4/1976 | Hounsfield | |
| 3,974,386 A | 8/1976 | Mistretta et al. | |
| 4,031,884 A | 6/1977 | Henzel | |
| 4,262,306 A | 4/1981 | Renner | |
| 4,289,142 A | 9/1981 | Kearns | |
| 4,335,427 A | 6/1982 | Hunt et al. | |
| 4,387,722 A | 6/1983 | Kearns | |
| 4,463,425 A | 7/1984 | Hirano et al. | |
| 4,545,384 A | 10/1985 | Kawachi | |
| 4,663,591 A | 5/1987 | Pelc et al. | |
| 4,672,651 A | 6/1987 | Horiba et al. | |
| 4,686,999 A | 8/1987 | Snyder et al. | |
| 4,710,717 A | 12/1987 | Pelc et al. | |
| 4,727,882 A | 3/1988 | Schneider et al. | |
| 4,802,486 A | 2/1989 | Goodman et al. | |
| 4,853,771 A | 8/1989 | Witriol et al. | |
| 4,855,910 A * | 8/1989 | Bohning | 324/309 |
| 4,895,160 A | 1/1990 | Reents | |
| 4,928,692 A | 5/1990 | Goodman et al. | |
| 4,971,065 A | 11/1990 | Pearce | |
| 4,994,965 A * | 2/1991 | Crawford et al. | 378/95 |
| 5,051,903 A | 9/1991 | Pelc et al. | |
| 5,080,100 A | 1/1992 | Trotel | |
| 5,107,845 A | 4/1992 | Guern et al. | |
| 5,109,435 A | 4/1992 | Lo et al. | |
| 5,134,472 A | 7/1992 | Abe | |
| 5,150,426 A | 9/1992 | Bahn et al. | |
| 5,199,424 A | 4/1993 | Sullivan et al. | |
| 5,207,223 A | 5/1993 | Adler et al. | |
| 5,239,591 A | 8/1993 | Ranganath | |
| 5,262,945 A | 11/1993 | DeCarli et al. | |
| 5,265,142 A | 11/1993 | Hsieh | |
| 5,271,055 A * | 12/1993 | Hsieh | A61B 5/1135 378/8 |
| 5,279,309 A | 1/1994 | Taylor et al. | |
| 5,285,786 A | 2/1994 | Fujii | |
| 5,295,483 A | 3/1994 | Nowacki et al. | |
| 5,315,630 A | 5/1994 | Sturm et al. | |
| 5,363,844 A * | 11/1994 | Riederer | G01R 33/5676 600/413 |
| 5,377,681 A | 1/1995 | Drane | |
| 5,389,101 A | 2/1995 | Heilbrun et al. | |
| 5,394,875 A | 3/1995 | Lewis et al. | |
| 5,396,875 A | 3/1995 | Kotwicki et al. | |
| 5,446,548 A | 8/1995 | Gerig et al. | |
| 5,448,548 A | 9/1995 | Taneya et al. | |
| 5,482,042 A | 1/1996 | Fujita | |
| 5,513,646 A | 5/1996 | Lehrman et al. | |
| 5,515,849 A | 5/1996 | Murashita et al. | |
| 5,522,382 A | 6/1996 | Sullivan et al. | |
| 5,531,520 A | 7/1996 | Grimson et al. | |
| 5,535,289 A | 7/1996 | Ito | |
| 5,538,494 A | 7/1996 | Matsuda | |
| 5,549,655 A * | 8/1996 | Erickson | A61N 1/3601 607/42 |
| 5,565,777 A | 10/1996 | Kanayama et al. | |
| 5,573,012 A | 11/1996 | McEwan | |
| 5,582,182 A | 12/1996 | Hillsman | |
| 5,588,430 A | 12/1996 | Bova et al. | |
| 5,603,318 A | 2/1997 | Heilbrun et al. | |
| 5,619,995 A | 4/1997 | Lobodzinski | |
| 5,622,187 A | 4/1997 | Carol | |
| 5,638,819 A | 6/1997 | Manwaring et al. | |
| 5,662,111 A | 9/1997 | Cosman | |
| 5,662,112 A | 9/1997 | Heid | |
| 5,727,554 A * | 3/1998 | Kalend | A61B 6/08 600/407 |
| 5,738,102 A | 4/1998 | Lemelson | |
| 5,764,723 A | 6/1998 | Weinberger et al. | |
| 5,771,310 A | 6/1998 | Vannah | |
| 5,784,431 A | 7/1998 | Kalend et al. | |
| 5,794,621 A | 8/1998 | Hogan et al. | |
| 5,820,553 A | 10/1998 | Hughes | |
| 5,823,192 A | 10/1998 | Kalend et al. | |
| 5,828,770 A | 10/1998 | Leis et al. | |
| 5,836,954 A | 11/1998 | Heilbrun et al. | |
| 5,891,034 A | 4/1999 | Bucholz | |
| 5,906,202 A | 5/1999 | Schuster et al. | |
| 5,912,656 A | 6/1999 | Tham et al. | |
| 5,924,989 A | 7/1999 | Polz | |
| 5,954,647 A | 9/1999 | Bova et al. | |
| 5,982,915 A | 11/1999 | Doi et al. | |
| 5,991,356 A * | 11/1999 | Horiuchi et al. | 378/8 |
| 5,993,390 A | 11/1999 | Savard et al. | |
| 5,993,397 A | 11/1999 | Branson | |
| 5,997,883 A | 12/1999 | Epstein et al. | |
| 6,061,644 A | 5/2000 | Leis | |
| 6,067,373 A | 5/2000 | Ishida et al. | |
| 6,075,557 A | 6/2000 | Holliman et al. | |
| 6,076,005 A * | 6/2000 | Sontag et al. | 600/413 |
| 6,084,939 A | 7/2000 | Tamura | |
| 6,088,488 A * | 7/2000 | Hardy et al. | 382/278 |
| 6,125,166 A | 9/2000 | Takeo | |
| 6,138,302 A | 10/2000 | Sashin et al. | |
| 6,144,874 A | 11/2000 | Du | |
| 6,144,875 A | 11/2000 | Schweikard et al. | |
| 6,146,390 A | 11/2000 | Heilbrun et al. | |
| 6,165,181 A | 12/2000 | Heilbrun et al. | |
| 6,185,445 B1 | 2/2001 | Knuttel | |
| 6,185,446 B1 | 2/2001 | Carlsen, Jr. | |
| 6,198,959 B1 | 3/2001 | Wang | |
| 6,216,029 B1 | 4/2001 | Paltieli | |
| 6,259,943 B1 | 7/2001 | Cosman et al. | |
| 6,266,443 B1 | 7/2001 | Vetro et al. | |
| 6,269,140 B1 | 7/2001 | Takagi et al. | |
| 6,272,368 B1 | 8/2001 | Alexandrescu | |
| 6,296,613 B1 | 10/2001 | Emmenegger et al. | |
| 6,300,974 B1 | 10/2001 | Viala et al. | |
| 6,307,914 B1 | 10/2001 | Kunieda et al. | |
| 6,333,991 B1 | 12/2001 | Schreiber et al. | |
| 6,348,058 B1 | 2/2002 | Melkent et al. | |
| 6,370,217 B1 | 4/2002 | Hu et al. | |
| 6,370,417 B1 | 4/2002 | Horbaschek et al. | |
| 6,375,612 B1 | 4/2002 | Guichon et al. | |
| 6,398,739 B1 | 6/2002 | Sullivan et al. | |
| 6,405,072 B1 * | 6/2002 | Cosman | 600/426 |
| 6,434,215 B1 | 8/2002 | Cesmeli | |

(56) References Cited

U.S. PATENT DOCUMENTS

| | | |
|---|---|---|
| 6,434,507 B1 | 8/2002 | Clayton et al. |
| 6,473,634 B1 | 10/2002 | Barni et al. |
| 6,473,635 B1 | 10/2002 | Rasche |
| 6,475,156 B1 | 11/2002 | Vega |
| 6,486,604 B1 | 11/2002 | Bradatsch |
| 6,487,274 B2 | 11/2002 | Bertsche |
| 6,501,981 B1 | 12/2002 | Schweikard et al. |
| 6,526,117 B1 | 2/2003 | Okerlund et al. |
| 6,526,156 B1 | 2/2003 | Black et al. |
| 6,661,617 B1 | 2/2003 | Hipwell, Jr. et al. |
| 6,527,443 B1 | 3/2003 | Vilsmeier et al. |
| 6,535,574 B1 | 3/2003 | Collins et al. |
| 6,546,124 B1 | 4/2003 | Hopple et al. |
| 6,569,092 B1 | 5/2003 | Guichon et al. |
| 6,611,617 B1 | 8/2003 | Crampton |
| 6,621,889 B1 | 9/2003 | Mostafavi |
| 6,635,021 B1 | 10/2003 | Sullivan et al. |
| 6,665,370 B2 | 12/2003 | Bruder et al. |
| 6,678,399 B2 | 1/2004 | Doi et al. |
| 6,690,965 B1 | 2/2004 | Riaziat et al. |
| 6,697,761 B2 | 2/2004 | Akatsuka et al. |
| 6,705,315 B2 | 3/2004 | Sullivan et al. |
| 6,724,930 B1 | 4/2004 | Kosaka et al. |
| 6,731,970 B2 | 5/2004 | Schlossbauer et al. |
| 6,766,064 B1 | 7/2004 | Langan et al. |
| 6,778,850 B1 | 8/2004 | Adler et al. |
| 6,888,919 B2 | 5/2005 | Graf |
| 6,904,126 B2 | 6/2005 | Endo |
| 6,937,696 B1 | 8/2005 | Mostafavi |
| 6,940,945 B2 | 9/2005 | Maschke |
| 6,980,679 B2 | 12/2005 | Jeung et al. |
| 6,984,208 B2 | 1/2006 | Zheng |
| 7,003,146 B2 | 2/2006 | Eck et al. |
| 7,006,862 B2 | 2/2006 | Kaufman et al. |
| 7,058,204 B2 | 6/2006 | Hildreth et al. |
| 7,062,078 B2 | 6/2006 | Weese et al. |
| 7,103,400 B2 | 9/2006 | Ossmann et al. |
| 7,123,758 B2 | 10/2006 | Jeung et al. |
| 7,158,610 B2 | 1/2007 | Mostafavi |
| 7,221,733 B1 | 5/2007 | Takai et al. |
| 7,227,925 B1 | 6/2007 | Mansfield et al. |
| 7,257,436 B2 | 8/2007 | Sasaki et al. |
| 7,260,426 B2 | 8/2007 | Schweikard et al. |
| 7,306,564 B2 | 12/2007 | Nakatani et al. |
| 7,314,451 B2 | 1/2008 | Halperin et al. |
| 7,349,522 B2 | 3/2008 | Yan et al. |
| 7,403,638 B2 | 7/2008 | Jeung et al. |
| 7,415,169 B2 | 8/2008 | Florent et al. |
| 7,609,810 B2 | 10/2009 | Yi et al. |
| 7,657,301 B2 | 2/2010 | Mate et al. |
| 7,657,302 B2 | 2/2010 | Mate et al. |
| 7,657,303 B2 | 2/2010 | Mate et al. |
| 7,769,430 B2 | 8/2010 | Mostafavi |
| 2001/0002934 A1 | 6/2001 | Oosawa |
| 2002/0023652 A1 | 2/2002 | Riaziat et al. |
| 2002/0091314 A1 | 7/2002 | Schlossbauer et al. |
| 2002/0097155 A1 | 7/2002 | Cassel et al. |
| 2002/0115931 A1 | 8/2002 | Strauss et al. |
| 2002/0118274 A1 | 8/2002 | Yahashi |
| 2002/0188194 A1 | 12/2002 | Cosman |
| 2002/0193685 A1 | 12/2002 | Mate et al. |
| 2003/0007593 A1 | 1/2003 | Heuscher et al. |
| 2003/0007601 A1 | 1/2003 | Jaffray et al. |
| 2003/0026758 A1 | 2/2003 | Baker |
| 2003/0063292 A1 | 4/2003 | Mostafavi |
| 2003/0072419 A1 | 4/2003 | Bruder et al. |
| 2003/0086596 A1 | 5/2003 | Hipp et al. |
| 2003/0099388 A1 | 5/2003 | Doi et al. |
| 2003/0135103 A1 | 7/2003 | Mistretta |
| 2003/0185450 A1 | 10/2003 | Garakani |
| 2003/0188757 A1 | 10/2003 | Yanof et al. |
| 2003/0210812 A1 | 11/2003 | Khamene et al. |
| 2004/0005088 A1 | 1/2004 | Jeung et al. |
| 2004/0068169 A1 | 4/2004 | Mansfield et al. |
| 2004/0071337 A1 | 4/2004 | Jeung et al. |
| 2004/0082853 A1 | 4/2004 | Takeshi et al. |
| 2004/0082874 A1* | 4/2004 | Aoki .............. A61B 5/1135 600/534 |
| 2004/0092815 A1 | 5/2004 | Schweikard et al. |
| 2004/0092816 A1 | 5/2004 | Ossmann et al. |
| 2004/0097805 A1 | 5/2004 | Verard et al. |
| 2004/0114718 A1 | 6/2004 | Brown |
| 2004/0116804 A1 | 6/2004 | Mostafavi |
| 2004/0215077 A1 | 10/2004 | Witt et al. |
| 2004/0218719 A1 | 11/2004 | Brown et al. |
| 2004/0234115 A1 | 11/2004 | Zijp et al. |
| 2004/0254773 A1 | 12/2004 | Zhang et al. |
| 2004/0258307 A1 | 12/2004 | Viola |
| 2005/0002546 A1 | 1/2005 | Florent et al. |
| 2005/0027196 A1 | 2/2005 | Fitzgerald |
| 2005/0053267 A1 | 3/2005 | Mostafavi |
| 2005/0054916 A1 | 3/2005 | Mostafavi |
| 2005/0080336 A1 | 4/2005 | Byrd et al. |
| 2005/0113672 A1 | 5/2005 | Salla et al. |
| 2005/0113711 A1 | 5/2005 | Nakatani et al. |
| 2005/0201510 A1 | 9/2005 | Mostafavi |
| 2005/0283068 A1 | 12/2005 | Zuccolotto et al. |
| 2006/0165267 A1 | 7/2006 | Wyman et al. |
| 2006/0241443 A1 | 10/2006 | Whitmore et al. |
| 2007/0053491 A1 | 3/2007 | Schildkraut et al. |
| 2007/0053494 A1 | 3/2007 | Mostafavi |
| 2007/0189455 A1 | 8/2007 | Allison |
| 2008/0144772 A1 | 6/2008 | Yi et al. |

FOREIGN PATENT DOCUMENTS

| | | |
|---|---|---|
| EP | 0866607 | 9/1998 |
| EP | 1 050 272 A | 11/2000 |
| FI | 79458 | 9/1989 |
| JP | 58-136334 | 8/1983 |
| JP | 61-220628 | 9/1986 |
| JP | 4-364677 | 12/1992 |
| JP | 6-292085 | 10/1994 |
| JP | 7-275237 | 10/1995 |
| JP | 10-289321 | 10/1998 |
| JP | 2000-262511 | 9/2000 |
| JP | 2000-325339 | 11/2000 |
| JP | 2002-090118 | 3/2002 |
| JP | 2002-533889 | 10/2002 |
| JP | 5296315 | 9/2013 |
| WO | WO 98/16151 | 4/1998 |
| WO | WO 98/30977 | 7/1998 |
| WO | WO 98/38908 | 9/1998 |
| WO | WO 98/52635 | 11/1998 |
| WO | WO 00/24333 | 5/2000 |
| WO | WO 00/24466 | 5/2000 |
| WO | WO 00/77818 | 12/2000 |
| WO | WO 02/26125 | 4/2002 |
| WO | WO 02/085455 | 10/2002 |
| WO | WO 03/003796 | 1/2003 |

OTHER PUBLICATIONS

Ahlstrom, K.H. et al. "Pulmonary MR Angiography with Ultrasmall Superparamagnitic Iron Oxide Particles as a Blood Pool Agent and a Navigtor Echo for Respiratory Gating: Pilot Study" Radiology (Jun. 1999) 211(3):865-869.

Axel, L. et al. "Respiratory Effects in Two-Dimensional Fourier Transform MR Imaging" Radiology (Sep. 1986) 160(3):795-801.

Balter, J.M. et al.; "Uncertainties in CT-Based Radiation Therapy Treatment Planning Associated With Patient Breathing"; Int. J. Radial. Oncol.. Bioi., Phys. 36; pp. 167-174 (Aug. 1996).

Bankman, I.N. et al. "Optimal Detection, Classification, and Superposition Resolution in Neural Waveform Recordings" IEEE ) Aug. 1993) 40(8):836-841).

Baroni, G. and G. Ferrigno "Real-time Motion Analysis for Definition and Control of Patient Position in Radiotherapy" SPIE 0-81942084-0/96 2709:506-515.

Bellenger, N.G. et al.; "Left Ventricular Quantification in Heart Failure by Cardiovascular MR Using Prospective OS Respiratory Navigator Gating: Comparison With Breath-Hold Acquisition"; J. Magn. Reson. Imaging 11; pp. 411-417; (Apr. 2000).

(56) References Cited

OTHER PUBLICATIONS

Cho, K. et al.; "Development of Respiratory Gated Myocardial SPECT System", J. Nucl. Cardial. 6; pp. 20-28; (Jan. 1, Feb. 1999).
Danias, P.G. et al. "Prospective Navigator Correction of Image Position for Coronary MR Angiography" Radiology (Jun. 1997) 203:733-736.
Davies, S.C. et al.; "Ultrasound Quantitation of Respiratory Organ Motion in the Upper Abdomen"; Br. J. Radiol. 67; pp. 1096-1102 (Nov. 1994).
Du, Y.P. "Prospective navigator gating with a dual acceptance window technique to reduce respiratory motion artifacts in 3D MR coronary angiography" Int'l J. Cardiovascular Imaging (2003) 19:157-162.
Du, Y.P. et al. "A comparison of prospective and retrospective respiratory navigator gating in 3D MR coronary angiography" Int'l J. Cardiovascular Imaging (2001) 17:287-294.
Ehman, R.L. et al.; "Magnetic Resonance Imaging With Respiratory Gating: Techniques and Advantages"; Am. J. Roenlgenol143; pp. 1175-1182 (Dec. 1984).
Fee, M.S. et al. "Automatic Sorting of Mulitple Unit Neuronal Signals in the Presence of Anisotropic and non-Gaussian Variability" J. Neuroscience Methods (1996) 69:175-188.
Felblinger, J. et al. "Effects of physiologic motion of the human brain upon quantitative H-MRS: analysis and correction by retrogating" NMR in Biomedicine (1998) 11:107-114.
Fishbein, K.W. et al. "The lever-coil: A simple, inexpensive sensor for respiratory and cardiac motion in MRI experiments" Magnetic Resonance Imaging (2001) 19:881-889.
Frolich, H.et al.;"A Simple Device for Breath-Level Monitoring During CT"; Radiology 156; p. 235 (Jul. 1985).
Gerig, L.H. et al. "The Development and Clinical Application of a Patient Position Monitoring System" Ottawa Regional Cancer Centre, General Division, 501 Smyth Rd., Ottawa, Ontario, Canada K1H8L6; National Research Council, IIT, Ottawa, Ontario, Canada K1A OR6; SpIE Videometrics III (1994) 2350:59-72.
Haacke, E.M. and G.W. Lenz "Improving MR Image Quality in the Presence of Motion by Using Rephasing Gradients" AJR (Jun. 1987) 148:1251-1258.
Hanley, J. et al.; "Deep Inspiration Breath-Hold Technique for Lung Tumors: The Potential Value of Target CS Immobilization and Reduced Lung Density in Dose Escalation"; Int. J. Radial. Oncol., Biol. Phys. 45; pp. 603-611 (Oct. 1999).
Henkelman, R.M. et al.; "How Important Is Breathing in Radiation Therapy of the Thorax?"; Int. J. Radiat. Onco/., Bioi., Phys. 8; pp. 2005-2010 (Nov. 1982).
Hofman, M.B.M. et al.; "MRI of Coronary Arteries: 20 Breath-Hold vs. 3D Respiratory-Gated Acquisition"; J. of Compo Assisted Tomography 19; pp. 56-62 (Jan.1, Feb. 1995).
Huber, A. et al. "Navigator Echo-Based Respiratory Gating for Three-Dimensional MR Coronary Angiography: Results from Healthy Volunteers and Patients with Proximal Coronary Artery Stenoses" AJR (Jul. 1999) 173:95-101.
Iwasawa, Tae, et al.; "Normal In-Plane Respiratory Motion of the Bilateral Hemidiaphragms Evaluated by Sequentially Subtracted Fast Magnetic Resonance Images"; Journal of Thoracic Imaging; 1999; vol. 14, No. 2; pp. 130-134.
Johnson, L.S. et al.; "Initial Clinical Experience With a Video-Based Patient Positioning System"; Int. J. Radial. Oncol. BioI. Phys. 45; pp. 205-213; (Aug. 1999).
Jolesz, Ferenc M.D., et al.; "Image-Guided Procedures and the Operating Room of the Future"; Radiology; SPL Technical Report #48; May 1997: 204:601-612.
Josefsson, T. et al. "A Flexible High-Precision Video System for Digital Recording of Motor Acts Through Lightweight Reflex Markers" Computer Methods & Programs in Biomedicine (1996) 49:119-129.
Kachelriess, Marc, et al.; "Electrocardiogram-correlated Image Reconstruction From Subsecond Spiral Computed Tomography Scans of the Heart"; Med. Phys. 25(12); Dec. 1998; pp. 2417-2431.
Keatley, E. et al.; "Computer Automated Diaphragm Motion Quantification in a Fluoroscopic Movie"; Dept. of Medical Physics, Memorial Sloan-Kettering Cancer Center, New York; 3 pp. 1749-1751.
Kim, W.S., et al.; "Extension of Cardiac and Respiratory Motion Cycles by Use of Projection Data and Its Applications to NMR Imaging"; Magnetic Resonance in Medicine 13; 1990; pp. 25-37.
Korin, H.W. et al.; "Respiratory Kinematics of the Upper Abdominal Organs: A Quantitative Study"; Magn. Rason. Med. 23; pp. 172-178 (Jan. 1992).
Kubo, H.D. et al.; "Breathing-Synchronized Radiotherapy Program at the University of California Davis Cancer Center"; Med. Phys. 27(2); Feb. 2000; pp. 346-353.
Kubo, H.D. et al.; "Compatibility of Varian 2100C Gated Operations With Enhanced Dynamic Wedge and IMRT Dose Delivery"; Med. Phys. 27; pp. 1732-1738; (Aug. 2000).
Kubo, H.D. et al.; "Potential and Role of a Prototype Amorphous Silicon Array Electronic Portal Imaging Device in Breathing Synchronized Radiotherapy"; Med. Phys. 26(11); Nov. 1999; pp. 2410-2414.
Kubo, H.D. et al.; "Respiration Gated Radiotherapy Treatment: A Technical Study"; Phys. Mad. Bioi. 41; pp. 83-91;(1996).
Kutcher, G.J. et al.; "Control; Correction, and Modeling of Setup Errors and Organ Motion", Semin. Radiat. Oncol. 5; pp. 134-145 (Apr. 1995).
Lee, M.W. and I. Cohen "Human Body Tracking with Auxiliary Measurements" IEEE International Workshop on Analysis and Modeling of Faces and Gestures (2003) 8 pages, located at htt/://iris.usc.edu/~icohen/projects/human/body/index.htm.
Lethimonnier, F. et al.; "Three-Dimensional. Coronary Artery MR Imaging Using Prospective Real-Time Respiratory DE Navigator and Linear Phase Shift Processing: Comparison With Conventional Coronary Angiography", Magn. Reson. Imaaine 17; DO. 1111-1120; (1999).
Lewis, C.E. et al.; "Comparison of Respiratory Triggering and Gating Techniques for the Removal of Respiratory Artifacts in MR Imaging"; Radiology 160; pp. 803-810; (Sep. 1986).
Li, D. et al.; "Coronary Arteries: Three-dimensional MR Imaging With Retrospective Respiratory Gating"; Radiology; Dec. 1996; vol. 201; No. 3.; pp. 857-863.
Lieberman, J.M. et al. Gated Magnetic Resonance Imaging of the Normal Diseased Heart: Radiology (Aug. 1984) 152:465-470.
Lopresti, B.J. et al. "Implementation and Performance of an Optical Motion Tracking System for High Resolution Brain PET Imaging" IEEE Transactions on Nuclear Science (Dec. 1999) 46(6):2059-2067.
Luker, Gary D., et al.; "Ghosting of Pulmonary Nodules With Respiratory Motion: Comparison of Helical and ConvenHonal CT Using an In Vitro Pediatric Model"; AJR:167; Nov. 1996; pp. 1189-1193.
Mageras, G. et al.; "Initial Clinical Evaluation of a Respiratory Gating Radiotherapy System"; 22nd Annual EMBS International Conference, Chicago. IL.; pp. 2124-2127; (Jul. 23-28, 2000).
Mageras, G.S. et al.; "Respiratory Motion-Induced Treatment Uncertainties"; Patras Medical Physics 99- VI International Conference on Medical Physics, Monduzzi Editore; pp. 33-39; (Sep. 1999).
Mageras, G.S., "Interventional Strategies for Reducing Respiratory-Induced Motion in External Beam Therapy"; The Use of Computers in Radiation Therapy Xlllth International Conference, Heidelberg, Germany; pp. 514-516; (May 2000).
Mah, D. et al.; "Technical Aspects of the Deep Inspiration Breath Hold Technique in the Treatment of Thoracic Cancer"; Int. J. Radiat. Oncol., Bioi., Phys. 48; pp. 1175-1185; (Nov. 2000).
Mah, K. et al.; "Time Varying Dose Due to Respiratory Motion During Radiation Therapy of the Thorax"; Proceedings of the Eighth Inl'1 Conference on the Use of Computers in Radiation Therapy, Toronto, Canada; Jul. 9-12, 1984; 00. 294-298.
Malone, S. et al.; "Respiratory-Induced Prostate Motion: Quantification and Characterization", Int. J. Radial. Oneal., Bioi., Phys. 48; pp. 105-109; (Aug. 2000).

(56) References Cited

OTHER PUBLICATIONS

Manke, D. et al. "Model Evaluation and Calibration for Prospective Respiratory Motion Correction in Coronary MR Angiography Based on 3-D Image Registration" IEEE Transactions on Medical Imaging (Sep. 2002) 21(9):1132-1141.
Manke, D. et al. "Respiratory Motion in Coronary Magnetic Resonance Angiography: A Comparison of Different Motion Models" J. Magnetic Resonance Imaging (2002) 15:661-671.
McConnell, M.V. et al. "Comparison of Respiratory Suppression Methods and Navigator Locations for MR Coronary Angiography" AJR (May 1997) 168:1369-1375.
McConnell, M.V. et al. "Prospective Adaptive Navigator Correction for Breath-Hold MR Coronary Angiography" MRM (1997) 37:148-152.
Moerland, M.A. et al.; "The Influence of Respiration Induced Motion of the Kidneys on the Accuracy of CZ Radiotherapy Treatment Planning, A Magnetic Resonance Imaging Study", Radiotherapy Oncol. 30, pp. 150-154 (1994).
Mori, M. et al.; "Accurate Contiguous Sections Without Breath-Holding on Chest CT; Value of Respiratory Gating and Ultrafast CT"; AJR:162. May 1994; pp. 1057-1062.
Mostafavi, H.; "Method and System for Radiation Application"; U.S. Appl. No. 10/678,741, filed Oct. 3, 2003; Specification 63 pgs.; Claims 9 pgs; Abstract 1 pg; Drawings 22 pgs.
Mostafavi, Hassan; "Overview of Post-Processing Algorithm to Create Volumetric Motion Sequences"; Varian Medical Systems, Inc.; May 2. 2002; 1 page.
Nevatia, R. et. al. "Human Body Tracking with Articulated Human Body Model" (Nov. 2002) pp. 1-3.
Nikolaou, K. et al. "Navigator Echo-Based Respiratory Gating for Three-Dimensional MR Coronary Angiography: Reduction of Scan Time Using a Slice Interpolation Technique" J. Computer Assisted Tomography (2001) 25(3):378-387.
Ohara, K. et al.; "Irradiation Synchronized With Respiration Gate"; Int. J. Radial. Oncol.; BioI. Phys. 17; pp. 853- 857; (Oct. 1989).
Oshinski, J.N. et al.; "Two-Dimensional Coronary MR Angiography Without Breath Holding"; Radiology 201; pp. 737-743; (Dec. 1996).
Paradis, A.L. et al. "Detection of Periodic Signals in Brain Echo-Planar Functional Images" IEEE (Jan. 1, 1997) pp. 696-697.
Peltola, Seppo M.Sc.; "Gated Radiotherapy to Compensate for Patient Breathing"; Proceedings of the Eleventh Varian Users Meeting; Macro Island, Florida; May 11.13, 1986; 4 pages.
Plein, S. et al. "Three-Dimensional Coronary MR Angiography Performed with Subject-Specific Cardiac Acquisition Windows and Motion-Adapted Respiratory Gating" AJR (Feb. 2003) 180:505-512.
Post, J.C. et al. "Three-Dimensional Respiratory-Gated MR Angiography of Coronary Arteries: Comparison with Conventional Coronary Angiography" AJR (Jun. 1996) 166:1399-1404.
Ramsey, C.R. et al.; "Clinical Efficacy of Respiratory Gated Conformal Radiation Therapy", Medical Dosimetry 24; pp. 115-119: (1999).
Ramsey, C.R. et al.;"A Comparison of Beam Characteristics for Gated and Nongated Clinical X-Ray Beams"; Med. Phys. 26; pp. 2086-2091; (Oct. 1999).
Regenfus, M. et al. "Comparison of Contrast-Enhanced Breath-Hold and Free-Breathing Respiratory-Gated Imaging in Three-dimensional Magnetic Resonance Coronary Angiography" Am. J. Cardiology (Oct. 1, 2002) 90:725-730.
Ritchie, C. J., et al.; "Predictive Respiratory Gating: A New Method to Reduce Motion Artifacts on CT Scans"; Radiology; 1994; pp. 847-852; vol. 190; No. 3.
Robinson, Terry E., et al.; "Standardized High-Resolution CT of the Lung Using a Spirometer-Triggered Electron Beam CT Scanner"; AJR:172; Jun. 1999; pp. 1636-1638.
Rogus, R.D. et al.; "Accuracy of a Photogrammetry-Based Patient Positioning and Monitoring System for Radiation Therapy"; Med. Phys. 26; pp. 721-728; (May 1999).

Rosenzweig, K.E. et al.; The Deep Inspiration Breath Hold Technique in the Treatment of Inoperable Non-Small-Cell Lung Cancer; Inl. J. Radiat. Oncol., BioI.. Phys. 48; pp. 81-87; (Aug. 2000).
Ross, C.S. et al.; "Analysis of Movement of Intrathoracic Neoplasms Using Ultrafast Computerized Tomography"; Int. J. Radia/. Oncol., Bioi., Phys. 18; pp. 671-677; (Mar. 1990).
Runge, V.M. et al.; "Respiratory Gating in Magnetic Resonance Imaging at 0.5 Tesla"; Radiology 151; pp. 521-523; (May 1984).
Sachs, T.S. et al.; "Real-Time Motion Detection in Spiral MRI Using Navigators", Magn. Reson. Med. 32; pp. 639-645; (Nov. 1994).
Schar, M. et al. "The Impact of Spatial Resolution and Respiratory Motion on MR Imaging of Atherosclerotic Plaque" J. Magnetic Resonance Imaging (2003) 17:538-544.
Schwartz, L.H. et al.; "Kidney Mobility During Respiration"; Radio/her. Oncol. 32; pp. 84-86; (1994).
Shirato, H. et al.; "Four-Dimensional Treatment Planning and Fluroscopic Real-Time Tumor Tracking Radiotherapy for Moving Rumor"; Int. J. Radial. Oncol., Bioi., Phys. 48; pp. 435-442; (Sep. 2000).
Sinkus, Ralph. et al.; "Motion Pattern Adapted Real-Time Respiratory Gating"; Magnetic Resonance in Medicine 41; 1999; pp. 148-155.
Solberg, Timothy D., et al.; "Feasibility of Gated IMRT"; Proceedings of the 22nd Annual International Conference of the IEEE Engineering in Medicine and Biology Society, Chicago, IL (Jul. 23-28, 2000) 3pps: 2732-2734.
Spuentrup, E. et al. "Respiratory motion artifact suppression in diffusion-weighted MR imaging of the spine" Eur. Radiol. (2003) 13:330-336.
Suramo, M.P. et al.; "Cranio-caudal Movements of the Liver, Pancreas and Kidneys on Respiration", Acta Radiol. Diagn. 2; pp. 129-131; (1984).
Tada, Takuhito, et al.; "Lung Cancer: Intermittent Irradiation Synchronized With Respiratory Motion-Results of a Pilot Study"; Radiology, Jun. 1998; vol. 207; No. 3; pp. 779-783.
Thickman, D. et al. "Phase-Encoding Direction upon Magnetic Resonance Image Quality of the Heart" Magnetic Resonance in Medicine (1988) 6:390-396.
Van Geuns, R.J.M. et al.; "Magnetic Resonance Imaging of the Coronary Arteries: Clinical Results From ThreeDimensional Evaluation of a Respiratory Gated Technique"; Heart 82; pp. 515-519; (Oct. 1999).
Wang, Y. et al. "Navigator-Echo-based Real-Time Respiratory Gating and Triggering for Reduction of Respiration Effects in Three-dimensional Crornary MR Angiography" Radiology (1996) 198:55-60.
Wang, Y. et al. "Respiratory Motion of the Heart: Kinematics and the Implication for the Spatial Resolution in Coronary Imaging" Magnetic Resonance in Medicine (1995) 33:713-719.
Wang, Y. et al.; "Implications for the Spatial Resolution in Coronary Imaging"; Magnetic Resonance in Medicine 33; 1995; pp. 713-719.
Weber, C. et al. "Correlation of 3D MR coronary angiography with selective coronary angiography: feasibilitly of the motion adapted gating technique" Eur. Radiol. (2002) 12:718-726.
Weiger, Markus, et al.; "Motion-Adapted Gating Based on k-Space Weighting for Reduction of Respiratory Motion Artifacts"; Magnetic Resonance in Medicine 38; 1997; pp. 322-333.
Wiesmann, F. "High-Resoulution MRI with Cardiac and Respiratory Gating Allows for Accurate in Vivo Atherosclerotic Plaque Visualization in the Muring Aortic Arch" Magnetic Resonance in Medicine (2003) 50:69-74.
Wong, J.W. et al.; "The Use of Active Breathing Control (ABC) to Reduce Margin for Breathing Motion"; In/. J.Radial. Oncol., Phys. 44; pp. 911-919; (Jul. 1999).
Wood, M. L. and R. M. Henkelman "Suppression of respiratory motion artifacts in magnetic resonance imaging" Med. Phys. (Nov./Dec. 1996) 13(6):794-805.
Woodard, P.K., et al.; "Detection of Coronary Stenoses on Source and Projection Images Using Three-Dimensional MR Angiography With Retrospective Respiratory Gating: Preliminary Experience"; AJR:170; Apr. 1998; No. 4; 00. 883-888.

(56) References Cited

OTHER PUBLICATIONS

Worthley, S.G. et al. "Cardiac gated breath-hold back blood MRI of the coronary artery wall: An in vivo and ex-vivo comparison" Int'l J. Cardiovascular Imaging (2001) 17:195-201.
Yamashita, Y. et al. "MR Imaging of Focal Lung Lesions: Elimination of Flow and Motion Artifact by Breath-Hold ECG-Gated and Black-Blood Techniques on T2-Weighted Turbo SE and STIR Swquences" J. Magnetic Resonance Imaging (1999) 9:691-698.
Yorke, E. et al.; "Respiratory Gating of Sliding Window IMRT"; 22nd Annual EMBS International Conference. Chicago, IL.; pp. 2118-2121; (Jul. 23-28. 2000).
Yorke, Ellen. et al.; "Respiratory Gating of Sliding Window IMRT"; Dept. of Medical Physics, Memorial Sloan-Kettering Cancer Center, New York; 4 pps.
Yuan, Q. et al.; "Cardiac-Respiratory Gating Method for Magnetic Resonance Imaging of the Heart"; Magn. Reson. Med. 43; pp. 314-318; (Feb. 2000).
Vedam, S.S. et al., "Acquiring a four-dimensional computed tomography dataset using an external respiratory signal" Phys. Med. Bio. 48 (2003), pp. 45-62.
Adler Jr. et al., "Image-Guided Robotic Radiosurgery". Neurosurgery, vol. 44, No. 6, Jun. 1999.
Murphy et al., "Patterns of Patient Movement During Frameless Image-Guided Radiosurgery". International Journal of Radiation Oncology Biology Physics, vol. 55, No. 5, Apr. 1, 2003.
Neicu et al., "Synchronized Moving Aperture Radiation Therapy (SMART): Average Tumour Trajectory for Lung Patients". Physics in Medicine and Biology, vol. 48, No. 5, Mar. 7, 2003.
Bifulco p. et al., "Automatic Recognition of Vertebral Landmarks in Fluoroscopic Sequences for Analysis of Intervertebral Kinematics", Medical and Biological Engineering and Computing, Springer, Heildelberg, DE, vol. 39, No. 1, Jan. 1, 2011, 12 pages.
Eisner R L et al., "Use of Cross-Correlation Function to Detect Patient Motion During Spect Imaging", Journal of Nuclear Medicine, Society of Nuclear Medicine, Reston, VA, US, vol. 28, No. 1, Jan. 1, 1987, 6 pages.
European Supplementary Search Report for EP Application No. 04793980.6 dated Mar. 12, 2009.
European Supplementary Search Report for EP Application No. 04783114.4 dated Dec. 30, 2010.
International Search Report and Written Opinion dated Feb. 5, 2007 for PCT/US2005/034999.
International Search Report and Written Opinion dated Dec. 1, 2005 (PCT/US05/08037).
International Search Report and Written Opinion dated Oct. 13, 2005 (PCT/US04/32381).
International Search Report, Varian Medical Systems, Inc. PCT/US03/27552, dated Feb. 19, 2004.
Preliminary Search Brochure entitled "Kinematic Measurement Systems" by Qualisys printed Apr. 4, 1994; 4 pages.
International Search Report for PCT/US03/36454 dated May 28, 2004.
International Search Report and Written Opinion dated Feb. 15, 2005 for PCT/US2004/029277.
International Search Report and Written Opinion dated Jan. 30, 2006 for PCT/US2004/028571.
International Search Report and Written Opinion dated Mar. 15, 2005 for PCT/US2004/028756.
Non Final Office Action dated Aug. 4, 2009 for U.S. Appl. No. 10/678,741.
Non Final Office Action dated Aug. 19, 2008 for U.S. Appl. No. 10/678,741.
Non Final Office Action dated Jan. 16, 2008 for U.S. Appl. No. 10/678,741.
Final Office Action dated Feb. 17, 2009 for U.S. Appl. No. 10/678,741.
Non Final Office Action dated Jul. 7, 2010 for U.S. Appl. No. 10/678,741.
Non Final Office Action dated Aug. 21, 2009 for U.S. Appl. No. 11/116,699.
Non Final Office Action dated Mar. 4, 2010 for U.S. Appl. No. 11/116,699.
Non Final Office Action dated Apr. 3, 2009 for U.S. Appl. No. 12/182,932.
Final Office Action dated Nov. 3, 2009 for U.S. Appl. No. 12/182,932.
Non Final Office Action dated Nov. 2, 2009 for U.S. Appl. No. 10/655,920.
Non Final Office Action dated Oct. 28, 2008 for U.S. Appl. No. 10/655,920.
Non Final Office Action dated Oct. 18, 2007 for U.S. Appl. No. 10/655,920.
Non Final Office Action dated Jan. 30, 2007 for U.S. Appl. No. 10/655,920.
Final Office Action dated May 8, 2009 for U.S. Appl. No. 10/655,920.
Final Office Action dated Apr. 29, 2008 for U.S. Appl. No. 10/655,920.
Final Office Action dated May 20, 2010 for U.S. Appl. No. 10/655,920.
Non Final Office Action dated Jun. 11, 2012 for U.S. Appl. No. 10/655,920.
Non Final Office Action dated Nov. 21, 2008 for U.S. Appl. No. 10/656,478.
Non Final Office Action dated May 20, 2008 for U.S. Appl. No. 10/656,478.
Non Final Office Action dated Jun. 13, 2007 for U.S. Appl. No. 10/656,478.
Non Final Office Action dated Dec. 13, 2006 for U.S. Appl. No. 10/656,478.
Non Final Office Action dated Jan. 26, 2010 for U.S. Appl. No. 10/656,478.
Final Office Action dated May 5, 2009 for U.S. Appl. No. 10/656,478.
Final Office Action dated Nov. 5, 2007 for U.S. Appl. No. 10/656,478.
Final Office Action dated Aug. 5, 2010 for U.S. Appl. No. 10/656,478.
Non-Final Office Action dated Sep. 14, 2010 for U.S. Appl. No. 11/116,699.
Non-Final Office Action dated Nov. 9, 2010 for U.S. Appl. No. 10/655,920.
Final Office Action dated Dec. 8, 2010 for U.S. Appl. No. 10/678,741.
Final Office Action dated Feb. 28, 2011 for U.S. Appl. No. 11/116,699.
Final Office Action dated Apr. 26, 2011 for U.S. Appl. No. 10/655,920.
Non-Final Office Action dated Aug. 12, 2011 for U.S. Appl. No. 12/182,932.
Non-Final Office Action dated Jul. 20, 2011 for U.S. Appl. No. 10/678,741.
Non-Final Office Action dated Oct. 24, 2011 for U.S. Appl. No. 12/205,512.
Final Office Action dated Dec. 16, 2011 for U.S. Appl. No. 12/182,932.
Final Office Action dated Jan. 27, 2012 for U.S. Appl. No. 10/678,741.
Non-Final Office Action dated Apr. 17, 2012 for U.S. Appl. No. 12/205,431.
Advisory Action dated Apr. 20, 2012 for U.S. Appl. No. 10/678,741.
Final Office Action dated Oct. 11, 2012, for U.S. Appl. No. 12/205,431.
Japanese Notice of Reasons for Refusal Dated Jan. 5, 2012 for JP Application No. 2006-525439.
Japanese Notice of Reasons for Refusal Dated Jul. 25, 2011 for JP Application No. 2006-525439.
Japanese Notice of Reasons for Refusal Dated Aug. 9, 2010 for JP Application No. 2006-525439.
European Office Action Dated Mar. 12, 2012 for EP Application 04782961.9.
European Office Action Dated Apr. 21, 2010 for EP Application 04782961.9.
European Office Action Dated Mar. 29, 2011 for EP Application 04782961.9.
European Office Action Dated Sep. 7, 2010 for EP Application 04782961.9.
European Office Action Dated Apr. 28, 2011 for EP Application 04783114.4.
Japanese Decision to Dismiss the Amendment Dated Aug. 31, 2011 for JP Application 2006-526196.
Japanese Notice of Reason for Refusal Dated Feb. 21, 2011 for JP Application 2006-526196.
Japanese Notice of Reason for Refusal Dated Aug. 3, 2010 for JP Application 2006-526196.

(56) References Cited

OTHER PUBLICATIONS

Japanese Notice of Reason for Refusal Dated Apr. 7, 2010 for JP Application 2006-526196.
Japanese Notice of Questioning for Shimpan Appeal dated Sep. 12, 2012, for JP Application No. 2006-526196.
English Translation of Japanese Notice of Questioning for Shimpan Appeal dated Sep. 12, 2012, for JP Application No. 2006-526196.
European Office Action Dated Aug. 21, 2009 for EP Application 04793980.6.
European Office Action Dated Mar. 8, 2011 for EP Application 04793980.6.
European Office Action Dated Jun. 14, 2012 for EP Application No. 04793980.6.
European Office Action Dated Oct. 7, 2010 for EP Application 04783505.3.
European Supplementary Search Report Dated Jun. 16, 2010 for EP Application 04783505.3.
Japanese Notice of Reason for Refusal Dated Oct. 6, 2009 for JP Application 2006-525540.
Japanese Notice of Reason for Refusal Dated Mar. 17, 2010 for JP Application 2006-525540.
Japanese Notice of Reason for Refusal Dated Mar. 22, 2011 for JP Application 2006-525540.
Japanese Decision of Refusal Dated Apr. 21, 2009 for JP Application 2003-509826.
Notice of Questioning for Shimpan Appeal Dated Apr. 26, 2010 for JP Application 2003-509826.
English Abstract for Application No. JP 6-292085.
English Abstract for Application No. JP 7-275237.
English Abstract for Application No. JP 10-289321.
European Search Report and Opinion dated May 24, 2012 for EP Application No. 12164387.8.
European Office Action dated Jun. 5, 2012 for EP Application No. 04783114.4.
Final Office Action dated Sep. 4, 2012, for U.S. Appl. No. 12/205,512.
Advisory Action dated Nov. 9, 2012, for U.S. Appl. No. 12/205,512.
Final Office Action dated Nov. 7, 2012, for U.S. Appl. No. 12/182,932.
Final Office Action dated Dec. 19, 2012, for U.S. Appl. No. 10/656,478.
Notice of Reasons for Refusal dated Dec. 17, 2012 for Japanese Patent Application No. 2011-25872.
Office Action dated Nov. 7, 2012 for European Patent Application No. 04783114.4.
Final Office Action dated Feb. 1, 2013 for U.S. Appl. No. 10/655,920.
Advisory Action dated Jan. 9, 2013 for U.S. Appl. No. 12/205,431.
Notice of Reasons for Refusal dated Feb. 12, 2013 for JP Patent Application No. 2006-526196.
English Translation of Notice of Reasons for Refusal dated Feb. 12, 2013 for JP Patent Application No. 2006-526196.
First Examination Report dated Feb. 21, 2013 for EP Patent Application No. 12 164 387.8.
Advisory Action dated Apr. 10, 2013 for U.S. Appl. No. 10/655,920.
Notice of Reasons for Refusal dated Apr. 10, 2013, for JP Patent Application No. 2011-025872 (previously dated Apr. 3, 2013 (Drafting Date).
English Translation of Notice of Reasons for Refusal dated Apr. 10, 2013 for JP Patent Application No. 2011-025872.
Non-final Office Action dated May 31, 2013 for U.S. Appl. No. 10/678,741.
Notice of Allowance and Fees Due dated Jun. 19, 2013 for U.S. Appl. No. 10/655,920.

Office Action dated Aug. 2, 2013 for EP Patent Application No. 04793980.6, 4 pages.
E.C. Ford et al., "Respiration-correlated spiral CT: A method of measuring respiratory-induced anatomic motion for radiation treatment planning" Med. Phys. 30 (1), Jun. 13, 2002, 12 pages.
Notice of Allowance and Fees Due dated Oct. 15, 2013 for U.S. Appl. No. 10/678,741.
European Communication dated Nov. 14, 2013 for related EP Patent Application No. 04793980.6.
Intention to Grant dated Jan. 27, 2014 for related EP Patent Application No. 04793980.6.
Non-final Office Action dated May 3, 2016 for related U.S. Appl. No. 10/656,478.
Advisory Action dated Aug. 23, 2019 for related U.S. Appl. No. 12/182,932.
Final Office Action dated Nov. 8, 2019 for related U.S. Appl. No. 12/205,512.
Non-final Office Action dated Sep. 29, 2014 for U.S. Appl. No. 11/116,699.
Final Office Action dated May 1, 2015 for U.S. Appl. No. 11/116,699.
Notice of Allowance and Fee(s) due dated Aug. 31, 2015 for related U.S. Appl. No. 11/116,699.
Non-Final Office Action dated Apr. 17, 2017 for related U.S. Appl. No. 12/205,512.
Advisory Action dated May 9, 2017 for related U.S. Appl. No. 10/656,478.
Advisory Action dated May 17, 2017 for related U.S. Appl. No. 12/205,431.
Advisory Action dated Aug. 10, 2018 for related U.S. Appl. No. 12/205,512.
Non-Final Office Action dated Sep. 26, 2018 for related U.S. Appl. No. 12/182,932, 7 pages.
Final Office Action dated Jan. 20, 2017 for related U.S. Appl. No. 10/656,478.
Final Office Action dated Mar. 7, 2017 for related U.S. Appl. No. 12/205,431.
Final Office Action dated Apr. 3, 2017 for related U.S. Appl. No. 12/182,932.
Non-final Office Action dated Sep. 6, 2016 for related U.S. Appl. No. 12/182,932.
Non-final Office Action dated Oct. 4, 2016 for related U.S. Appl. No. 12/205,431.
Advisory Action dated Apr. 12, 2018 for related U.S. Appl. No. 10/656,478.
Final Office Action dated Apr. 16, 2018 for related U.S. Appl. No. 12/205,512.
Advisory Action dated Apr. 19, 2018 for related U.S. Appl. No. 12/205,431.
Non-final Office Action dated Jul. 7, 2017 for related U.S. Appl. No. 10/656,478.
Non-final Office Action dated Jul. 21, 2017 for related U.S. Appl. No. 12/205,431.
Non-final Office Action dated Sep. 18, 2017 for related U.S. Appl. No. 12/182,932.
Final Office Action dated Jan. 9, 2018 for related U.S. Appl. No. 12/205,431.
Final Office Action dated Jan. 22, 2018 for related U.S. Appl. No. 10/656,478.
Final Office Action dated Feb. 26, 2018 for related U.S. Appl. No. 12/182,932.
Notice of Allowance dated Jan. 27, 2020 for related U.S. Appl. No. 12/205,512.

* cited by examiner

METHOD AND SYSTEM FOR RADIATION APPLICATION

RELATED APPLICATION DATA

This application is a divisional of U.S. patent application Ser. No. 10/678,741, filed on Oct. 3, 2003, now issued as U.S. Pat. No. 8,788,020, which claims priority to U.S. Provisional Patent Application Ser. No. 60/415,992 filed Oct. 5, 2002, lapsed, and is a continuation-in-part of U.S. patent application Ser. No. 09/893,122 filed Jun. 26, 2001, now issued as U.S. Pat. No. 6,937,696, the disclosures of all of the above applications are hereby expressly incorporated by reference in their entirety.

FIELD

The present disclosure relates to medical methods and systems. More particularly, the invention relates to a method and system for physiological gating.

BACKGROUND

Many types of medical procedures involve devices and machines that act upon a particular portion of a patient body. For example, radiation therapy involves medical procedures that selectively expose certain areas of a human body, such as cancerous tumors, to high doses of radiation. The intent of the radiation therapy is to irradiate the targeted biological tissue such that the harmful tissue is destroyed. In certain types of radiotherapy, the irradiation volume can be restricted to the size and shape of the tumor or targeted tissue region to avoid inflicting unnecessary radiation damage to healthy tissue. Conformal therapy is a radiotherapy technique that is often employed to optimize dose distribution by conforming the treatment volume more closely to the targeted tumor.

Other medical procedures are also directed to specific portions of a patient body. For example, radiation imaging typically directs radiation only to the portion of a patient body to be imaged. 3-dimensional imaging applications such as computed topography (CT), PET, and MRI scans also are directed to specific portions of a patient body.

Normal physiological movement represents a limitation in the clinical planning and delivery of medical procedures to a patient body. Normal physiological movement, such as respiration or heart movement, can cause a positional movement of the body portion undergoing treatment, measurement, or imaging. With respect to radiation therapy, if the radiation beam has been shaped to conform the treatment volume to the exact dimensions of a tumor, then movement of that tumor during treatment could result in the radiation beam not being sufficiently sized or shaped to fully cover the targeted tumoral tissue. For imaging applications, normal physiological movement could result in blurred images or image artifacts.

One approach to this problem involves physiological gating of the medical procedure, such as gating of a radiation beam during treatment, with the gating signal synchronized to the movement of the patient's body. In this approach, instruments are utilized to measure the physiological state and/or movement of the patient. Respiration has been shown to cause movements in the position of a lung tumor in a patient's body; if radiotherapy is being applied to the lung tumor, then a temperature sensor, strain gauge, pneumotactrograph, or optical imaging system can be utilized to measure the patient during a respiration cycle. These instruments can produce a signal indicative of the movement of the patient during the respiratory cycle. The radiation beam can be gated based upon certain threshold amplitude levels of the measured respiratory signal, such that the radiation beam is disengaged or stopped during particular time points in the respiration signal that correspond to excessive movement of the lung tumor.

Many approaches to physiological gating are reactive, that is, these approaches utilize gating methods that slavishly react to measured levels of physiological movements. One drawback to reactive gating systems is that the measured physiological movement may involve motion that that is relatively fast when compared to reaction time of the imaging or therapy device that is being gated. Thus, a purely reactive gating system may not be able to react fast enough to effectively gate the applied radiation. For example, the gating system may include a switch or trigger for gating radiation which requires a given time period $\Delta t$ to fully activate. If the delay period $\Delta t$ is relatively long compared to the measured physiological motion cycle, then a system employing such a trigger in a reactive manner may not be able to effectively gate the radiation at appropriate time points to minimize the effect of motion.

Therefore, there is a need for a system and method to address these and other problems of the related art. There is a need for a method and system for physiological gating which is not purely reactive to measure physiological movement signals.

SUMMARY

In accordance with one embodiment, a method for generating one or more images includes collecting data samples representative of a motion of an object, acquiring image data of at least a part of the object over a time interval, synchronizing the data samples and the image data to a common time base, and generating one or more images based on the synchronized image data.

In accordance with another embodiment, a method for generating one or more images includes acquiring image data of at least a part of an object over a time interval, associating the image data with one or more phases of a motion cycle, and constructing one or more images using the image data that are associated with the respective one or more phases.

Other aspects and features will be evident from reading the following detailed description of the preferred embodiments, which are intended to illustrate, not limit, the claimed invention.

BRIEF DESCRIPTION OF THE DRAWINGS

FIG. 6a depicts a side view an embodiment of a camera and illuminator that can be utilized in the invention.

FIG. 6b depicts a front view of the camera of FIG. 6a.

FIG. 7a depicts a retro-reflective marker according to an embodiment of the invention.

FIG. 7b depicts a cross-sectional view of the retro-reflective marker of FIG. 7a.

DESCRIPTION OF THE ILLUSTRATED EMBODIMENTS

An aspect of an embodiment of the present invention comprises a method for detecting and predictively estimating regular cycles of physiological activity or movement. Also disclosed are embodiments of systems and devices for patient positioning, positioning monitoring, motion monitoring, and physiological gating of medical procedures such as imaging and radiation therapy. The systems and methods of the invention can be employed for any regular physiological activity, including for example, the respiratory or cardiac cycles, and for monitoring temporary breath-hold state of the patient.

System for Patient Position Monitoring and Physiological Gating

Figure 1:
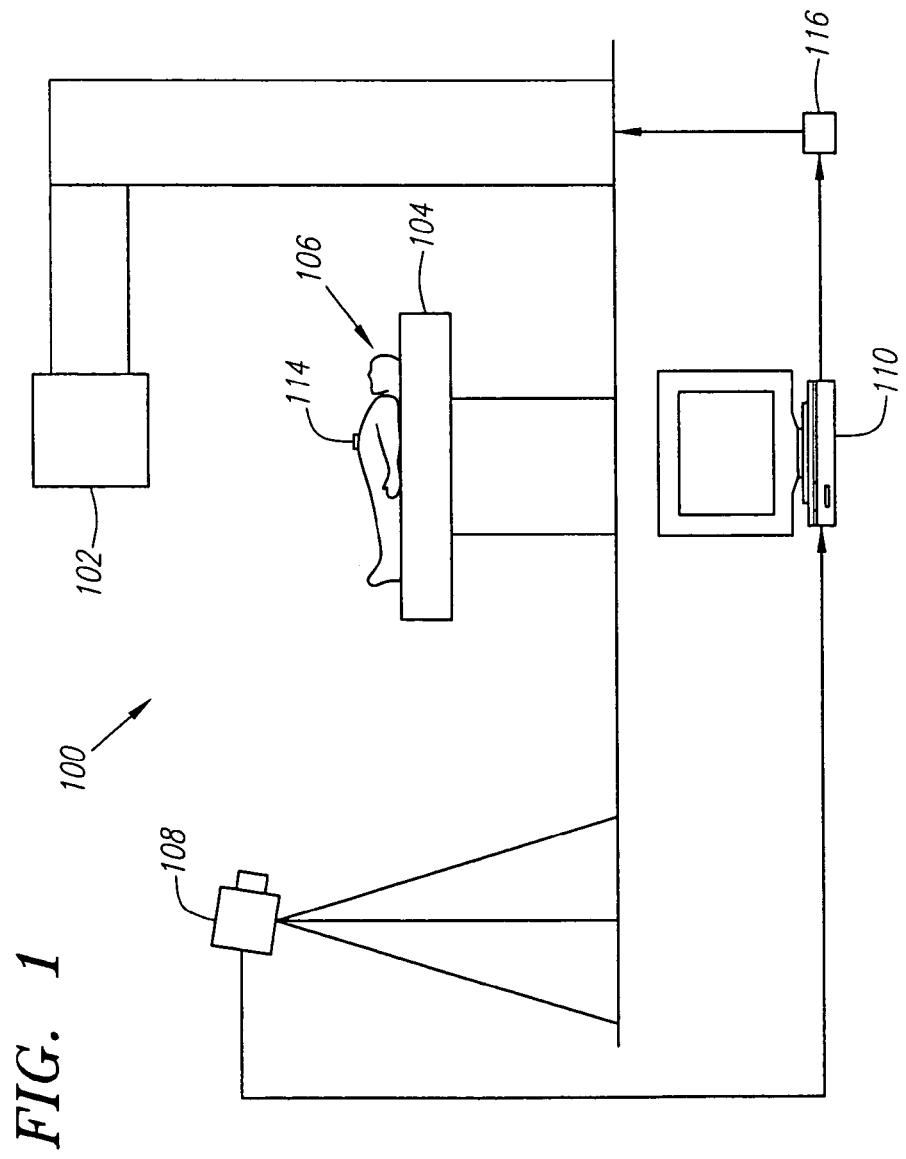
FIG. 1 depicts the components of a system for physiological gating according to an embodiment of the invention.

FIG. 1 depicts the components of an embodiment of a system 100 for physiological gating, position monitoring, and motion monitoring, in which data representative of physiological activity is collected with an optical imaging apparatus. For the purposes of illustration, system 100 is particularly described with reference to physiological gating of radiation therapy. Thus, system 100 comprises a radiation beam source 102 such as a conventional linear accelerator which is positionally configured to direct a radiation beam at a patient 106 located on treatment table 104. It is noted, however, that system 100 can also be applied to gate other medical procedures, such as gating for CT imaging applications or non-radioactive imaging applications such as MRI In system 100 for physiological gating, a switch 116 is operatively coupled to the radiation beam source 102. Switch 116 can be operated to suspend the application of the radiation beam at patient 106. In an embodiment, switch 116 is part of the mechanical and electrical structure of radiation beam source 102. Alternatively, switch 116 comprises an external apparatus that is connected to the control electronics of radiation beam source 102. Switch 116 may also comprise a software-based control mechanism.

An optical or video image apparatus, such as video camera 108, is aimed such that at least part of the patient 106 is within the camera's field of view. Camera 108 monitors patient 106 for motion relating to the particular physiological activity being measured. By way of example, if respiration movements of the patient are being monitored, then camera 108 is configured to monitor the motion of the patient's chest. According to an embodiment, camera 108 is placed on the ceiling, wall, or other support structure with its axis tilted down between 20 and 70 degrees relative to the horizontal longitudinal axis of the patient 106. For measurement of respiration motion, the video image field of view is preferably set to view an approximately 30 cm by 30 cm area of the patient's chest. For purposes of illustration only, a single camera 108 is shown in FIG. 1. However, the number of cameras 108 employed in the present invention can exceed that number, and the exact number to be used in the invention depends upon the particular application to which it is directed.

In an embodiment, one illumination source per camera (which is an infrared source in the preferred embodiment) projects light at the patient 106 on treatment table 104. The generated light is reflected from one or more landmarks on the patient's body. The camera 108, which is directed at patient 106, captures and detects the reflected light from the one or more landmarks. The landmarks are selected based upon the physiological activity being studied. For respiration measurements, the landmarks are preferably located on one or more locations on the patient's chest.

The output signals of camera 108 are sent to a computer 110 or other type of processing unit having the capability to receive video images. According to a particular embodiment, computer 110 comprises an Intel Pentium-based processor running Microsoft Windows NT or 2000 and includes a video frame grabber card having a separate channel for each video source utilized in the system. The images recorded by camera 108 are sent to computer 110 for processing. If camera 108 produces an analog output, the frame grabber converts the camera signals to a digital signal prior to processing by computer 110. Based upon the video signals received by computer 110, control signals can be sent from computer 110 to operate switch 116.

According to one embodiment, one or more passive markers 114 are located on the patient in the area to be detected for movement. Each marker 114 preferably comprises a reflective or retro-reflective material that can reflect light, whether in the visible or invisible wavelengths. If the illumination source is co-located with camera 108, then marker 114 preferably comprises a retro-reflective material that reflects light mostly in the direction of the illumination source. Alternatively, each marker 114 comprises its own light source. The marker 114 is used in place of or in conjunction with physical landmarks on the patient's body that is imaged by the camera 108 to detect patient movement. Markers 114 are preferably used instead of body landmarks because such markers 114 can be detected and tracked more accurately via the video image generated by camera 108. Because of the reflective or retro-reflective qualities of the preferred markers 114, the markers 114 inherently provide greater contrast in a video image to a light detecting apparatus such as camera 108, particularly when the camera 108 and illumination source are co-located.

Utilizing a video or optical based system to track patient movement provides several advantages. First, a video or optical based system provides a reliable mechanism for repeating measurement results between uses on a given patient. Second, the method of the invention is noninvasive, and even if markers are used, no cables or connections must be made to the patient. Moreover, if the use of markers is impractical, the system can still be utilized without markers by performing measurements of physiological activity keyed to selected body landmarks. Finally, the method of the invention is more accurate because it is 110 based upon absolute measurement of external anatomical physical movement. The present patient monitoring system is particularly suitable to track motion and position of patients for which intrusive/cumbersome equipment cannot or should not be used. For example, the present optical-based system is suitable for monitoring the movement and position of infants.

A possible inefficiency in tracking the markers 114 is that the marker may appear anywhere on the video frame, and all of the image elements of the video frame may have to be examined to determine the location of the marker 114. Thus, in an embodiment, the initial determination of locations for the marker 114 involves an examination of all of the image elements in the video frame. If the video frame comprise 640 by 480 image elements, then all 307200 (640*480) image elements are initially examined to find the location of the markers 114.

For real-time tracking of the marker 114, examining every image element for every video frame to determine the location of the marker 114 in real-time could consume a significant amount of system resources. Thus, in an embodiment, the real-time tracking of marker 114 can be facilitated by processing a small region of the video frame, referred to herein as a "tracking gate", that is placed based on estimation of the location of the already-identified marker 114 in a previous video frame. The previously determined location of a marker 114 defined in the previous video frame is used to define an initial search range (i.e., the tracking gate) for that same marker in real-time. The tracking gate is a relatively small portion of the video frame that, in one embodiment, is centered at the previous location of the marker 114. The tracking gate is expanded only if the tracking algorithm can not locate the marker 114 within the gate. As an example, consider the situation when the previously determined location of a particular marker is image element (50, 50) in a video frame. If the tracking gate is limited to a 50 by 50 area of the video frame, then the tracking gate for this example would comprise the image elements bound within the area defined by the coordinates (25,25), (25, 75), (75, 25), and (75, 75). The other portions of the video frame are searched only if the marker 106 is not found within this tracking gate.

Figure 2:
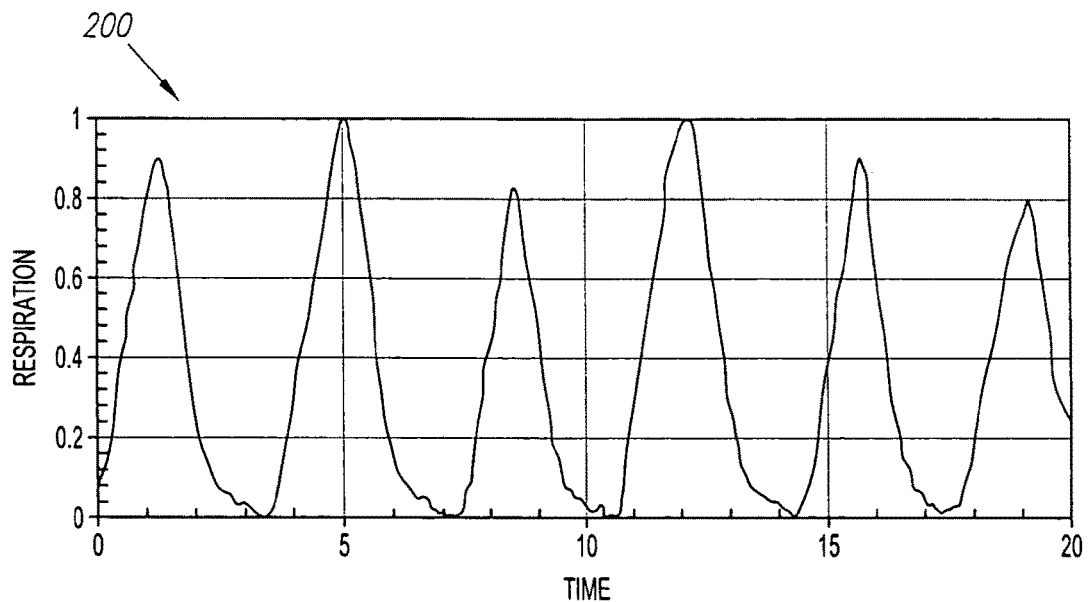
FIG. 2 depicts an example of a respiratory motion signal chart.

The video image signals sent from camera 108 to computer 110 are used to generate and track motion signals representative of the movement of marker 114 and/or landmark structures on the patient's body. FIG. 2 depicts an example of a motion signal chart 200 for respiratory movement that contains information regarding the movement of marker 114 during a given measurement period. The horizontal axis represents points in time and the vertical axis represents the relative location or movement of the marker 114. According to an embodiment, the illustrated signal in FIG. 2 comprises a plurality of discrete data points plotted along the motion signal chart 200.

Figures 6A, 6B:
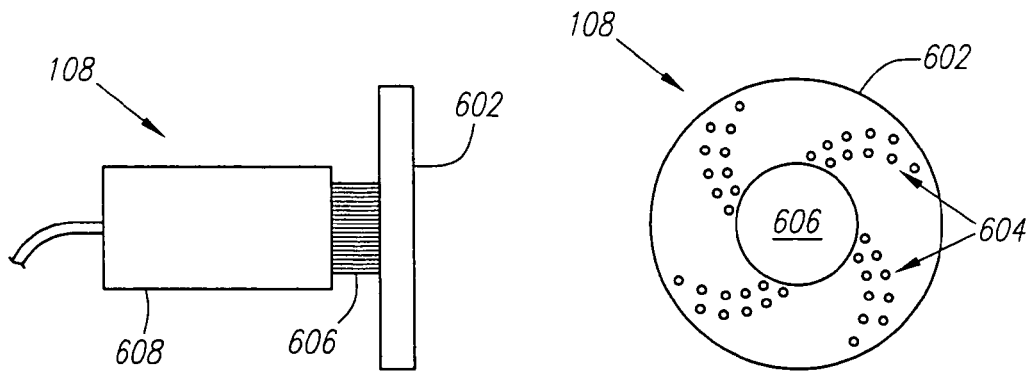

FIGS. 6*a* and 6*b* depict an embodiment of a camera 108 that can used in the present invention to optically or visually collect data representative of physiological movement. Camera 108 is a charge-couple device ("CCD") camera having one or more photoelectric cathodes and one or more CCD devices. A CCD device is a semiconductor device that can store charge in local areas, and upon appropriate control signals, transfers that charge to a readout point. When light photons from the scene to be imaged are focussed on the photoelectric cathodes, electrons are liberated in proportion to light intensity received at the camera. The electrons are captured in charge buckets located within the CCD device. The distribution of captured electrons in the charge buckets represents the image received at the camera. The CCD transfers these electrons to an analog-to-digital converter. The output of the analog-to-digital converter is sent to computer 410 to process the video image and to calculate the positions of the retro-reflective markers 406. According to an embodiment of the invention, camera 108 is a monochrome CCD camera having RS-170 output and 640×480 pixel resolution. Alternatively, camera 408 can comprise a CCD camera having CCIR output and 756×567 pixel resolution.

In a particular embodiment of the invention, an infra-red illuminator 602 ("IR illuminator") is co-located with camera 108. IR illuminator 602 produces one or more beams of infrared light that is directed in the same direction as camera 108. IR illuminator 602 comprises a surface that is ringed around the lens 606 of camera body 608. The surface of IR illuminator 602 contains a plurality of individual LED elements 604 for producing infrared light. The LED elements 604 are organized as one or more circular or spiral patterns on the IR illuminator 602 surrounding the camera lens 606. Infrared filters that may be part of the camera 108 are removed or disabled to increase the camera's sensitivity to infrared light.

According to an embodiment, digital video recordings of the patient in a session can be recorded via camera 108. The same camera 108 used for tracking patient movement can be used to record video images of the patient for future reference. A normal ambient light image sequence of the patient can be obtained in synchronization with the measured movement signals of markers 114.

Figures 7A, 7B:
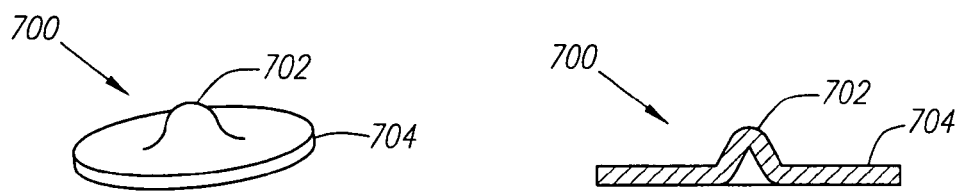

FIGS. 7*a* and 7*b* depict an embodiment of a retro-reflective marker 700 that can be employed within the present invention. Retro-reflective marker 700 comprises a raised reflective surface 702 for reflecting light. Raised reflective surface 702 comprises a semi-spherical shape such that light can be reflected regardless of the input angle of the light source. A flat surface 704 surrounds the raised reflective surface 702. The underside of flat surface 704 provides a mounting area to attach retro-reflective marker 700 to particular locations on a patient's body. According to an embodiment, retro-reflective marker 700 is comprised of a retro-reflective material 3M#7610WS available from 3M Corporation. In an embodiment, marker 700 has a diameter of approximately 0.5 cm and a height of the highest point of raised reflective surface 702 of approximately 0.1 cm. Alternatively, a marker can comprise a circular, spherical, or cylindrical shape.

Figure 8:
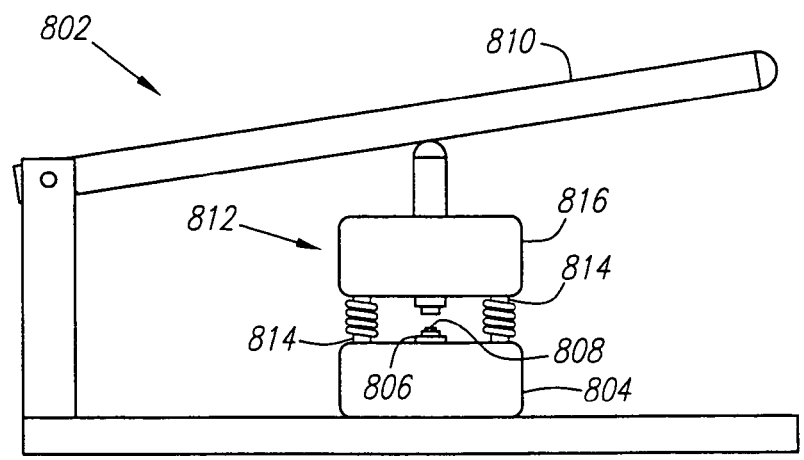
FIG. 8 depicts an apparatus for making a retro-reflective marker.

FIG. 8 depicts an apparatus 802 that can be employed to manufacture retro-reflective markers 700. Apparatus 802 comprises a base portion 804 having an elastic ring 806 affixed thereto. Elastic ring 806 is attached to bottom mold piece 808 having a bulge protruding from its center. A control lever 810 can be operated to move top portion 812 along support rods 814. Top portion 812 comprises a spring-loaded top mold piece 814. Top mold piece 814 is formed with a semi-spherical cavity on its underside. In operation, a piece of retro-reflective material is placed on bottom mold piece 808. Control lever 810 is operated to move top portion 812 towards base portion 804. The retro-reflective material is compressed and shaped between the bottom mold piece 808 and the top mold piece 814. The top mold piece 814 forms the upper exterior of the retro-reflective material into a semi-spherical shape.

In an alternate embodiment, marker 114 comprises a marker block having one or more reference locations on its surface. Each reference location on the marker block preferably comprises a retro-reflective or reflective material that is detectable by an optical imaging apparatus, such as camera 108.

According to one embodiment of the invention, physiological gating is performed by sensing physiological motion, e.g., respiration motion, using video tracking of retro-reflective markers attached to a marker block. One embodiment of the marker block 1471 utilizes two markers 1473 and 1475 on a rigid hollow and light plastic block 1477 measuring about 6 Cm×4 Cm×4 Cm as shown in FIG. 14c. The two markers 1473 and 1475 are preferably placed at a fixed distance of three centimeter on the side of the block that will face the tracking camera. The fixed distance between the two markers 1473 and 1475 is known and is used to calibrate the motion of the block in the direction of the line connecting the two markers.

According to one embodiment, the pixel coordinates of each marker in the video frame are tracked. The distance in the pixel domain between the two markers for each video frame is thereafter measured. The known physical distance of the two markers is divided by the measured distance to provide the scale factor for transforming the incremental motion of the block in the direction of the line connecting the two markers. This scale factor is updated for each new video frame and transforms the incremental motion of each marker from pixel domain to the physical domain. The transformation accounts for changes in the camera viewing angle, marker block orientation, and its distance to the camera during motion tracking.

Figure 11:
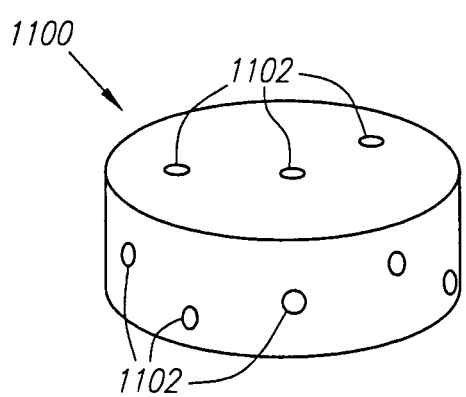
FIG. 11 depicts an embodiment of a cylindrical marker block.

FIG. 11 depicts alternate embodiment of a marker block 1100 having a cylindrical shape with multiple reference locations comprised of retro-reflective elements 1102 located on its surface. Marker block 1100 can be formed as a rigid block (e.g., from plastic). Blocks made in this fashion can be reused a plurality of times, even with multiple patients, e.g., if the normal hospital anti-infection procedures are followed. The retro-reflective elements 1102 can be formed from the same material used to construct retro-reflective markers 114 of FIGS. 7a and 7b. The marker block is preferably formed from a material that is light-weight enough not to interfere with normal breathing by the patient.

Figure 10:
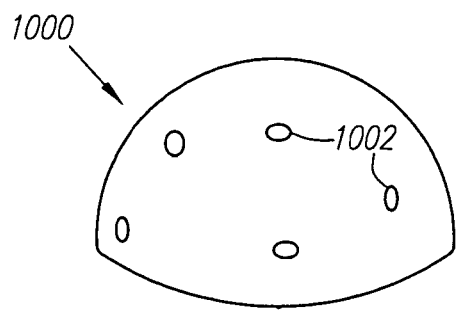
FIG. 10 depicts an embodiment of a hemispherical marker block.

A marker block can be formed into any shape or size, as long as the size, spacing, and positioning of the reference locations are configured such that a camera or other optical imaging apparatus can view and generate an image that accurately shows the positioning of the marker block. For example, FIG. 10 depicts an alternate marker block 1000 having a hemispherical shape comprised of a plurality of retro-reflective elements 1002 attached to its surface.

The marker block can be formed with shapes to fit particular body parts. For example, molds or casts that match to specific locations on the body can be employed as marker blocks. Marker blocks shaped to fit certain areas of the body facilitate the repeatable placement of the marker blocks at particular locations on the patient. Alternatively, the marker blocks can be formed to fit certain fixtures that are attached to a patient's body. For example, a marker block can be formed within indentations and grooves that allow it to be attached to eyeglasses. In yet another embodiment, the fixtures are formed with integral marker block(s) having reflective or retro-reflective markers on them.

An alternate embodiment of the marker block comprises only a single reference location/reflective element on its surface. This embodiment of the marker block is used in place of the retro-reflective marker 406 to detect particular locations on a patient's body with an optical imaging apparatus.

Figure 14A:
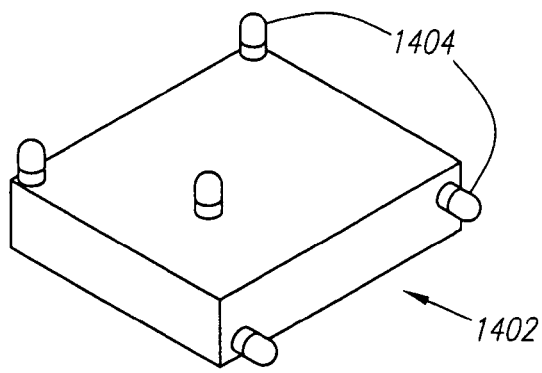
FIGS. 14a, 14b, and 14c depict embodiments of a marker block.
Figure 14B:
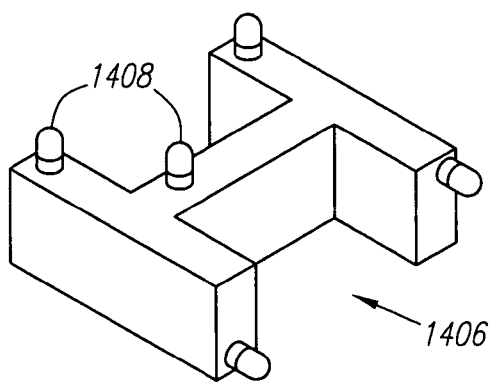
Figure 14C:
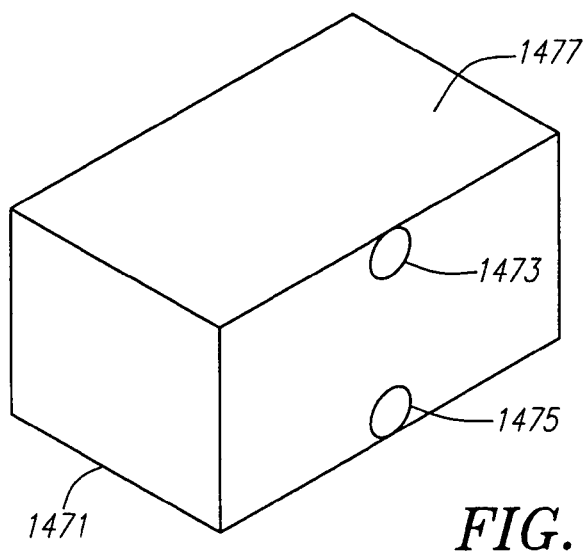

FIGS. 14a and 14b depict other embodiments of marker blocks 1402 and 1406 usable in the invention. Marker block 1402 includes a rectangular shape having multiple reflective or retro-reflective marker elements 1404 located on it. Marker block 1402 supports a rigidly mounted set of markers 14504 spread over an approximate volume of 1.5"×3"×4". The markers should appear as high contrast features in a real-time imaging device such as a video camera whose images are digitized and processed by a computer system. This realization of the marker block employs retro-reflective material covering a set of 0.25-inch diameter spheres glued or otherwise attached to a rigid plastic box or platform. Marker block 1406 includes a non-rectangular structure having multiple reflective or retro-reflective marker elements 1408 located on it. In an embodiment, the marker block is attached to the patient using standard hospital adhesive tape. In applications for which patient position and motion is monitored in multiple patient visits within a common set of reference coordinates, the marker block is preferably positioned for each visit at the same location, e.g., using two or more indelible marks on the patient skin.

Patient position and motion can be monitored by optical tracking of a marker block, such as a marker block 1402 or 1406, attached to a patient chest, abdomen, back, or other suitable patient location. In operation, a camera or video view of the marker block produces a set of image coordinates for the marker elements on the marker block. The position and distance of any marker element located on the marker block is known relative to other marker elements on the same marker block. By comparing the position and distance between the marker elements on a recorded image frame with the reference position and image stored for the monitoring system, the absolute position and orientation of the marker block can be estimated with a high degree of accuracy. This, in turn, provides an accurate position and orientation estimation for the patient or patient body position upon which the marker block is attached. Note that estimation of patient position and orientation can be performed in the invention using only a single marker block, rather requiring the placement of multiple markers on different parts of a patient's skin. Moreover, a single camera can be used to track the position of the marker block, rather than requiring triangulation using multiple cameras from different positions.

Figure 15:
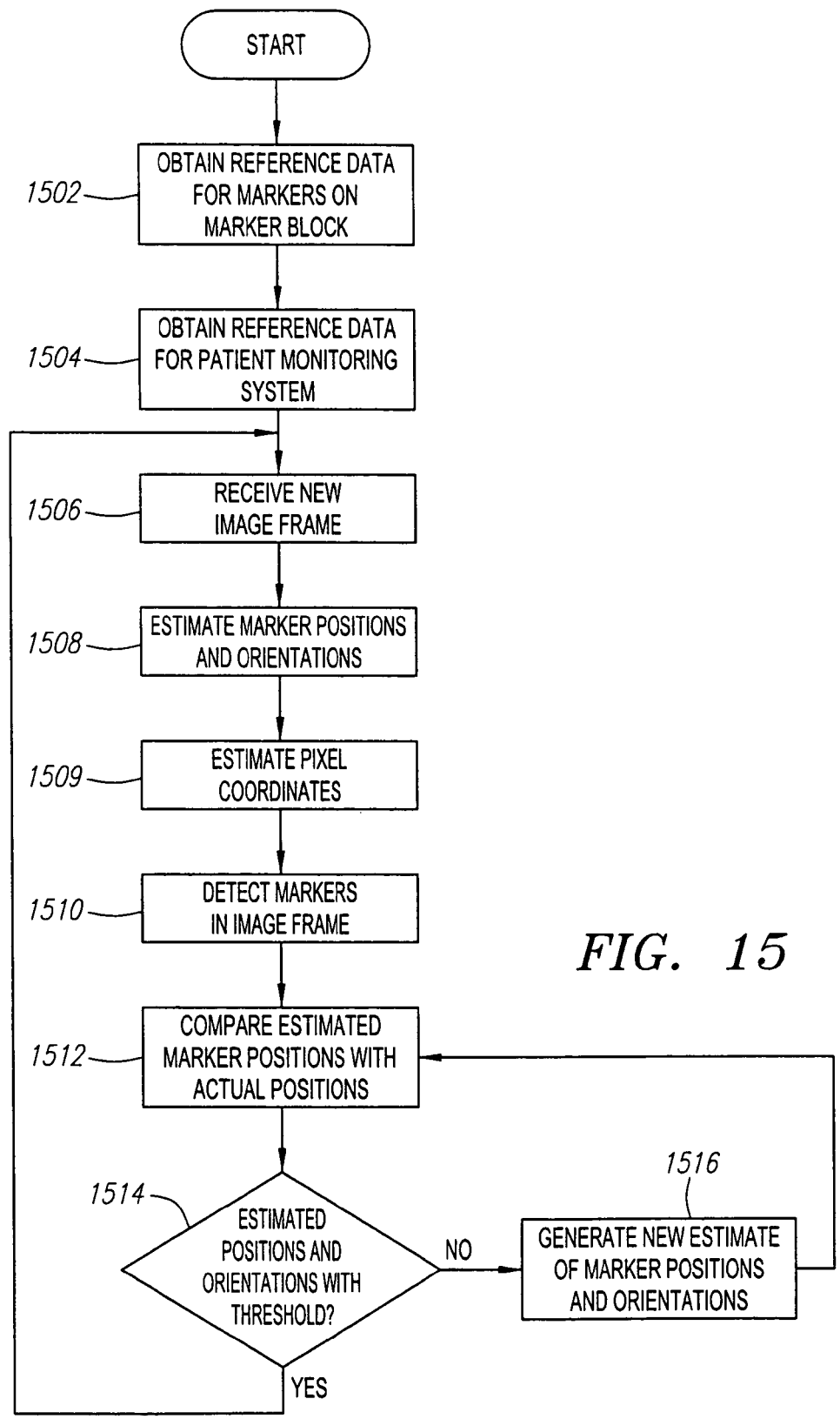
FIG. 15 shows a flowchart of a process for estimating position and orientation of a marker block according to an embodiment of the invention.

FIG. 15 depicts a flowchart of a process for tracking a marker block (e.g., marker blocks shown in FIG. 14a or 14b) using a single camera according to an embodiment of the invention. At step 1502, the coordinates of the markers on the marker block are accurately surveyed in a coordinate system affixed to the marker block. This survey data is stored as reference data, and provides the known relative positioning and distances between markers on the marker block. At step 1504, the geometric calibration model of the overall imaging chain is obtained and stored. The parameters of this model relate the position of a point in 3-dimensional reference coordinates of the room or treatment area where the patient is located to the 2-dimensional image coordinates of the corresponding pixel in the digital image. This calibration model for both steps 1502 and 1504 can be derived offline, e.g., after the camera is mounted rigidly in the room, and is preferably repeated occasionally as a check.

At step 1506, a new image frame is digitized from the camera video stream. At step 1508, an estimated position and orientation for the marker block is determined. The position and orientation of the marker block can be quantified in six degrees of freedom (DOF), e.g., x-coordinate, y-coordinate, z-coordinate, pitch, yaw, and roll. This estimated position and orientation is preferably using the same coordinate system affixed to the marker block and used for the survey of step 1502. This initial six DOF can be the approximate known marker block position and orientation, e.g., from the latest successful estimation of the marker block six DOF in a previous image frame in the video stream.

At step 1509, the estimated marker block six DOF, the geometric calibration model from step 1504, and the marker survey data from step 1502 are used to mathematically project the center of each marker and obtain an estimated pixel coordinates of each marker in the image frame.

At step 1510, the digitized image frame from step 1506 is analyzed to detect and locate the markers in pixel coordinates. If the previous tracking was successful, use the projected centers of step 1509 to limit the search area for each marker to increase the computational efficiency. If processing the first image frame, or recovering from lost track, then the whole frame is analyzed to find and locate markers. If three or more markers are found by the image analysis process, then proceed to Step 1512; otherwise, the process returns back to Step 1506 for a new image frame in the input video stream. In an embodiment of the invention, a subset of three or more markers should be visible to ensure a proper calculation of the six DOF coordinates for the marker block. However, this subset can vary from frame to frame in the input video stream.

At step 1512, the mathematically projected pixel coordinates are compared with the actual marker pixel coordinates. If the difference, e.g., measured in mean of squared distances in pixel domain, is below a threshold then the marker block six DOF (from step 1508) is accepted as the final estimate of the marker block for the current image frame. The process then returns to step 1506 for the next image frame in the video stream.

If the difference between the mathematically projected pixel coordinates and the actual marker pixel coordinates exceed a defined threshold, then the procedure proceeds to step 1516 to estimate a new six DOF for the marker block. The new six DOF for the marker block is estimated based upon incremental changes to the assumed marker block six DOF that would result in a closer match between the mathematically projected points and the marker coordinates found in the actual digitized image. One approach for this estimation uses the Gauss method based on computing the inverse Jacobian matrix of pixel positions as a function of the six DOF parameters. The process uses this incremented marker block six DOF as the new assumed six DOF for the marker block and iterates by looping back to step 1512.

While the process of FIG. 15 is usable with only a single camera, multiple cameras can also be used to expand the viewing volume of the patient monitoring system, or to allow continued operation of the system when the view of one camera is obstructed. When multiple cameras are used, the above process can be employed for each camera, independently, or triangulation of image data can alternatively be used to provide coordinates for the marker block.

The output of the process of FIG. 15 comprises position and orientation data for the marker block that can be correlated to the position and orientation of a patient to which it is attached. Analysis of simultaneously recorded internal image data, e.g., fluoroscopic video, can also be used to confirm correlation of these externally attached markers with internal organ motion. Tracking of the marker block allows monitoring of the patient motion in diagnostic and therapy imaging applications where image data acquisition is gated or synchronized with periodic motion. It can also be used to monitor position in imaging or therapy machine coordinates for procedures that use the breath-hold method. As described in more detail below, the amplitude and/or phase of the marker block coordinates vs. time, corresponding to the motion and phase of patient physiological activity, can be used to trigger image acquisition or non-acquisition at specific points during normal periodic cycle (e.g., breathing cycle) to minimize image distortion effects of patient motion. The amplitude and/or phase can also be used to trigger treatment or non-treatment at specific points during the normal periodic movements.

The marker block position can also be treated as a signal that is processed to detect deviations from periodic breathing such as those caused by coughing. This condition is used to stop image acquisition or delivery of radiation therapy to minimize the effects of unplanned motion.

In addition, the instantaneous marker block position can be used as a respiration monitor signal. Rather than requiring cumbersome or intrusive devices to monitor respiration of a patient, the video approach of this embodiment of the invention provides a non-intrusive mechanism to monitor patient respiration. The measured movement of the marker block can be used as an indicator of patient respiration. Thus, quantifiable values such as amplitude and/or phase of the marker block movement can be generated to monitor patient respiration. These values can be displayed and analyzed for breathing patterns using any conventional respiration analysis algorithms.

Physiological Gating

The following description of physiological gating applies to controlling radiation in radiation therapy/imaging and to controlling the image acquisition process in imaging applications. Furthermore, the techniques are applicable to the breath-hold method of therapy and imaging as well as gating in normal periodic breathing mode. For radiation procedures, e.g., X-ray radiotherapy and CT imaging, gating is performed by synchronizing the application of radiation to physiological activity such as patient motion. In emission imaging methods such as PET and MRI, the acquisition of data can be synchronized with patient motion so that the data corresponding to a specific position or state of the patient is "binned" separately to minimize the effect of motion.

To perform physiological gating according to an embodiment of the invention, one or more sets of data representative of the physiological activity of interest are collected for the patient in an embodiment of the invention. An optical-based system, such as system 100 of FIG. 1 using marker(s)

or a marker block, may be employed to generate data for physiological activity usable in the invention.

One aspect of physiological gating is the determination of the boundaries of the treatment interval or interval range for applying radiation or gating data acquisition. For gating purposes, threshold points can be defined over the amplitude range of the motion signal to determine the boundaries of the treatment intervals. Motion of the external marker(s) that falls outside the boundaries of the treatment intervals correspond to movement that is predicted to cause unacceptable levels of movement. The external marker(s) motion is therefore accepted as a surrogate for the motion of internal anatomy and is thus used to control the imaging or therapy process. According to an embodiment, the treatment intervals correspond to the portion of the physiological cycle in which motion of the clinical target volume is minimized. Other factors for determining the boundaries of the treatment intervals include identifying the portion of the motion signals involving the least movement of the target volume or the portion of the motion signal involving the largest separation of the target volume from organs at risk. Thus, the radiation beam pattern can be shaped with the minimum possible margin to account for patient movement.

Figure 3:
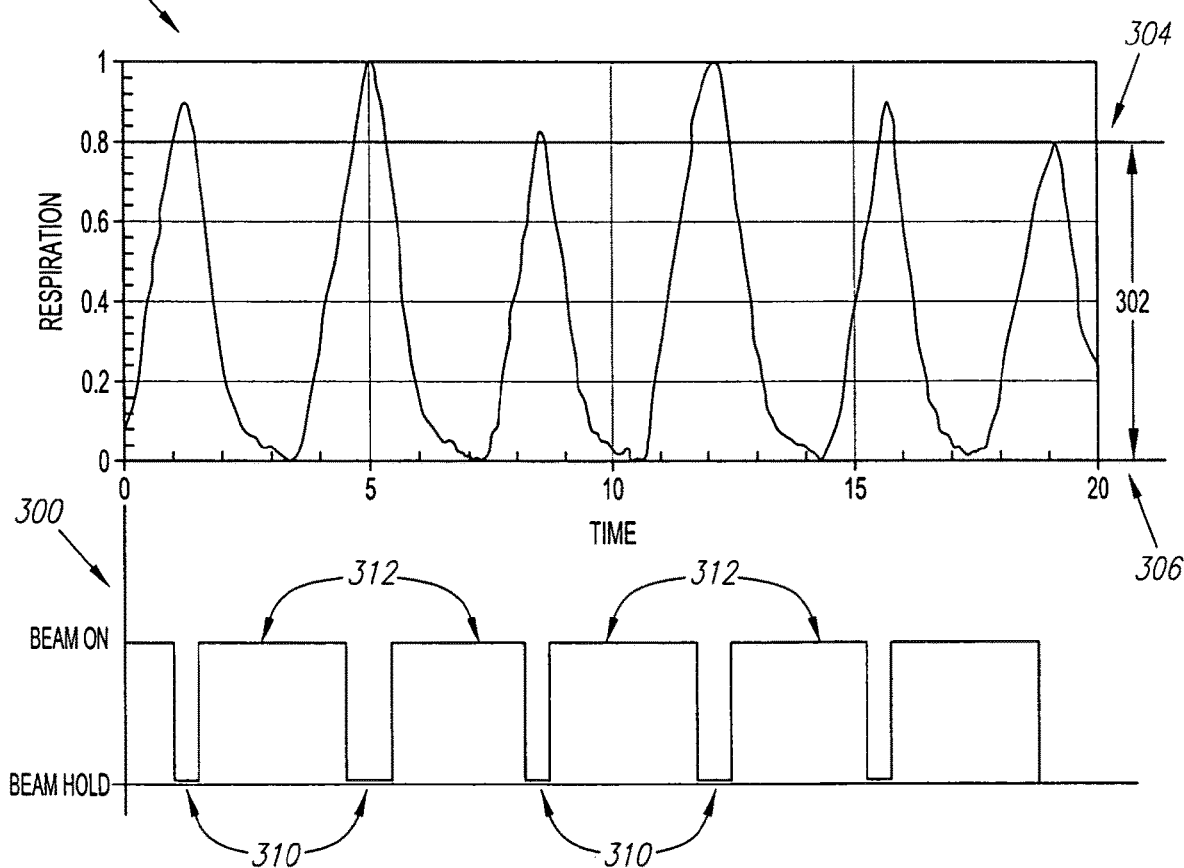
FIG. 3 depicts a motion signal chart and a gating signal chart.

To illustrate with respect to radiation therapy, radiation is applied to the patient only when the motion signal is within the designated treatment intervals. Referring to FIG. 3, depicted are examples of treatment intervals, indicated by signal range 302, which has been defined over the motion data shown in motion signal chart 200. In the example of FIG. 3, any movement of the measured body location that exceeds the value of 0.4 (shown by upper boundary line 304) or which moves below the value of 0.0 (shown by lower boundary line 306) falls outside the boundaries of the treatment intervals.

Shown in FIG. 3 is an example of a gating signal chart 300 that is aligned with motion signal chart 200. Any motion signal that falls outside the treatment interval signal range 302 results in a "beam hold" gating signal threshold 310 that stops the application of radiation to the patient. Any motion signal that is within the treatment interval signal range 302 results in a "beam on" gating signal threshold 312 that allows radiation to be applied to the patient. In an embodiment, digital signals that represent the information shown in motion signal chart 200 are processed by computer 110 and compared to the threshold levels of the treatment interval signal range 302 to generate gating signal thresholds 310 and 312. Alternatively, gating signal thresholds 310 and 312 can be obtained by feeding analog motion signals to a comparator to be compared with analog threshold signals that correspond to treatment interval signal range 302. In any case, gating signal thresholds 310 and 312 are generated by computer 110 and are applied to the switch 116 that controls the operation of radiation beam source 102 (FIG. 1) to stop or start the application of a radiation beam at patient 106.

Figure 4:
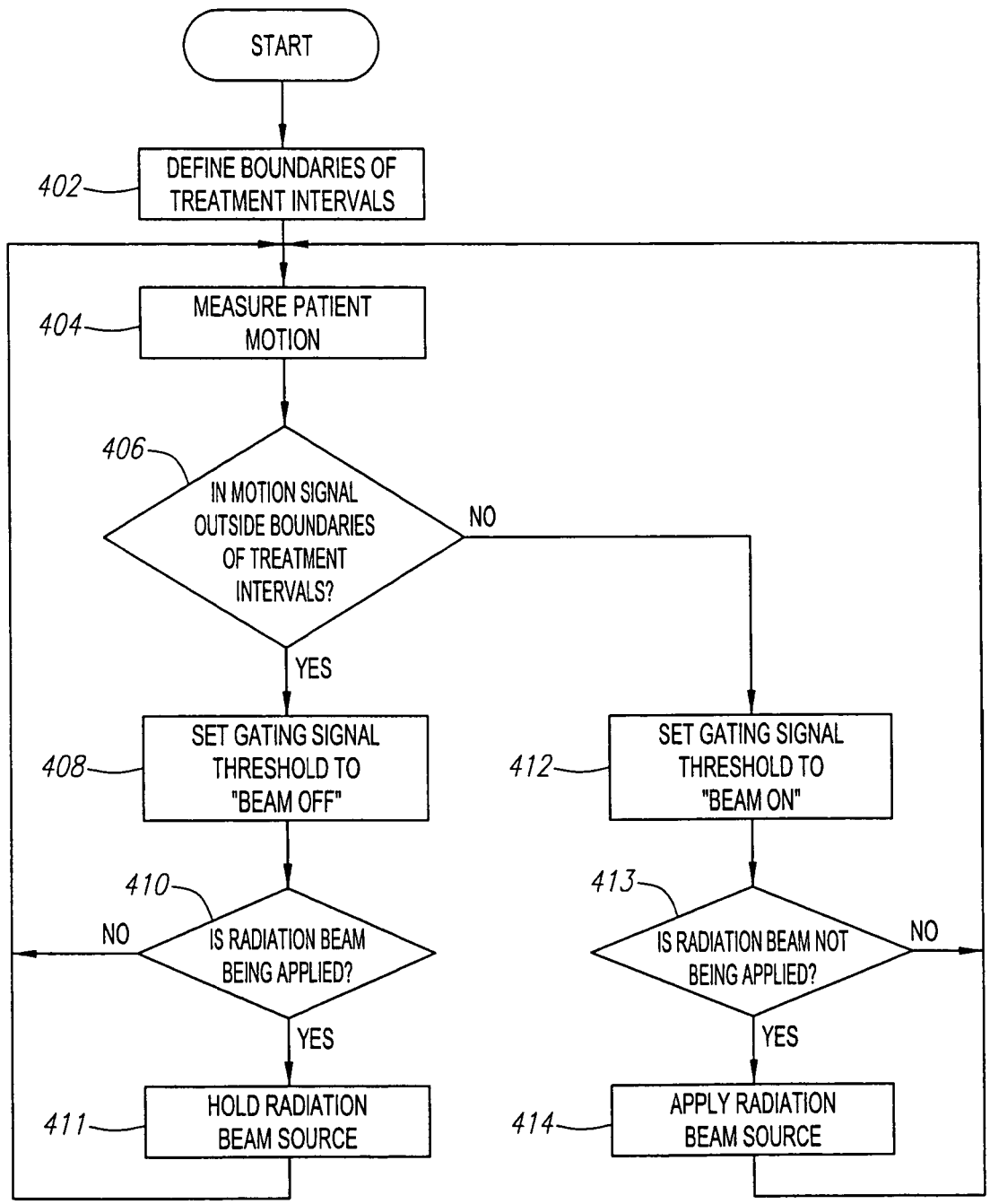
FIG. 4 is a flowchart showing process actions performed in an embodiment of the invention.

FIG. 4 is a flowchart of the process actions performed in an embodiment of the invention. The first process action is to define boundaries for the treatment intervals over the range of motion signals to be detected by a camera (402). As indicated above, any motion that fall outside the boundaries of the treatment intervals correspond to motion that is predicted to result in unacceptable levels of movement of the tumor or tissue targeted for irradiation. An optical or video imaging system, such as a video camera, is used to measure the physiological motion of the patient (404), and the output signals of the optical or video imaging system are processed to compare the measured motion signals with the threshold boundaries of the treatment intervals (406).

If the motion signal is outside the boundaries of the treatment intervals, then a "beam off" gating signal threshold is applied to a switch that is operatively coupled to the radiation beam source (408). If the radiation beam source is presently irradiating the patient (410), then the switch setting is operated to hold or stop the radiation beam (411). The process then returns back to process action 406.

If the motion signal is within the boundaries of the treatment intervals, then a "beam on" gating signal threshold is produced (412) and is applied to a switch that is operatively coupled to the radiation beam source. If the radiation beam source is presently not being applied to the patient (413), then the switch setting is operated to turn on or apply the radiation beam source to irradiate the patient (414). The process then returns back to process action 406.

According to one embodiment, the radiation beam source can be disengaged if a significant deviation is detected in the regular physiological movements of the patient. Such deviations can result from sudden movement or coughing by the patient. The position and/or orientation of the targeted tissue may unacceptably shift as a result of this deviation, even though the amplitude range of the motion signal still falls within the boundaries of the treatment intervals during this deviation. Thus, detection of such deviations helps define the appropriate time periods to gate the radiation treatment.

The present invention can be applied to perform physiological gating of other medical procedures that are affected by patient movement, in addition to radiation therapy. For example, imaging procedures, such as CT, PET, and MRI scans, are subject to a range of image errors due to patient movement, including blurring, smearing, and the appearance of image artifacts. One or more treatment intervals or range intervals, e.g., as shown in FIG. 3, are established over the imaging cycle to gate the collection of image data from the patient. The treatment intervals define boundaries of physiological movement that is predicted to increase the likelihood of image errors. Motion within the boundaries of the treatment interval is predicted to correspond to fewer image errors. The treatment intervals are used to gate the application of radiation or acquisition of images from the patient using an imaging device. For example, during the "beam hold" portion of the treatment interval, the application of radiation for a CT system can be suspended. During the "beam on" portion of the treatment interval, radiation is applied to the patient from the CT system to generate image data. Alternatively, gating can be performed by merely suspending the collection of data, even though the imaging device is still activated. For example, the CT system may still apply radiation to the patient through its entire cycle, but physiological gating is performed to suspend the recordation of data during the gating periods.

Retrospective Gating

In 3-dimensional imaging applications such as CT, PET and MRI, the signal representing physiologically activity can also be used to retrospectively "gate" the reconstruction process. For this purpose, the acquisition of raw transmission data or emission data (or emission events as in the case for PET) is synchronized to a common time base with the physiological signal. Segments of the acquired raw data that correspond to movement cycle intervals of interest are used to reconstruct the volumetric image thus minimizing the distortion and size changes caused by patient motion. For example, a gantry of a CT machine can rotate about a patient to obtain image data (i.e., segments of raw data) of a portion of the patient, while data samples associated with a physiological movement (e.g., a respiratory or a cardiac movement) of the patient is collected. The data samples are then synchronized with the image data to a common time base, and the synchronized image data can be used to construct one or more volumetric images. Any of the systems and/or methods described herein can be used to perform these functions.

In some embodiments, the image data associated with different amplitude ranges of a physiological movement of the patient are used to construct volumetric images for the respective amplitude ranges. In such cases, any of the systems and methods described herein can be used to obtain a motion signal chart showing how amplitude(s) of motion varies over time. Different amplitude ranges can be prescribed over a physiological cycle, and after image data are synchronized with the motion data to a common time base, image data that are generated during a prescribed amplitude range can be grouped together to construct a volumetric image for that amplitude range. Since a motion signal chart within a physiological cycle can have two points that correspond to the same amplitude (i.e., due to a rise and fall of a breathing), the phases of a physiological movement can be used to ensure that image data generated during a rise of a breathing are separately grouped from image data generated during a fall of a breathing. In alternative embodiments, amplitude ranges can be prescribed over less than one physiological cycle or more than one physiological cycle.

In alternative embodiments, the image data associated with different phases of a physiological movement of the patient are used to construct volumetric images for the respective phases. In such cases, image data that are associated with a same phase of a physiological cycle are selected to construct a volumetric image for that phase. The gantry of the CT machine can make additional revolution(s) about the patient to collect additional image data until all required image data associated with all phases (or prescribed phase(s)) of a physiological cycle have been obtained. In one embodiment, the image data can be sorted or processed such that image data associated with a phase range of a physiological cycle are grouped together, or associated with each other. A processor and/or a software can be configured to perform such function and to select image data that are associated with a same phase range of a physiological cycle for constructing the volumetric image(s).

Figure 25:
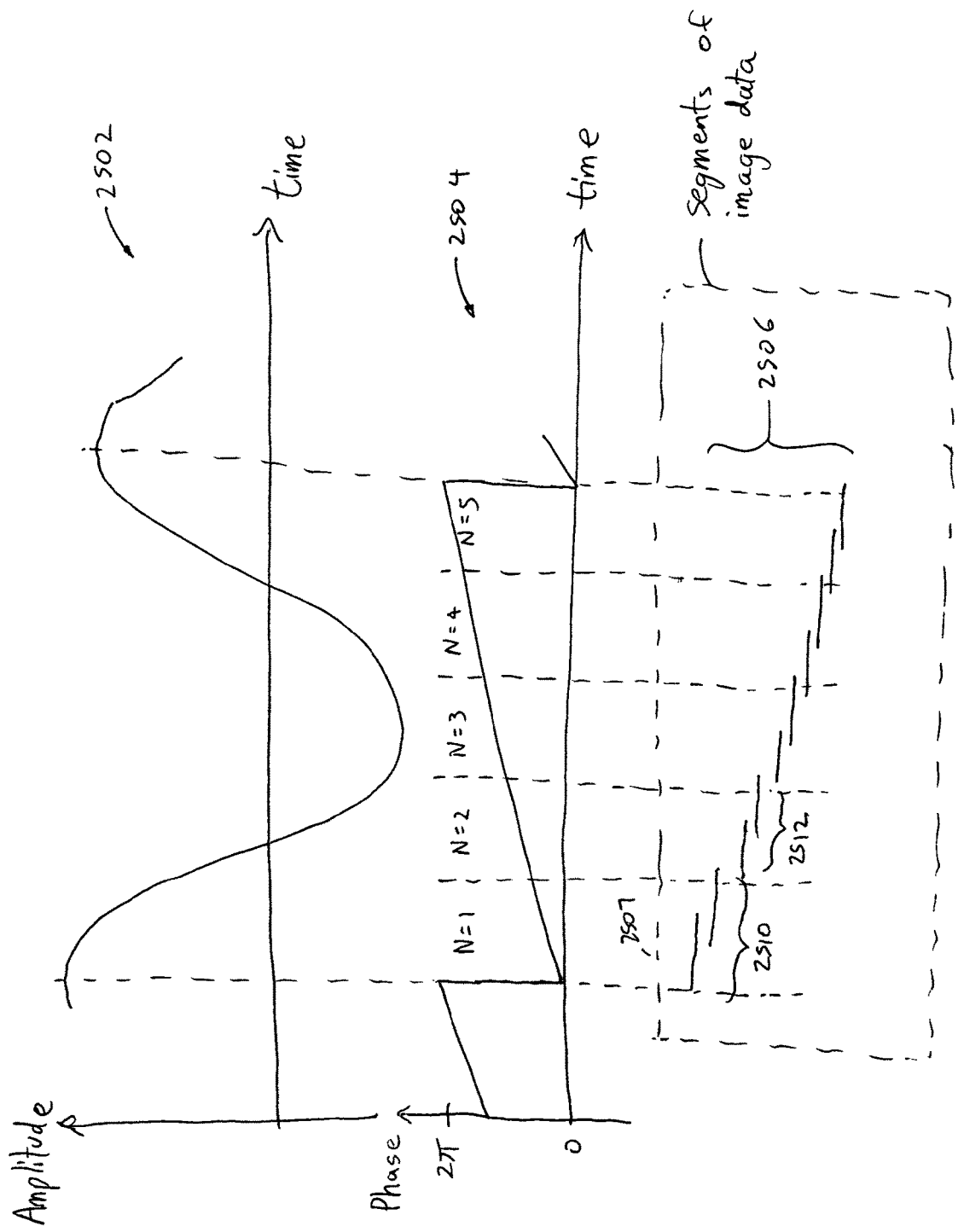
FIG. 25 shows several graphs illustrating a method of sorting image data.
Figure 26:
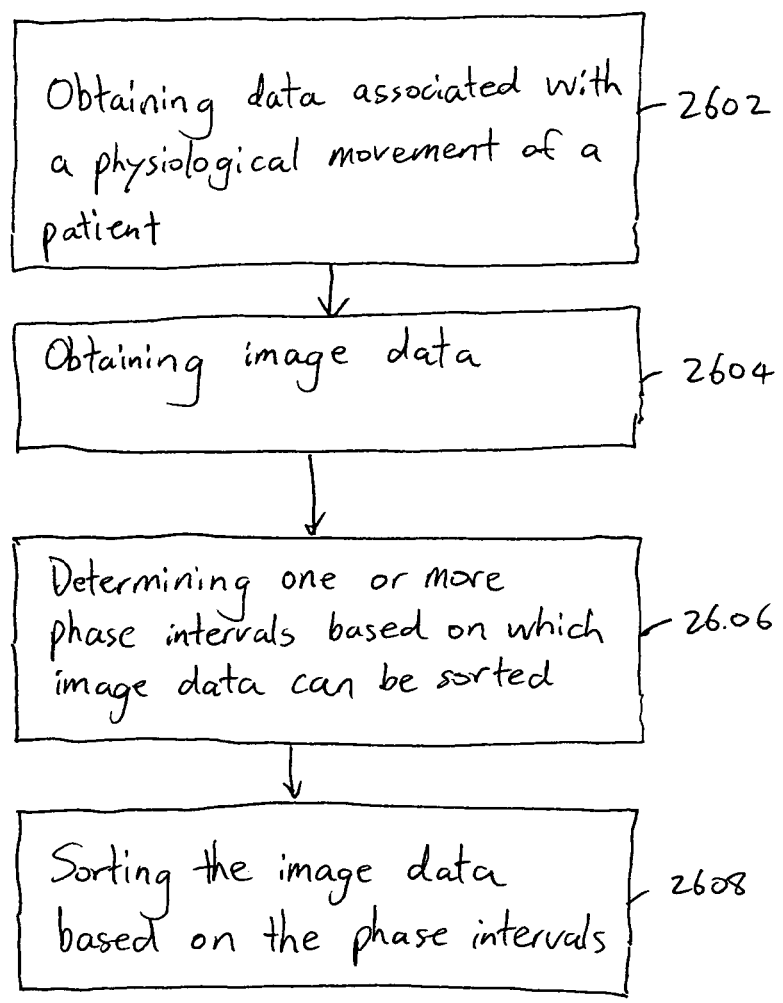
FIG. 26 is a flow chart illustrating a method of sorting image data.

A variety of methods can be used to associate image data that are generated within a phase range with each other. FIGS. 25 and 26 illustrates a process 2600 for sorting image data. After motion data and image data have been obtained (steps 2602 and 2604), a duration of a physiological movement (e.g., a portion of a physiological cycle, or a complete physiological cycle) is divided into N portions (or time bins) to define target phase intervals (step 2606). Assuming the duration of the physiological movement is 5 seconds, and N=5, then each divided portion of the duration of the physiological movement will have a 1 second duration. Next, the image data are sorted based on the prescribed target phase intervals (step 2608). Following the example, image data that are generated within the first 1 second (t=0 to 1 second) will be associated with a first phase (corresponding to N=1), image data that are generated within the second 1 second (t=1 to 2 second) will be associated with a second phase (corresponding to N=2), and so on.

FIG. 25 illustrates the above described method graphically. FIG. 25 shows a motion signal chart 2502 and a corresponding phase chart 2504 that has been divided into N=5 portions or time bins. A first set 2506 of image data generated at one table position (i.e., at one position along an axis of gantry rotation) is synchronized with the motion data to a common time base. One or more image data is represented by a bar 2507 having a length that represents an image acquisition period. Various criteria can be used to sort image data. In the illustrated embodiment, if a midpoint of a bar 2507 falls within a phase range, then the corresponding image data is associated with the phase range. Such arrangement provides a time tolerance of half an image acquisition time based on which the image data can be grouped or binned. Based on such criteria, a first group 2510 of image data are associated with a first target phase interval (N=1), and a second group 2512 of image data are associated with a second target phase interval (N=2), and so on. In some embodiments, the gantry of the CT machine can make additional revolution(s) to obtain additional image data. In such cases, the second set of image data can also be sorted using the above described method. After image data have been sorted, image data associated with the same phase range are then used to construct a volumetric image. The same process is repeated until a set of volumetric images (each of which being associated with a phase range) are created. After the volumetric images are constructed, at least portions of the volumetric images can then be displayed in a sequence to form a video.

It should be noted that although the target phase ranges are prescribed over one physiological cycle in the previously described embodiment, alternatively, target phase ranges can be prescribed over less than one physiological cycle or more than one physiological cycle. In one embodiment, target phase ranges are prescribed over one physiological cycle plus 1 second. Also, instead of using half of the image acquisition period as a time tolerance for image data binning, other time tolerance can also be used. In alternative embodiments, instead of using time tolerance, each image data is assigned an image phase value, and if the image phase value is within a prescribed threshold value from a boundary of a target phase range, then the image data is grouped or binned in that target phase range. In one embodiment, an image phase value for an image data can be calculated by obtaining an average phase values over an image acquisition period for that image data.

In another example, each target phase interval can be assigned a phase number X=Round (P/dP'), where dP'=$2\pi$/(Round ($2\pi$/dP)). $P_n$ (n=1, 2, ... N) is the average phase value (i.e., the average of the phase values obtained from a motion signal chart) for each time bin. dP=(dP$_1$+dP$_2$+ ... dP$_{N-1}$)/(N-1), where dP$_1$=P$_{n=2}$-P$_{n=1}$, and dP$_2$=P$_{n=3}$-P$_{n=2}$, and so on. Since each image data is associated with a target phase that has a phase number, each image data is also associated with the same phase number. In such case, all image data having the same phase number can be grouped to form a series. The volumetric images created from the series can be identified with the phase number, thereby allowing sequencing of the volumetric images for motion characterization.

It should be noted that although the previously described embodiments have been described with reference to processing image data that are generated by the CT gantry at one position along a Z-axis (i.e., axis of rotation of the gantry), the scope of the invention should not be so limited. In alternative embodiments, the gantry of the CT machine can move along the Z-axis, either incrementally or in a spiral arrangement, to generate image data for different portions of the patient. In such cases, the image data can be sorted to group image data that are generated at a prescribed position (or range or positions) along the Z-axis. For each set of image data that are associated with the prescribed position or range of positions, the above described process (or similar process) can be used to sort the image data such that image data associated with a prescribed phase range are grouped together or associated with each other. Also, instead of dividing a duration of physiological movement into N portions having equal durations, in alternative embodiments, the duration of physiological movement can be divided into a number of portions that have different durations (as in the case for PET).

In addition, in alternative embodiments, the above described method for retrospective gating can also include the step of assigning a confidence number to each target phase interval or time bin. For example, any of the systems and methods described herein can be used to detect a deviation from periodicity of a physiological movement (e.g., due to coughing). In such case, the higher the degree of deviation detected within a target phase interval, the lower the confidence number is assigned to the target phase interval. In one embodiment, the confidence number can be calculated based on a degree of match between the measured physiological movement and a reference motion data representative of a normal or expected physiological movement. In some embodiments, a patient's breathing can be regulated using any of the systems and methods described herein to increase the confidence number for one or more target phase intervals.

Although the above embodiments have been described with reference to CT, it should be noted that the scope of the invention should not be so limited. In alternative embodiments, similar methods can be carried out using a MRI machine or a PET machine. In addition, instead of obtaining image data and motion data of a patient, image data and motion data of other objects (such a portion of an airplane, or a portion of a structural element of a building that is undergoing stress testing) can be obtained. In such cases, the above described method can be used to process the image data and motion data of the object.

Predictive Gating

One embodiment of the present invention provides a method for detecting and predictively estimating a period of a physiological activity. In effect, the present invention can "phase lock" to the physiological movement of the patient. Since the gating system phase locks to the movement period, deviations from that periodic signal can be identified and appropriately addressed. For example, when gating to the respiratory cycle, sudden movement or coughing by the patient can result in deviation from the detected period of the respiration cycle. If the invention is employed in a radiation therapy system, radiation treatment can be gated during these deviations from the regular period. Identifying these deviations from periodicity can also be used to gate other types of medical procedures, such as imaging application. The present invention also provides a method for predictively estimating the period of the subsequent physiological movement to follow.

Figure 5:
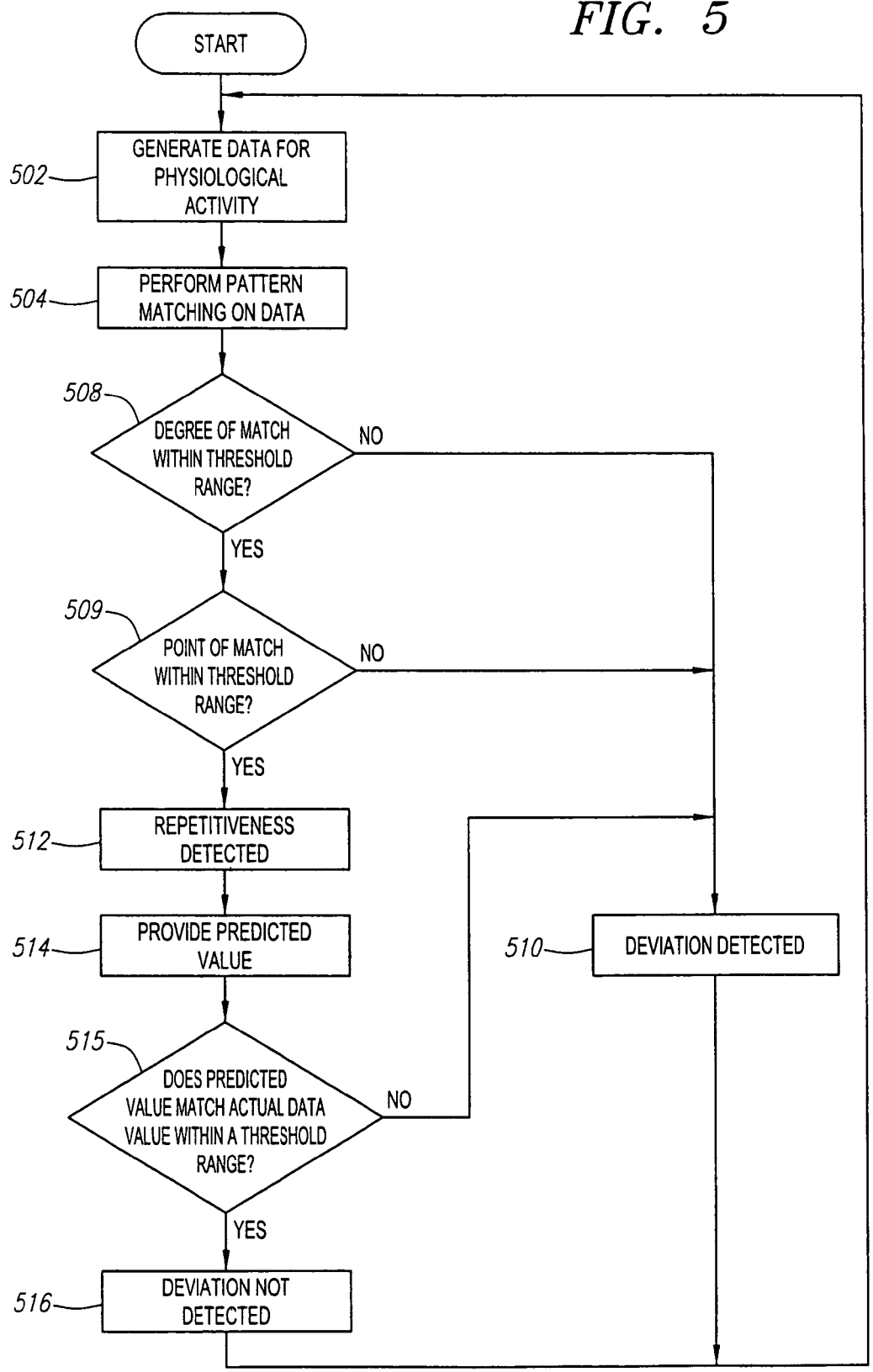
FIG. 5 is a flowchart showing process actions for detecting and predicting regular physiological movements.

FIG. 5 is a process flowchart of an embodiment of the invention to perform predictive estimation and detection of regular physiological movement cycles. In process action 502, an instrument or system (such as system 100 from FIG. 1) is employed to generate data signals representative of the physiological activity of interest. In an embodiment, the data signals comprises a stream of digital data samples that collectively form a signal wave pattern representative of the physiological movement under examination. A number of discrete measurement samples are taken for the physiological activity during a given time period. For example, in an embodiment of the invention directed towards respiratory measurement, approximately 200-210 data samples are measured for each approximately 7 second time interval.

In process action 504, pattern matching analysis is performed against the measured data samples. In an embodiment, the most recent set of data samples for the physiological signal is correlated against an immediately preceding set of data samples to determine the period and repetitiveness of the signal. An autocorrelation function can be employed to perform this pattern matching. For each new sample point of the physiological motion or physiological monitoring sensor signal, the process computes the autocorrelation function of the last n samples of the signal, where n corresponds to approximately 1.5 to 2 signal breathing periods. The secondary peak of the autocorrelation function is then identified to determine the period and repetitiveness of the signal.

In an alternate embodiment, an absolute difference function is used instead of an autocorrelation function. Instead of secondary peak, a secondary minimum in the absolute difference is searched for. For each new sample point of the physiological motion or physiological monitoring sensor signal, the process computes the minimum absolute difference between the two sets of data over a range of overlapping data samples. The secondary minimum corresponds to the data position that best matches the recent set of data samples with the preceding set of data samples.

Yet another alternate embodiment performs a pattern matching based upon a model of the physiological activity being measured. The model is a dynamic representation of the physiological motion or physiological monitoring sensor signal for that physiological activity. The latest set of data samples is matched against the model to estimate parameters of the repetitive process.

Pattern matching using the measured physiological signal (504) provides information regarding the degree of match, as well as a location of best match for the repetitive process. If an autocorrelation function is employed in process action 504, then the relative strength of secondary peak provides a measure of how repetitive the signal is. A threshold range value is defined to provide indication of the degree of match between the two sets of data samples. If the strength of the secondary peak is within the defined threshold range (process action 508), then the degree of match indicates that the signal is repetitive, and the secondary peak location provides an estimate of the signal period. If an absolute difference function is used in process action 504, then the relative value of the secondary minimum provides a measure of how repetitive the signal is. If the value of the secondary minimum meets a defined threshold range (508), then the degree of match indicates that the signal is repetitive, and the secondary minimum location provides an estimate of the signal period.

If the correlation value of the secondary peak or secondary minimum does not meet the defined threshold range, then a deviation from the regular physiological activity is detected, thereby indicating an irregularity in the regular physiological movement of the patient (510). This irregularity could result, for example, from sudden movement or coughing of the patient. In an embodiment, this detected irregularity results in the generation of a "beam hold" signal that suspends the application of radiation at the patient.

If the degree of match indicates repetitiveness, the point of best match is tested to determine if the period is within a reasonable range. The location of the secondary peak or secondary minimum provides an estimate of the period of the physiological activity. In an embodiment, the point of best match is compared to a threshold range (509). If the point of best match does not fall within the threshold range, than a deviation from regular physiological activity is detected (510). If the point of best match falls within the threshold range, then the signal is accepted as being repetitive (512).

The estimate of the period based on the point of best match can be used to predict the period and waveform parameters of the next set of data samples for the signal (514). Note that process actions 504, 508, and 509 test for repetitiveness based upon a plurality of data samples over a range of such samples. However, in some circumstances, a significant deviation from normal physiological movement may actually occur within the new or most recent data sample(s) being analyzed, but because the overall set of data samples indicates repetitiveness (e.g., because of averaging of absolute differences over the range of data samples being compared), process actions 504, 508, and 509 may not detect the deviation. To perform a test for rapid deviation, the predicted value from process action 514 is compared with the next corresponding data sample (515). If the predicted value does not match the actual data sample value within a defined threshold range, then deviation is detected (510). If a comparison of the predicted and actual data sample values fall within the defined threshold range, then repetitiveness is confirmed, and deviation is not detected for that data sample range (516).

In an embodiment, the first time the process of FIG. 5 is performed, the pattern matching process action (504) is performed over the entire range of data samples. Thereafter, the pattern matching process action can be performed over a limited search interval, which is defined by the results of the prior immediate execution of the process. For example, the predicted value from process action 514 can be used to define the location of the search interval for the next set of data samples. However, if process action 508, 509, and 514 detect deviation based upon analysis of the initial search interval, then the search interval can be expanded to ensure that a deviation has actually occurred. The process of FIG. 5 can be repeated with the increased search interval to attempt to find a point of best match outside of the initial search interval. In an embodiment, this increased search interval comprises the entire range of data samples. Alternatively, the increased search interval comprises only an expanded portion of the entire range of data samples.

According to an embodiment of the invention, physiological gating can be performed based upon the phase of the physiological activity, rather than its amplitude. This is in contrast to the example shown in FIG. 3, in which the amplitude of the physiological movement signal defines the boundaries of the treatment intervals for the application of radiation.

Figure 9:
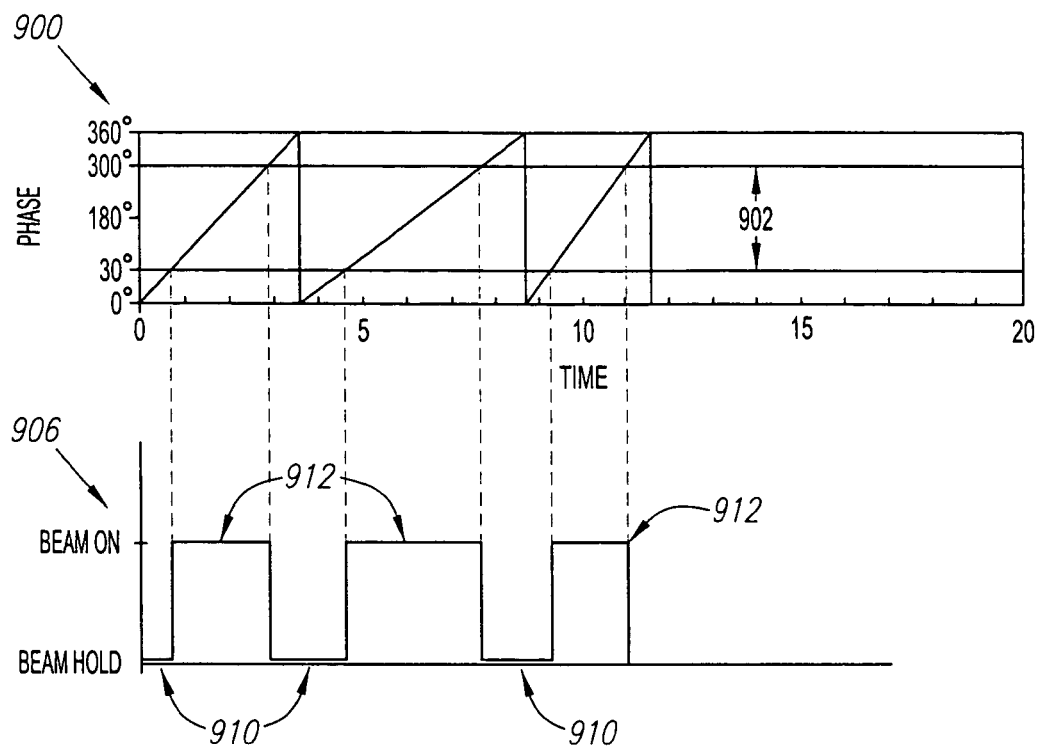
FIG. 9 depicts a phase chart synchronized with a gating signal chart.

Referring to FIG. 9, depicted is an example of a chart 900 showing the phase progression of a physiological movement signal. Treatment interval range 902 has been defined over the phase chart 900. In the example of FIG. 9, the boundaries of the treatment interval range 902 are defined by the phase of the detected signal. Radiation is applied to the patient only when the phase of the physiological movement signal falls within the boundaries of the treatment interval range 902. FIG. 9 depicts examples of treatment interval range 902 having boundaries that span from 30 degrees to 300 degrees. Thus, the applied radiation to the patient is suspended or stopped when the phase of the physiological movement signal is between 301 degrees to 29 degrees.

Shown in FIG. 9 is a gating signal chart 906 that is aligned with phase chart 900. A "beam hold" signal threshold 910 results if the phase of the physiological movement signal falls outside the treatment range 902. A "beam on" signal threshold 912 results if the phase of the physiological movement signal falls within the boundaries of the treatment interval range 902. The "beam on" and "beam hold" signal thresholds 910 and 912 are applied to a switch 116 that operatively controls the operation of a radiation beam source 102 (FIG. 1). If radiation is being applied to the patient, application of the "beam hold" signal threshold 910 triggers switch 116 to suspend or stop the application of radiation. If radiation to the patient is not being applied, application of the "beam on" signal threshold 912 triggers the application of radiation to the patient.

The predictive qualities of the present invention permits operation of a gating system even if the measured physiological movement involves motion that that is relatively fast when compared to the effectively operating speeds of gating system components. As just one example, consider a gating system that includes a switch for gating the radiation treatment, in which the switch requires a known time period $\Delta t$ to fully engage. If the switching time period $\Delta t$ is relatively slow compared to the measured physiological motion cycle, then a system employing such a switch in a reactive manner may not be able to effectively gate the application of radiation at the patient.

The present invention allows predictive triggering of switch 116 to compensate for the amount of time $\Delta t$ required to fully engage the switch. A predicted period for a physiological activity can be obtained by employing the process of FIG. 5. A treatment interval range is defined over a portion of the period of the physiological activity. Based upon the time $\Delta t$ required to fully actuate the switch 116, the switch 116 can be pre-actuated by this time period $\Delta t$ prior to the time of the boundary of the treatment interval, so that the time for full actuation of the switch 116 coincides with the boundary of the treatment interval. Thus, the radiation can be effectively gated at the boundaries of the treatment interval, regardless of the operating speeds of the switch 116. The same procedure can also be employed to compensate for the operating speeds of other gating system components.

The following is an embodiment of the invention coded in the Visual Basic programming language. The following program code is directed to a process for detecting and predictively estimating the respiration cycle period using the absolute difference function:

```
Public Function Predict(ByVal i As Long, ByVal Range As Long, Period
As Double, MinAbsDiff As Double, Diff As Double) As Double
Dim j As Long, StartJ As Long, CurrJ As Long
Dim k As Long, MaxK As Long
Dim AbsDiff As Double
Dim NormAbsDiff As Double, n As Long
k = Period − Range
MinAbsDiff= 10000000#
StartJ = TimeRefldxBuf((i− 201 + BufLength) Mod BufLength)
CurrJ = TimeRefldxBuf((i − 1 + BufLength) Mod BufLength)
Do
    j = StartJ
    AbsDiff= 0#
    n = 0
    Do
        AbsDiff= AbsDiff + Abs(SigBuf(SigRefldxBuf(j))−
        SigBuf(SigRefldxBuf((j + k + ChartWidth) Mod ChartWidth)))
        n = n + 1
        j = (j + 10) Mod Chart Width
    Loop While n <= (200 − k) I 10
    NormAbsDiff= 100 * AbsDiff I (n * Abs(MaxSignal− MinSignal))
    If NormAbsDiff <= MinAbsDiff Then
        MinAbsDiff = NormAbsDiff
        MaxK = k
    End If
    k = k+1
```

```
Loop While k <= Period + Range
If MaxK >= 40 And MaxK <= 150 Then Period = MaxK
Predict = SigBuf(SigRefIdxBuf((CurrJ - Period + Chart Width) Mod
Chart Width))
Diff= 100 * Abs(SigBuf(SigRefIdxBuf(CurrJ))- Predict) I
Abs(MaxSignal- MinSignal)
If MinAbsDiff <= 20 Then
        ProgressBar1.Value = MinAbsDiff
Else
        ProgressBar1 .Value = 20
        End If
        End Function
```

In this program code, the variable "i" represents a counter or index to the data sample being processed. The variable "Range" represents the search range that is to be analyzed. If the period of the physiological cycle has already been determined (i.e., from a prior execution of this program code), then the variable "Period" comprises the detected period. If the period has not yet been determined, then the variable "Period" is set to a default value representative of a normal respiration cycle (e.g., the number of data points in a normal breathing cycle, which is approximately 95 data samples in an embodiment of the invention where approximately 200-210 data samples are obtained over an approximately 7 second time period). The variable "MinAbsDiff" is the minimum absolute difference value over the search range. The variable "Diff" represents a comparison between the actual value of a next data sample and the expected value of that next data sample.

The variables "j", "StartJ", and "CurrJ" are counters or indexes into the data samples being processed. The variable "k" is a counter to the search range. The variable "MaxK" represents the position in the search range having the minimum absolute difference value. The variable "AbsDiff" maintains the sum of the absolute difference values for overlapping data samples. The variable "NormaAbsDiff" is the average absolute difference value for a particular position in the search range, which is represented as a percentage value. The variable "n" is used to track the position of the data samples relative to the search range, which is represented as a percentage value. "Predict" is the predicted value that is returned by this program code.

The variable "MinAbsDiff" is initialized to a high value so that so that any subsequent absolute difference value will be smaller than the initialized value. In an embodiment, the set of data samples being processed comprises 200 data points. Thus, in this program code, the variable "StartJ" is initialized back 201 data samples. The variable "CurrJ" is initialized back one data sample. Because a circular array is being used, the "BufLength" variable is referenced during the initialization of both "StartJ" and "CurrJ".

The outer Do loop moves the current and preceding sets of data samples relative to each other. The outer Do loop is active while the variable "k" indicates that the program code is processing within the search range. In an embodiment, the search range is initially set at three positions to either side of a predicted position. The predicted position is based upon the period obtained for an immediately prior execution of the program code. If the program code has not been executed immediately prior, then a default period value is used. If an acceptable minimum absolute difference value is not found within this search range, then the search range can be expanded to, for example, 50 positions to either side of the predicted position.

The variable "j" is initialized to the "StartJ" value. The variables "AbsDiff" and "n" are also initialized prior to execution of the inner Do loop.

The inner Do loop performs the computation of the absolute difference values between the present set and prior set of data samples. The variable "AbsDiff" maintains the sum of the absolute difference of values for overlapping data samples being compared. Note that the number of data samples being analyzed to determine the absolute difference values varies based upon the position in the search range being processed. This results because different positions in the search range have different numbers of data samples that overlap with the previous set of data samples being compared. In the embodiment of this program code, the absolute difference function is computed using every $10^{th}$ signal sample point, i.e., a subsampled subtraction is used. Because a circular array is being used, the "Chartwidth" variable is referenced during the calculation of "AbsDiff".

The variables "MaxSignal" and "MinSignal" indicate a maximum and minimum range for signal values that have previously been sampled. These values can be established, for example, during a learning period for the system in which data samples are obtained for a plurality of respiratory cycles. The "NormAbsDiff" variable holds the average absolute difference value represented as a percentage value based upon the "MaxSignal" and "MinSignal" values.

If the "NormAbsDiff" value is less than or equal to a previously established "MinAbsDiff" value, then the "MinAbsDiff" variable is set to the "NormAbsDiff" value. The "MaxK" variable is set to the value of "k" if the "MinAbsDiff" value is reset. The variable "k" is then incremented, and if the "k" value is still within the search range, then the program code returns back to the beginning of the outer Do loop.

The result of this program code is a candidate minimum absolute difference value and a candidate position for the minimum absolute difference. The MaxK value is compared to pre-defined threshold values to ensure that it falls within a correct range of values for the physiological activity being processed. Thus, in an embodiment, the MaxK value is tested to make sure that it is greater than or equal to 40 and less than or equal to 150. If the mark value meets the threshold range, then the variable "Period" is set to the "MaxK" value. The variable "Predict" returns the predicted value for the next set of data samples to be processed. The variable "Diff" indicates the difference value between the current data sample value and the predicted data sample value, and is represented as a percentage to the "MaxSignal" and "MixSignal" values.

In an embodiment, an image of a progress bar can be displayed to visually indicate the periodicity of the signal samples. According to the program code, if the "MinAbsDiff" value is less than or equal to a 20% difference, then the visual progress bar is updated with the computed "MinAbsDiff" value. Otherwise, the visual progress bar displays all other "MinAbsDiff" values that exceed a 20% difference as a default value of "20".

Figure 13A:
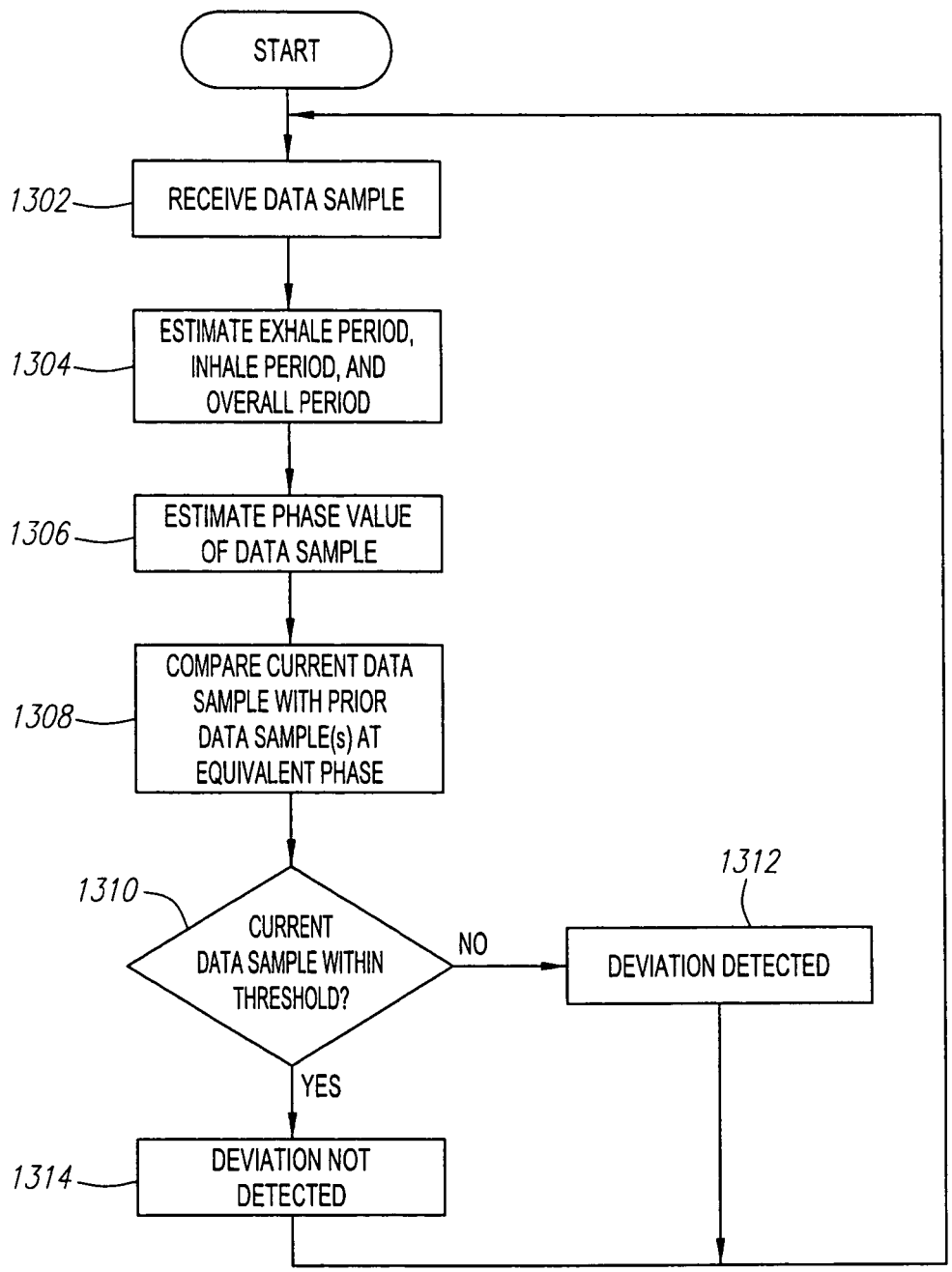
FIG. 13a shows a flowchart of a process for detecting periodicity or lack of periodicity according to an embodiment of the invention.
Figure 13B:
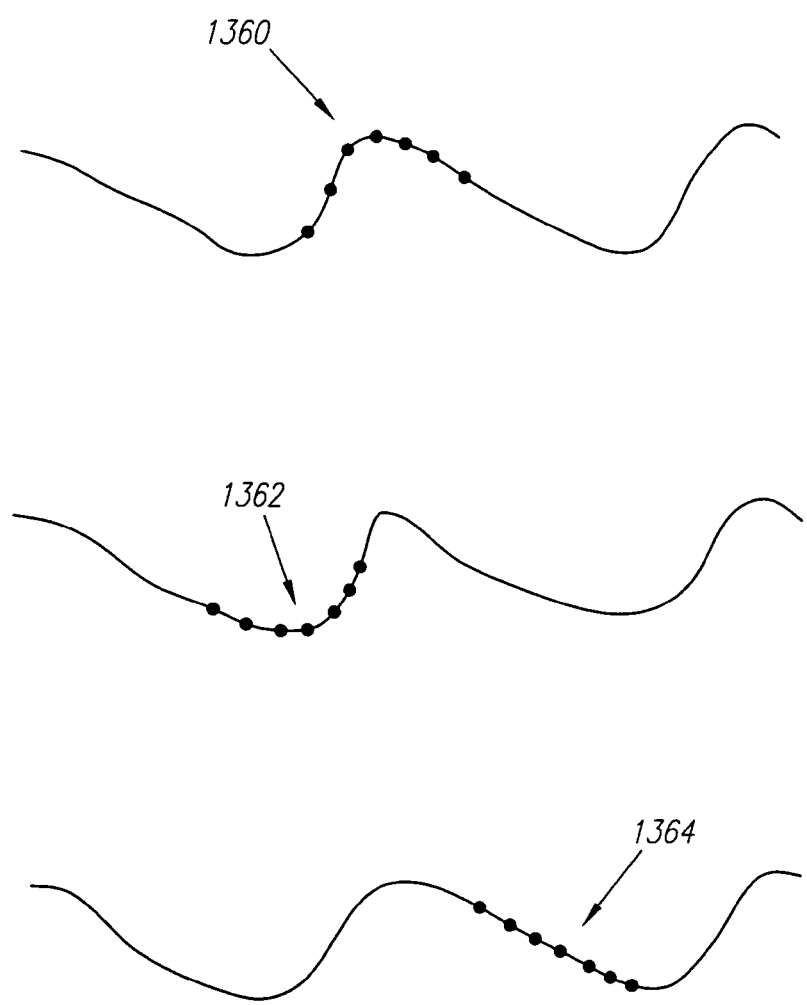
FIG. 13b illustrates sample trains according to an embodiment of the invention.
Figure 13C:
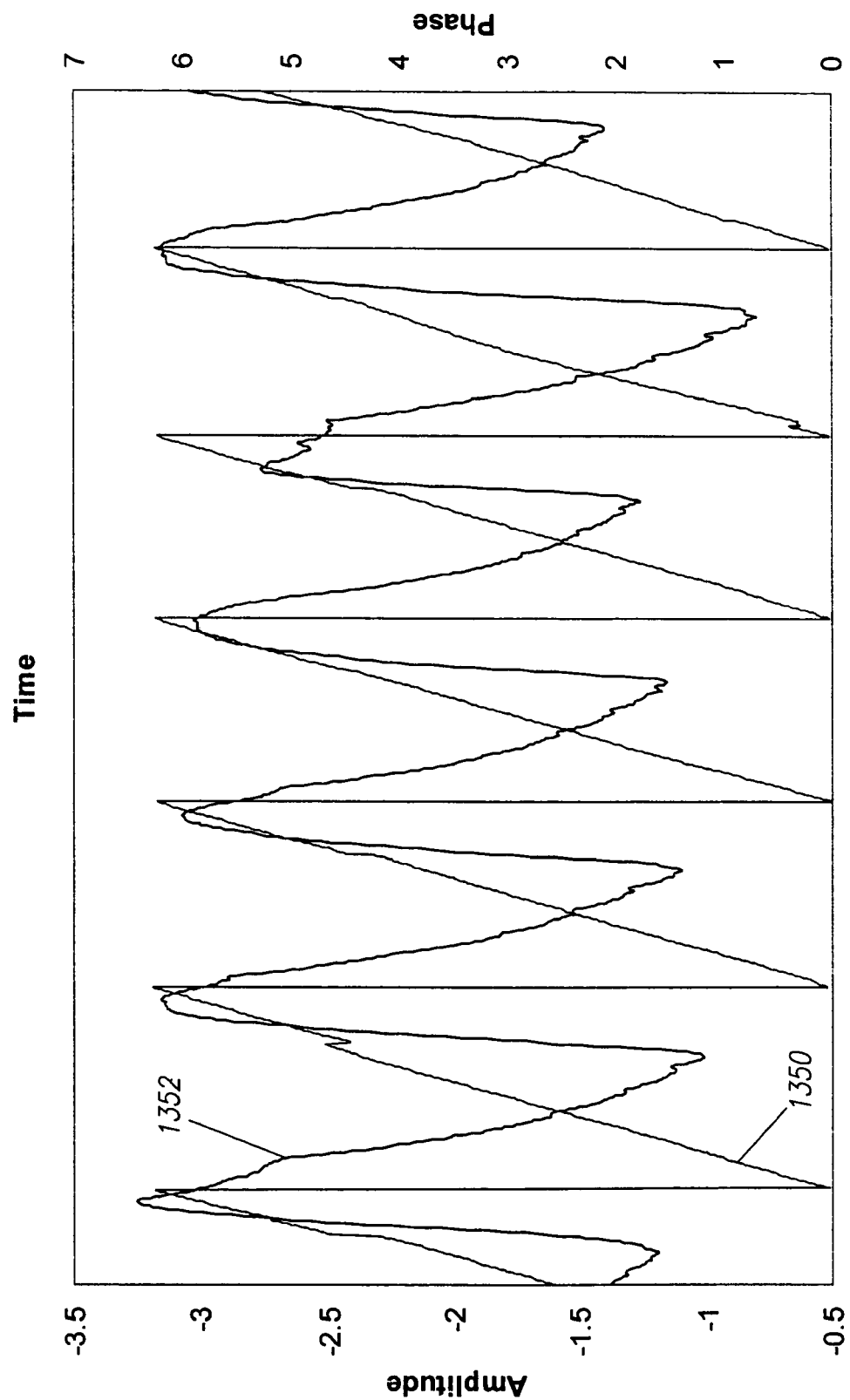
FIG. 13c is an example chart of showing phase and amplitude for a periodic signal.

FIG. 13a shows a flowchart of an alternative approach for detecting deviation from periodicity of a physiological activity. For the purposes of illustration only, and not to limit the scope of the invention, the present explanation is made with respect to the periodicity of respiration activity. This process tracks the phase of a periodic signal, and for each breathing signal sample, this approach provides an estimate of phase value indicating the breathing cycle phase for the patient. In the embodiment described here, the phase angles ranges from 0 to $2\pi$ (0 to 360 degrees) with 0 and $\pi$ corresponding to the vicinity of inhale extreme of the respiration signal. FIG. 13c shows an example phase value chart 1350 for breathing signal samples superimposed on an example respiration amplitude signal 1352.

The process of FIG. 13a receives a respiration data sample at step 1302. For each new sample of the respiration signal, the process obtains and updates estimates of the latest inhale and latest exhale extreme values and corresponding time points of the respiration signal. These values are used to establish the latest estimates of exhale period, inhale period, and therefore T, the overall period of breathing (1304).

At step 1306, the process estimates the phase value of the newly acquired respiration signal sample. In an embodiment, this is performed by computing the inner product of a Cosine waveform with period T (estimated at step 1304) and the most recent T-seconds-long segment of the signal. This is repeated by computing the inner product with a Sine waveform of period T. These two inner products are called, respectively, the in-phase and quadrature components of the signal. The inverse Tangent of the result of dividing the quadrature value by the in-phase value provides the estimated phase for the current respiration signal sample.

Figure 13D:
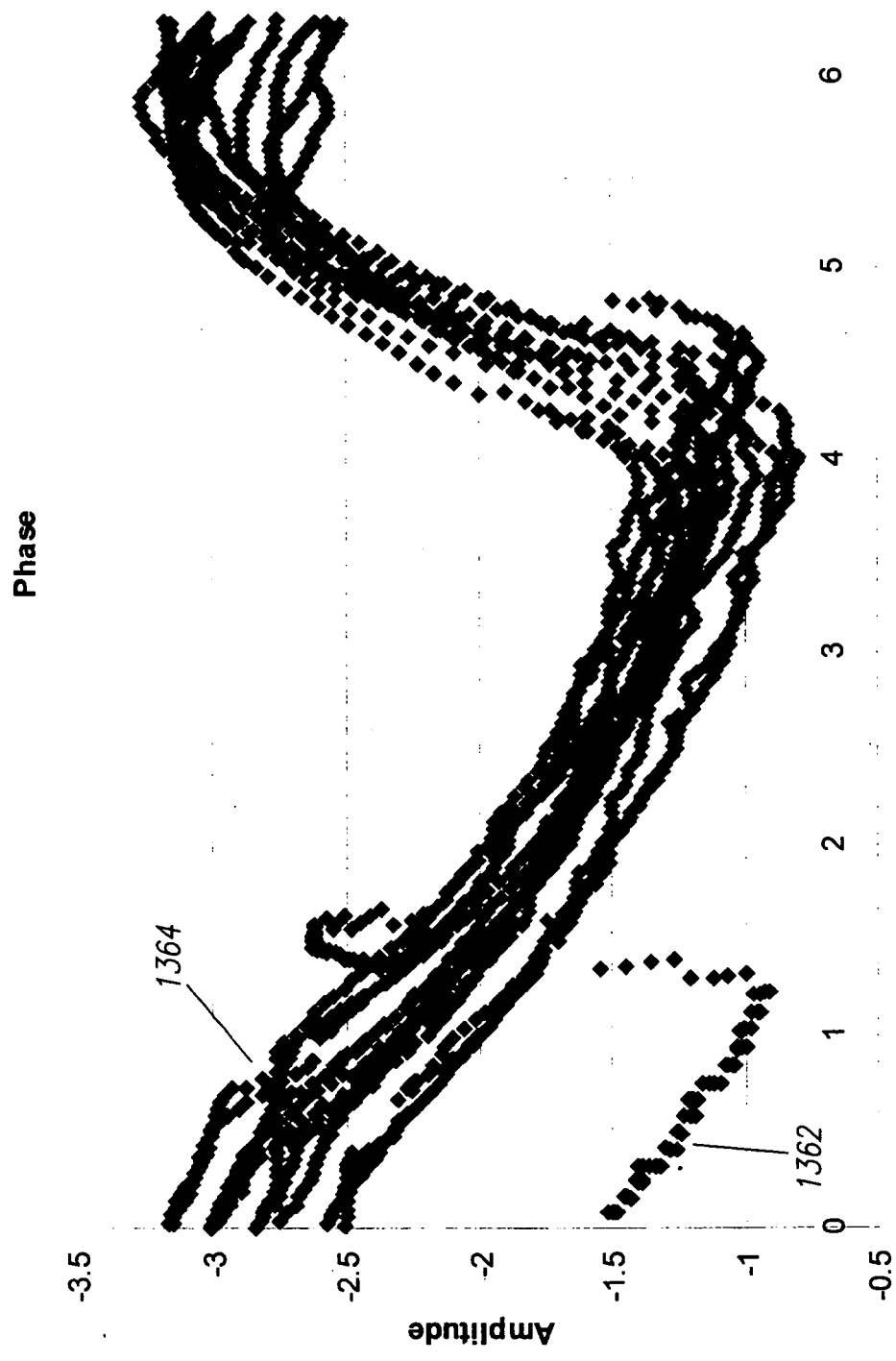
FIG. 13d shows an example of a periodic signal amplitude-phase histogram chart.

At step 1308, the process compares the vector, e.g., (amplitude, phase), of the current respiration sample with previous data sample values to determine periodicity of the signal. One approach to performing this comparison step is to use a two-dimensional histogram array of signal vs. phase value that is accumulated during prior recordings of the respiration signal. FIG. 13d shows an embodiment of a 2-dimensional histogram array 1360 of amplitude-phase values. Histogram array 1360 is a 64×64 array of bins covering the 0 to $2\pi$ phase in the horizontal dimension and the range of respiration signal amplitude in the vertical dimension. The amplitude and estimated phase of each new sample are used to increment the corresponding bin in histogram array 1360.

In an embodiment, a clustering factor determines how close the current respiration data sample vector is to the cluster of values observed so far. By comparing the amplitude-phase vector of each signal sample with the cluster of prior values in its neighborhood, the process provides a measure of periodicity for the signal. The signal is considered periodic for the current sample time when the clustering factor is above a defined threshold or tolerance level (1314). Otherwise the signal is declared non-periodic (1312). One approach is to calculate the sum of the bin populations for the 8-amplitude X 5-phase surrounding bins for the current data sample. This population, as a percentage of the total population of all histogram bins accumulated so far, determines the degree to which the new sample belongs to a periodic signal. By applying a threshold to this percentage value, the signal sample is declared as periodic or non-periodic. This threshold value can be set by the user as the sensitivity of the algorithm for detecting deviations from periodicity. In the example of FIG. 13d, data sample set 1362 would presumably be declared as non-periodic since it substantially deviates from the general body of data sample values 1364, assuming that the values in data sample set 1362 cause the determined percentage value to exceed a defined threshold.

According to an embodiment, estimation of the inhale and exhale periods pursuant to step 1304 of FIG. 13a begins by identifying a starting assumption of these periods. If the process is at its very beginning, or is recovering from a loss of periodicity, then nominal or default values (such as inhale period=1.6 Sec and exhale period=3.4 Sec) are used. The sum of these values is the current estimate of the physiological movement period. The approach of the present embodiment uses the most recent n samples of the signal to estimate the location and value of the minimum and maximum values, e.g., caused by breathing motion. One embodiment selects seven samples by sub-sampling the signal at intervals of $\frac{1}{20}^{th}$ of the period. The choice of seven samples makes the computational load of the interpolation process manageable, while sub-sampling allows coverage of a larger portion of the signal thus avoiding false detection of local minima and maxima due to noise. For every new sensed signal sample (not sub-sampled) the n samples selected as described above are first validated to make sure their corresponding interval includes a minimum or a maximum. This is performed by comparing the absolute difference of the two end samples of the sample train with the average of the difference of the center sample and the two end samples. One embodiment uses the test:

$$\mathrm{Abs}(Y(0)-Y(6))<0.2*\mathrm{Abs}(Y(0)+Y(6)-2*Y(3))$$

to determine whether the sample train includes a minimum or a maximum. In this example the train of seven samples, Y(0), Y(1), Y(2), Y(3), Y(4), Y(5), Y(6), are sub-sampled at $\frac{1}{20}^{th}$ of the of the number of samples constituting the current estimate of one period. If the result of this test is positive, curve fitting to the samples is performed. One embodiment fits a quadratic curve to the middle five points of the seven-point sample train. The location and value of the minimum or maximum value of this curve is computed using interpolation. Also at this point, it is determined whether the estimated point is a minimum or a maximum by comparing the end samples of the train with the middle sample. The estimated location of the minimum or maximum points are added to their respective accumulator variables for later averaging.

The above process is repeated with the next sensed signal sample until the procedure encounters the first sample for which the above test result is negative. This is an indication that the run of points for which a minimum or maximum can be estimated has ended. At this point the accumulator variables are divided by the number of points in the run to obtain the average location and value from the run.

The process continues by repeating the above test on the sample-train preceding every new sensed signal sample. Once the test result is positive the averaging process described above will start again. FIG. 13b shows three examples of sample trains; sample train 1360 includes a local maximum; sample train 1362 includes a local minimum; and, sample train 1364 includes neither a maximum nor a minimum.

This method estimates the local minimum or maximum location at a point in time that is later than the actual position of the extremum by the length of the sample train. The current estimate of the inhale or exhale period is updated at this point in time. For inhale period, for example, this is performed by subtracting the latest maximum position from the latest minimum position in time. These estimates are used to update the current value of the total period.

The embodiments described herein provides a tool for measuring the periodicity of the respiration signal, thus allowing detection of deviation from normal physiological movement, e.g., deviation from normal breathing caused by a patient coughing or moving. This can be used during therapy, imaging, and interventional procedures that is facilitated or require monitoring of normal patient movement. In addition, the knowledge of the phase of the physiological activity allows predictive or prospective triggering of image acquisition or the onset of radiation therapy beam in situations where these systems respond after a known delay.

Planning Phase and Interface

Figure 12A:
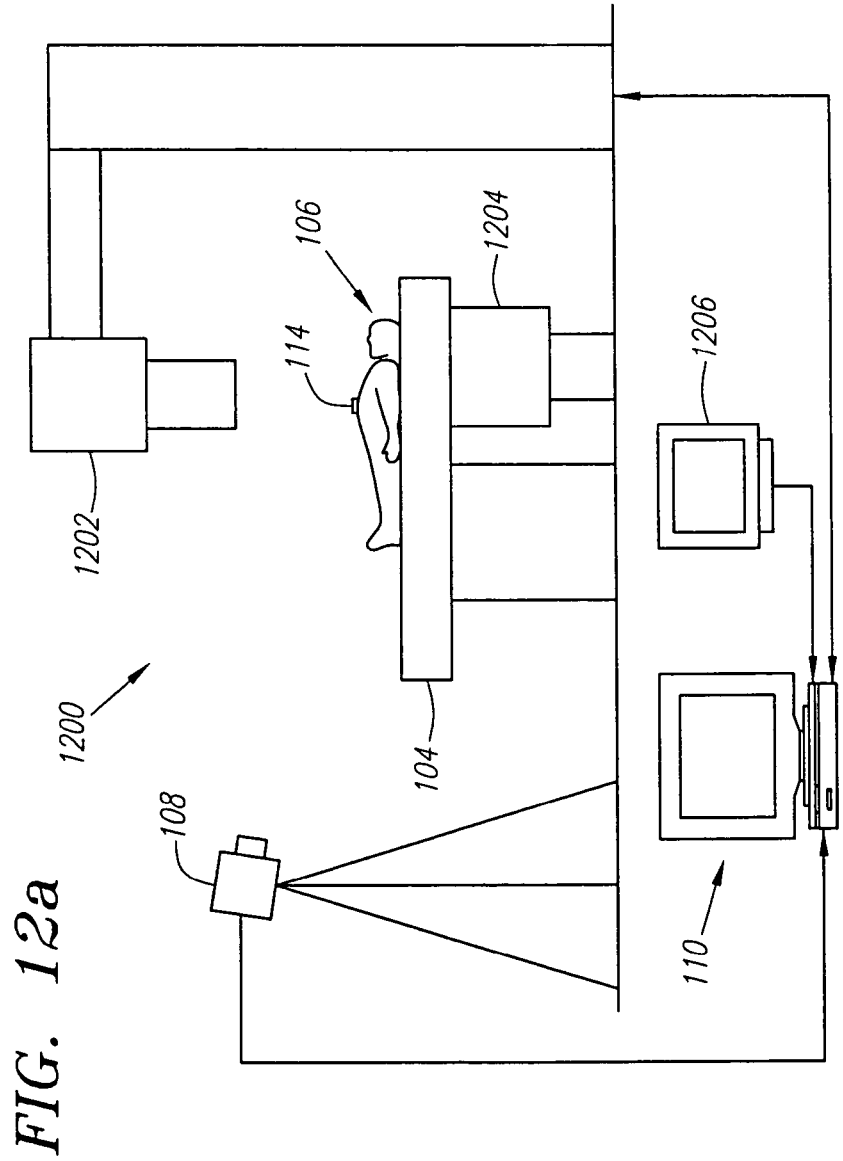
FIG. 12a depicts a system for physiological gating according to an embodiment of the invention.

During the planning phase of the radiation treatment, gating simulations can be performed to determine the optimum boundaries of the treatment intervals. FIG. 12a depicts a system 1200 that can be employed to perform gating simulation. As with the system 100 shown in FIG. 1, system 1200 comprises a camera 108 that is directed at a patient on a treatment table 104. The output signals of camera 108 are sent to a computer 110 for processing. System 1200 additionally includes an imaging system capable of generating images of internal structures within the patient's body. In an embodiment, system 1200 comprises a digital fluoroscopic imaging system having an x-ray source 1202 and fluoroscopic x-ray detection apparatus 1204. The resulting fluoro video can be displayed on a fluoro display device 1206. In addition, the output signals from the fluoroscopic x-ray detection apparatus 1204 can be sent to the computer 110.

During gating simulation, the movement of one or more landmarks or markers 114 on the patient's body is optically measured using camera 108. The detected motion of the landmark or marker 114 results in the generation of motion signals according to the process discussed with reference to FIG. 2. While motion data is being collected, the fluoroscopic video system generates imaging data for the tumor or tissue that is targeted for irradiation. The present invention records the fluoroscopic image data and the marker motion data simultaneously on a common time base. In an embodiment, the positional geometry of the fluoroscopic imaging system is configured to correspond to the projection geometry of the radiation beam source that will be used in applying radiation beams for treatment. This allows accurate simulation of the target volume to be achieved during actual treatment.

Figure 12B:
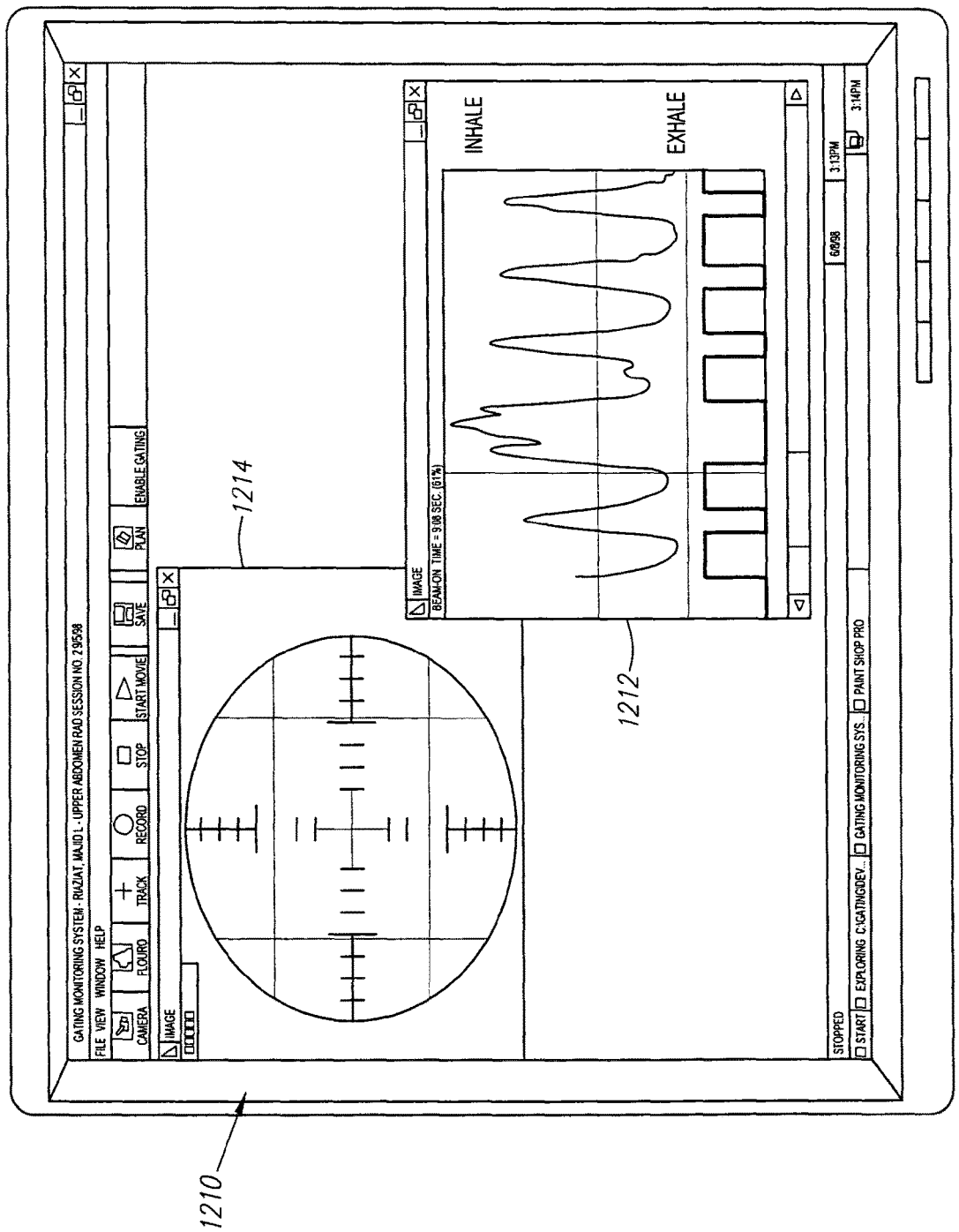
FIG. 12b illustrates an interface for viewing, controlling, and/or planning a gating plan.

FIG. 12b depicts an embodiment of a user interface 1210 for presenting the recorded data of the fluoro images and motion signals. A portion of user interface 1210 displays a chart 1212 of the measured motion signals. Another portion of user interface 1210 displays internal image data, e.g., fluoro video 1214. During the planning phase of treatment, the fluoro video 1214 of the targeted body part or location, e.g., a tumor or in cases where the tumor is not visible in fluoroscope image another anatomical landmark whose motion is highly correlated with the tumor, can be displayed in synchronization with the display of the motion signals. Simultaneous display of both sets of data allow a visual manner of determining the proper boundaries of the treatment intervals, based upon the range of movements of the targeted body part, location, tissue or tumor during particular portions of the motion signals.

Gating simulations can be effected by performing "gated playback." Gated playback involves setting simulated threshold boundaries for the treatment intervals. During the gated playback, the user interface can be configured to only display the fluoro image when the motion signal is within the boundaries of the simulated treatment intervals. The fluoro video can be turned off or frozen if the motion signal is outside the simulated treatment intervals. The gating threshold can be dynamically adjusted while both the fluoro video and the motion signals are displayed in the user interface. The playback/adjustment procedure can be performed until the physician is satisfied with the gating thresholds of the treatment window. The display rate can be dynamically adjusted to speed or slow down the visual playback of the fluoro video.

In an embodiment, a visual display border can be formed around region(s) of interest in the fluoro video 1214. For example, a box-like display border can be drawn around a tumor shown in fluoro video 1214. Alternatively, a display border generally matching the shape of a tumor can be drawn around that tumor. The visual display border can be used to simulate the shape of an applied radiation beam. During playback, the movement of the tumor in relation to the visual display border at particular points in the motion signal range can help determine the proper boundaries of the treatment intervals.

The recorded fluoro image allows digital analysis and quantification of the amount of tumor motion resulting from regular physiological movement. For each image frame, the image data corresponding to the tumor or targeted tissue can be highlighted or otherwise selected by the computer 110. Calculations can be performed upon this image data to analyze motion of the tumor or tissue during the regular physiological movements.

According to an embodiment, this analysis can be performed by edge detection and tracking. This applies to anatomic landmarks, such as the diaphragm supporting the lungs, which show an intensity edge in the fluoroscope images. The user designates an edge in a frame of the recorded fluoro segment. This could be done by drawing a line segment at or near the edge. Then, edge detection and localization is performed to determine the exact position of the edge to be found. The movie is then stepped to the next frame. In this new frame the position of the line segment corresponding to the edge location in the previous frame is used to find the edge again. This process is continued for the length of the recorded fluoro segment. The edge position, and its rate of change, is used to select the optimum treatment interval.

According to another embodiment, an area of the fluoroscope image is tracked from frame to frame using template matching. A template is selected in the first frame by drawing a box around the area of tumor or another landmark whose motion is correlated with tumor. This area under the box is used as a template that searched for in the next frame of the video segment. Since the extent of motion is limited at typical frame rates of 10 or higher frames per second, the search area for template matching will also be limited. One embodiment of template matching uses two-dimensional cross correlation in which the position of the correlation peak is used to find the position of the template in the new image frame. Another embodiment uses minimum absolute difference of the template and candidate templates in the new image. Using the absolute difference approach, the position of the minimum absolute difference will indicate the position of the template in the new frame. For both cross-correlation and minimum absolute difference embodiments, once matching template is found in the new frame, it is used as the template to be searched for in the subsequent image frame of the recoded video. The two-dimensional trajectory of the template position found in this way is then analyzed in order to determine optimum treatment intervals that correspond to least motion of specific range of positions of the tracked template.

The quantified movement data of the targeted body part, location, tumor, or tissue allows precise determination of gating thresholds for the treatment intervals. For example, if the physician desires the treatment intervals to include periods of movements that will not exceed a certain threshold movement margin, then the quantified movement data can be analyzed to determine the exact boundaries of the treatment intervals that achieves the desired movement margin. Alternatively, certain preset movement margin thresholds can be programmed into the computer 110. Based upon the preset movement margins, the system can perform an analysis of the movement data to determine the optimal gating thresholds of the treatment intervals to achieve the preset movement margins. This gating threshold can be designated as the default or suggested treatment intervals for the corresponding patient.

Verification can be performed to validate the gating threshold settings of the treatment intervals. This is particularly useful during delivery of fractionated treatment. This can be done by gated verification imaging performed during a treatment session with the radiation beam source. Gated electronic portal images can be obtained during delivery of the fractionated radiation treatments. To accomplish this, the gating system triggers a single exposure or a sequence of exposures which can be visually or automatically compared to the original reference images. The verification can be repeated at any point deemed clinically appropriate during the treatment schedule.

Patient Positioning

The position and motion monitoring system 100 can also be used to position the patient accurately in imaging and therapy applications involving multiple patient visits to a medical device, system, or room. During patient setup, the position and orientation of the marker block is recorded. By placing a marker block at the same position on the patient skin in each session, its 3-dimensional position in room or machine isocenter coordinates is an accurate representation of the patient position. At a subsequent session, the position of the patient is adjusted until the marker block is consistent with the recorded position and orientation.

Figure 18:
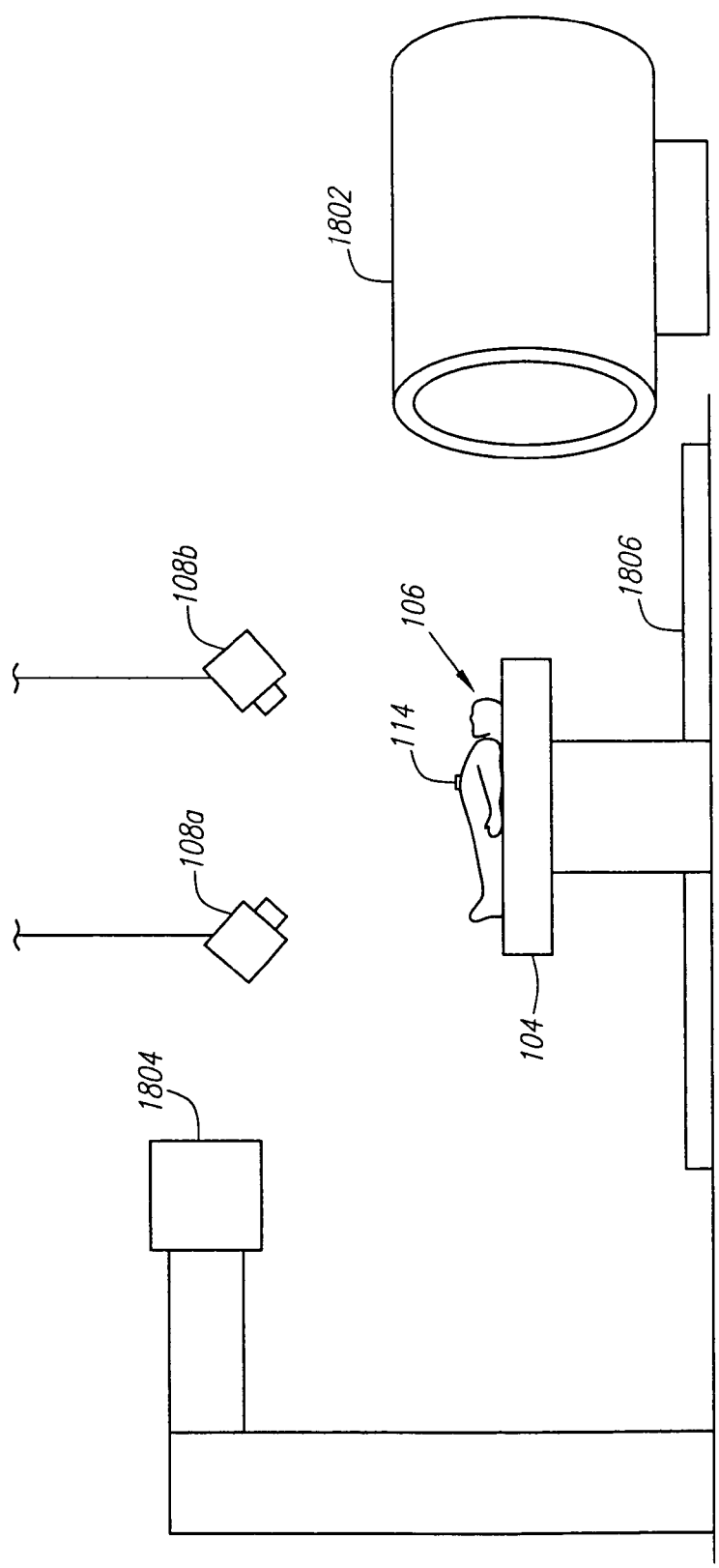
FIG. 18 shows a system for positioning a patient among multiple devices according to an embodiment of the invention.
Figure 19:
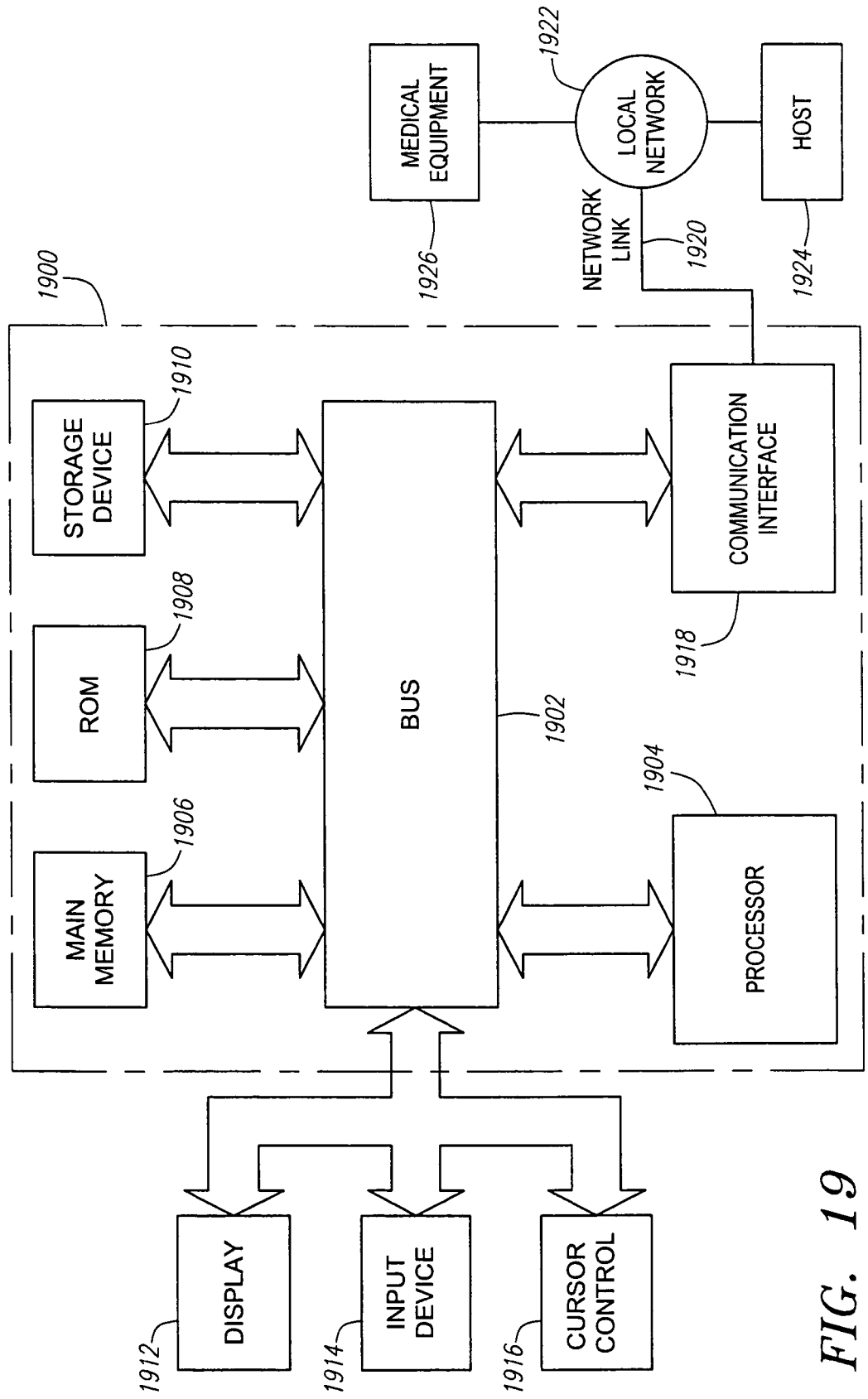
FIG. 19 is a diagram of a computer hardware system with which the present invention can be implemented.

FIG. 18 illustrates how the invention can be used to position a patient 106 among multiple medical devices. For the purposes of illustration, consider a common scenario for performing radiation therapy. A first phase of radiation therapy is a setup or treatment planning operation that consists of performing scanning or imaging procedures upon the patient to accurately locate and define the area of the patient body to be treated, e.g., using CT, MRI, SPECT, or PET procedures. The image data is used to develop a radiation treatment plan. The treatment plan often comprises the dosage level and treatment volume of radiotherapy to apply to the patient. The treatment planning phase may also comprise a simulation procedure to verify the appropriateness of the treatment plan. Once the treatment plan is developed, the second phase involves moving the patient to a radiation therapy device to implement the treatment plan. To optimize this procedure, the patient's relative position to the radiation therapy device should be consistent relative to the patient's imaging position for the image data used to develop the treatment plan.

According to an embodiment of the invention, the optical position and motion monitoring system of the present invention is usable to accurately and consistently position a patient among multiple medical devices. Shown in FIG. 18 is a patient 106 co-located with a marker block 114. During setup operations, the patient is scanned or imaged using an imaging device, such as MRI device 1802 or a CT system. During patient setup, a first video camera 108a provides images of the patient to record the position and orientation of the marker block 114. The 3-dimensional position or machine isocenter coordinates of the marker block 114 for the imaging session at the MRI device 1802 is stored as reference data.

During the subsequent treatment session, the patient 106 is moved to a radiation therapy device 1804. In an embodiment, the treatment table 104 upon which the patient 106 is resting is configured such that it can be moved between the MRI device 1802 and the radiation therapy device 1804. This can be accomplished, for example, by movably attaching the treatment table 104 to floor rails 1806. Moving the entire treatment table 104 to move the patient 106 between medical devices, rather than moving just the patient 106, reduces the chance that internal organs within the patient will shift during movement.

Because the geometry of the first camera 108a to the MRI device 1802 is known, and the geometry of the second video camera 108b to the radiation therapy device 1804 is also known, it is possible to translate the relative position of the patient during the imaging session before the MRI device 1802 into a corresponding relative position at the radiation therapy device 1804. This corresponding relative position is the desired position at the radiation therapy device 1804 to maximize the efficacy of the treatment plan developed based upon imaging geometry at the MRI device 1802.

When the treatment table 104 is moved to the radiation therapy device 1804, a second video camera 108b provides images of the patient 106 that is used to calculate the 3-dimensional position or machine isocenter coordinates of the marker block 114. Because the desired patient/marker block location is known, the patient 106 or treatment table 104 can be shifted until the marker block is consistent with desired position and orientation.

Figure 16:
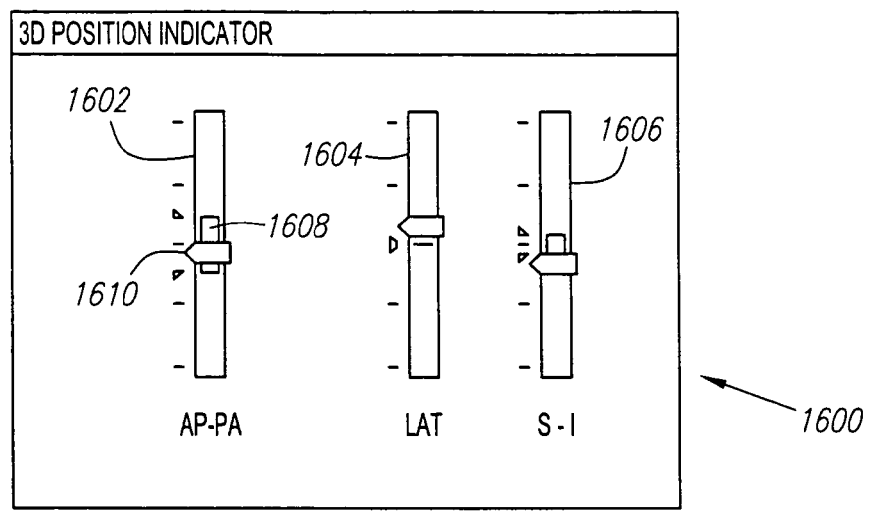
FIGS. 16 and 17 show embodiments of slider interfaces according to embodiments of the invention.

During patient positioning, the therapist can monitor patient position in real time using indicators such as the slider interface 1600 shown in FIG. 16. Each slider in interface 1600 shows position in a specific dimension relative to the reference session. The slider element 1610 in slider 1602 tracks motion of the patient in the anterior/posterior-posterior/anterior dimension. Slider 1604 tracks the lateral movement of the patient. Slider 1606 tracks the Superior-Inferior movement of the patient. The exact positions of slider elements in interface 1600 are recorded during patient setup. To perform patient positioning, the position of the patient is adjusted until the slider bars are consistent with the measured positions of the slider elements from the setup phase. When a patient is surveyed during setup, the slider positions representing the patient coordinates are recorded. Each slider can be configured to show the expected range of respiration motion as a reference interval, which is shown in interface 1600 as a black bar within each slider 1602, 1604, and 1606. For example, black bar 1608 shows the normal expected range of motion for the slider element 1610 in slider 1602

Patient Feedback and Breath Hold

According to an embodiment of the invention, a real time position indicator display is provided that can also serve as patient visual feedback for both regulating and limiting the breathing motion in normal breathing mode. The position indicator display is also usable for positive cooperation by patient in breath-hold mode of imaging and interventional procedures.

Medical procedures in which a patient may be instructed to hold breath include image acquisition procedures and interventional procedures such as biopsy needle insertion. Typically, several breath holds separated by normal patient breathing are usually required to complete the image acquisition or delivery of radiation dose for therapy. In conventional breath hold applications, it is extremely difficult for a patient to maintain a consistent position from one breath hold to another breath hold. This difficulty arises because the patient cannot precisely determine the exact point to consistently hold breath from one instance to another. Thus, it is possible that the volume or position of a patient's chest/abdomen differs from one breath hold to another.

As noted above, the optical monitoring system of FIG. 1 can be used to quantify the position and orientation of a patient position corresponding to a marker block or a set of markers. Thus, the position and offset of movement by a patient during breath hold can be quantified. By quantifying these values during breath hold, the patient position during breath hold can be reliably and consistently repeated.

Figure 17:
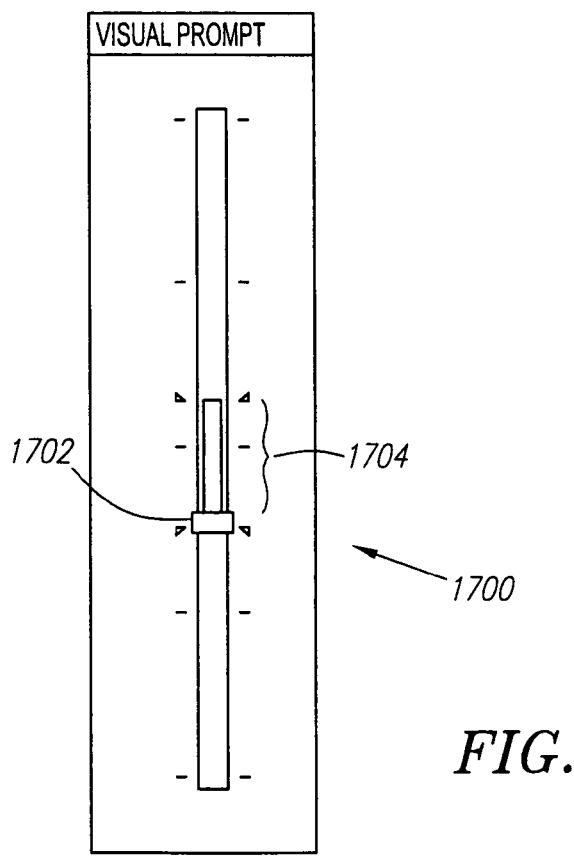

FIG. 17 shows one embodiment of a real time position indicator 1700 using a slider that is displayed to the patient on a computer display. The slider position 1702 shows, for example, the up-down chest position for a horizontal patient setup. During exhale, the slider position 1702 moves up and during inhale, the slider position 1702 moves down. The expected range of positions, e.g., for breath holding is shown as an interval 1704.

The patient is instructed to try and maintain the position of the slider bar 1702 within the boundaries of the indicated range 1704, where the position and width of this range of motion is selected according to what the patient could comfortably achieve in the planning session. In an embodiment, the visual feedback tool is also used to encourage the patient to breathe more shallowly than he or she normally would. Verbal prompting and feedback can also be provided to the patient to influence a more consistent physiological pattern. For example, an audio message "breathe in" can be performed to prompt a patient during a desired inhale period. An audio message "breathe out" can be performed to prompt a patient during a desired exhale period. An audio message "hold breath" can be performed to prompt a patient during a desired breath hold period.

The interface of FIG. 16 can also be used to graphically quantify the patient breath hold position. An indicator range can be placed in one or more of the sliders in interface 1600 at a desired breath hold position. To recreate that breath hold position, the patient is instructed to hold breath until the slider bars within the appropriate sliders correspond to the marker position on the sliders. For imaging applications, the onset of image acquisition for each breath hold is triggered when marker block position enters the range corresponding to breath-hold, and is automatically stopped when the patient relaxes and marker block exits the breath hold range. This makes the breath hold imaging mode more accurate and robust because without such position monitoring capability the patient breath hold position can change from breath-hold to breath-hold.

Interface Controls

Figure 20:
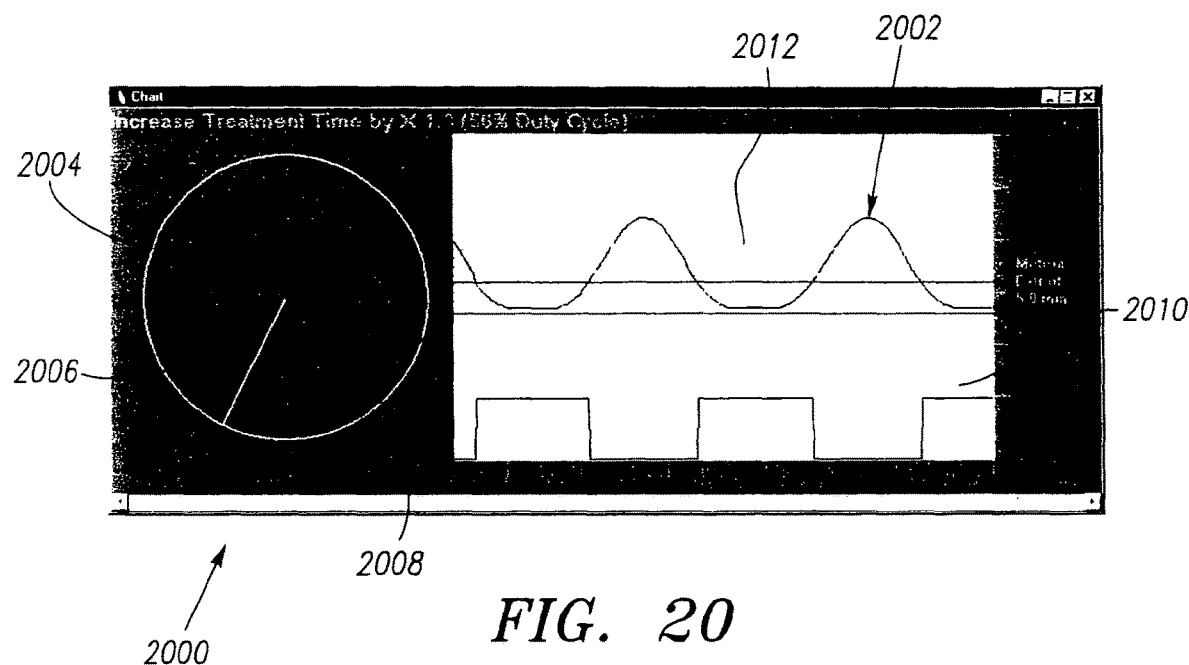
FIGS. 20-24 show interfaces for controlling, displaying, and planning according to embodiments of the invention.

FIG. 20 displays an indicator display 2000 for controlling and displaying motion and gating information. Display 2000 comprises a graphical signal chart 2002 that tracks the physiological movement of the patient, e.g., by tracking the motion of a marker block. A phase display portion 2004 includes a moving display bar 2006 that tracks the phase of the physiological movement. If gating based upon phase is employed, then the gating range or non-gating range can be controlled by defining a treatment window 2008 in the phase display portion 2004. The treatment window 2008 is defined to extend from a first phase value to a second phase value within the phase display portion 2004. Alternatively, gating can be implemented by defining treatment intervals 2010 over the amplitude signal chart 2002 of the physiological movement.

To provide visual prompting for a patient, a desired movement window 2012 is displayed over the signal chart 2002. During the exhale period, the patient is instructed to try and maintain the position of the signal chart 2002 within the lower boundaries of the indicated range for the movement window 2012. During the inhale period, the patient is instructed to try and maintain the position of the signal chart 2002 within the upper boundaries of the movement window 2012.

Figure 21:
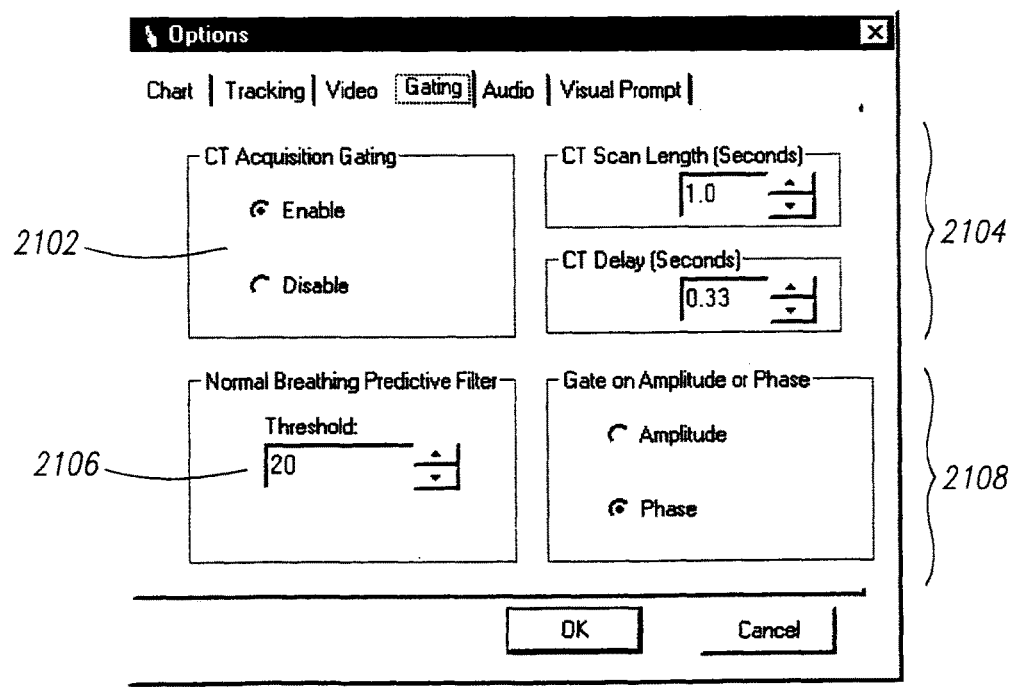

FIG. 21 shows an interface window for controlling a CT gating and monitoring system. A control portion 2102 is used to turn on or off CT gating. The control portion 2106 sets a threshold value for determining deviation from periodicity of the breathing cycle, e.g., as used for the process of FIG. 13a. The control portion 2108 determines whether gating is performed based upon either amplitude or phase. The control portion 2104 allows entry of the known or estimated CT scanner delay and scan length parameters for the CT scanners that do not have a feedback interface for automatic sensing of these parameters. These parameters are used to show the best estimate of the CT scan period on the breathing chart. In an embodiment of the invention the portion of breathing chart corresponding to the CT scan period is drawn in color green. For example in a therapy application this allows selection of gating thresholds that result in the best match of the beam-on period and the CT image acquisition interval, i.e., the user tries to match the beam-on period with the green portions of the breathing chart.

Figure 22:
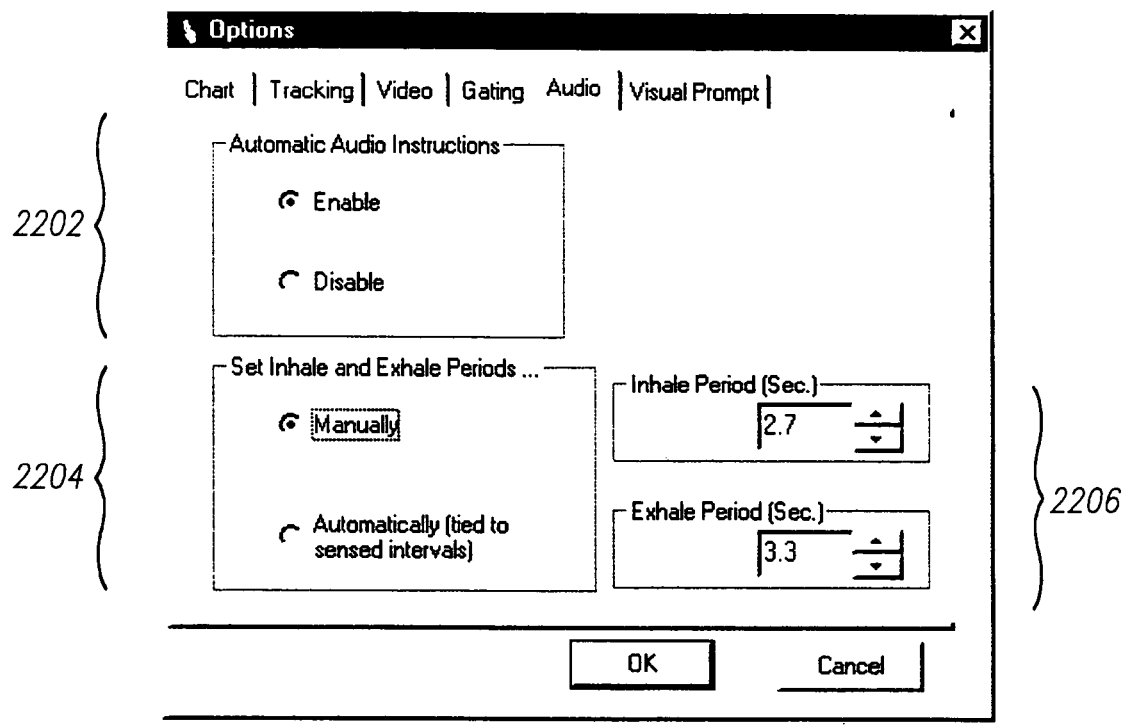

FIG. 22 shows an interface window for controlling patient prompting and feedback. Control portion 2202 determines whether audio prompting is performed to regulate the physiological movement. Control portion 2204 determines whether the inhale and exhale periods for patient feedback is manually or automatically set. If the inhale and exhale periods are manually set, then the inhale/exhale period values shown in control portion 2206 are manually configured. If the inhale and exhale periods are automatically set, then these periods are automatically determined, e.g., using the process shown in FIG. 13b. In this case the control portion 2206 is used to increment or decrement the automatically sensed inhale and exhale periods before using them to prompt the patient. This, for example, is used to encourage the patient to breathe more slowly than he or she would normally breath.

Figure 23:
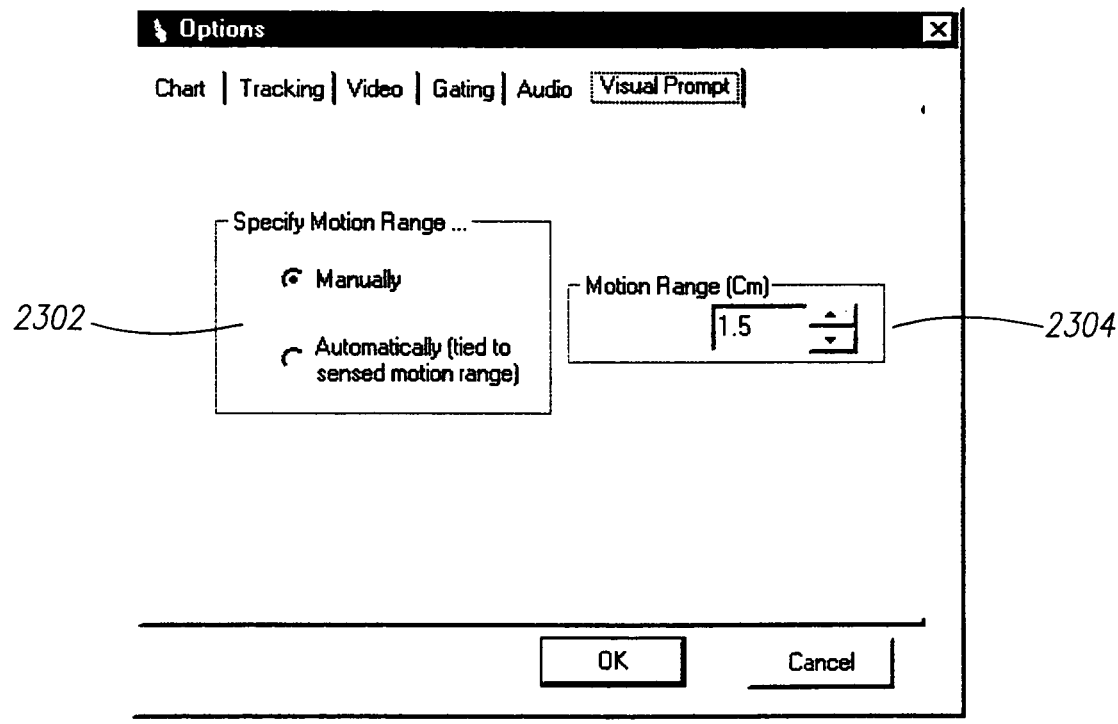

FIG. 23 shows an interface window for controlling the visual feedback used to limit the motion range for the physiological movement. A control portion 2302 determines whether the motion range is manually or automatically set. If the motion range is manually set, then the motion range value shown in control portion 2304 is manually configured. Otherwise, the control portion 2304 is automatically configured, e.g., based upon the sensed motion range for the marker block.

Figure 24:
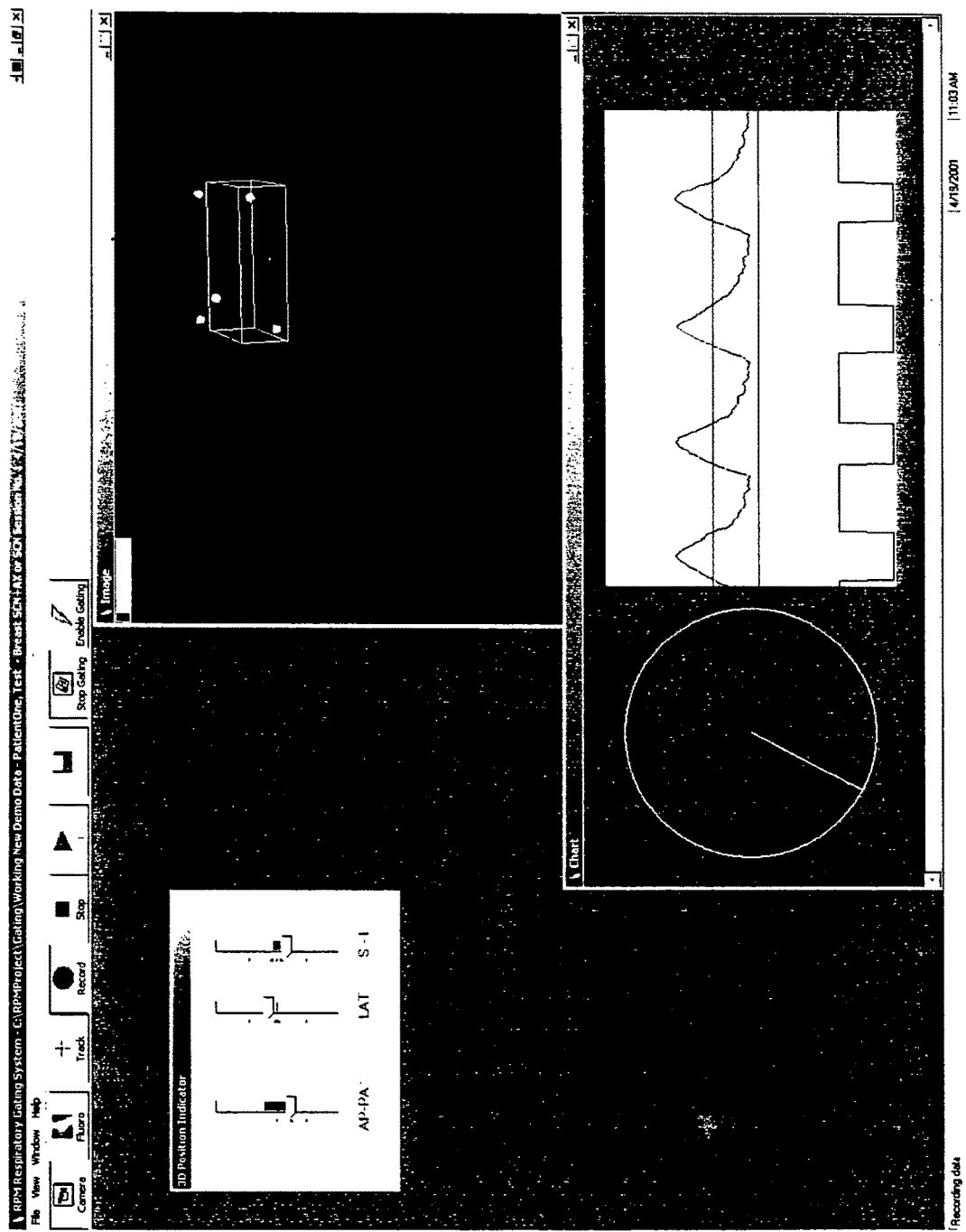

FIG. 24 shows a screenshot of a display window according to an embodiment of the invention. A first portion of the display window shows the sliders of FIG. 16 quantifying real-time motion of the marker block. A second portion of the display window shows the control interface of FIG. 20. A third portion of the display window shows a real-time image of the patient as seen through the video camera.

Computer System Architecture

FIG. 12 is a block diagram that illustrates an embodiment of a computer system 1900 upon which an embodiment of the invention may be implemented. Computer system 1900 includes a bus 1902 or other communication mechanism for communicating information, and a processor 1904 coupled with bus 1902 for processing information. Computer system 1900 also includes a main memory 1906, such as a random access memory (RAM) or other dynamic storage device, coupled to bus 1902 for storing information and instructions to be executed by processor 1904. Main memory 1906 also may be used for storing temporary variables or other intermediate information during execution of instructions to be executed by processor 1904. Computer system 1900 further includes a read only memory (ROM) 1908 or other static storage device coupled to bus 1902 for storing static information and instructions for processor 1904. A data storage device 1910, such as a magnetic disk or optical disk, is provided and coupled to bus 1902 for storing information and instructions.

Computer system 1900 may be coupled via bus 1902 to a display 1912, such as a cathode ray tube (CRT), for displaying information to a user. An input device 1914, including alphanumeric and other keys, is coupled to bus 1902 for communicating information and command selections to processor 1904. Another type of user input device is cursor control 1916, such as a mouse, a trackball, or cursor direction keys for communicating direction information and command selections to processor 1904 and for controlling cursor movement on display 1912. This input device typically has two degrees of freedom in two axes, a first axis (e.g., x) and a second axis (e.g., y), that allows the device to specify positions in a plane.

The invention is related to the use of computer system 1900 for detecting and predictively estimating physiological cycles. According to one embodiment of the invention, such use is provided by computer system 1900 in response to processor 1904 executing one or more sequences of one or more instructions contained in main memory 1906. Such instructions may be read into main memory 1906 from another computer-readable medium, such as storage device 1910. Execution of the sequences of instructions contained in main memory 1906 causes processor 1904 to perform the process steps described herein. One or more processors in a multi-processing arrangement may also be employed to execute the sequences of instructions contained in main memory 1906. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to processor 1904 for execution. Such a medium may take many forms, including but not limited to, non-volatile media, volatile media, and transmission media. Non-volatile media includes, for example, optical or magnetic disks, such as storage device 1910. Volatile media includes dynamic memory, such as main memory 1906. Transmission media includes coaxial cables, copper wire and fiber optics, including the wires that comprise bus 1902. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 1904 for execution. For example, the instructions may initially be carried on a magnetic disk of a remote computer. The remote computer can load the instructions into its dynamic memory and send the instructions over a telephone line using a modem. A modem local to computer system 1900 can receive the data on the telephone line and use an infrared transmitter to convert the data to an infrared signal. An infrared detector coupled to bus 1902 can receive the data carried in the infrared signal and place the data on bus 1902. Bus 1902 carries the data to main memory 1906, from which processor 1904 retrieves and executes the instructions. The instructions received by main memory 1906 may optionally be stored on storage device 1910 either before or after execution by processor 1904.

Computer system 1900 also includes a communication interface 1918 coupled to bus 1902. Communication interface 1918 provides a two-way data communication coupling to a network link 1920 that is connected to a local network 1922. For example, communication interface 1918 may be an integrated services digital network (ISDN) card or a modem to provide a data communication connection to a corresponding type of telephone line. As another example, communication interface 1918 may be a local area network (LAN) card to provide a data communication connection to a compatible LAN. Wireless links may also be implemented. In any such implementation, communication interface 1918 sends and receives electrical, electromagnetic or optical signals that carry data streams representing various types of information.

Network link 1920 typically provides data communication through one or more networks to other devices. For example, network link 1920 may provide a connection through local network 1922 to a host computer 1924 or to medical equipment 1926 such as a radiation beam source or a switch operatively coupled to a radiation beam source. The data streams transported over network link 1920 can comprise electrical, electromagnetic or optical signals. The signals through the various networks and the signals on network link 1920 and through communication interface 1918, which carry data to and from computer system 1900, are exemplary forms of carrier waves transporting the information. Computer system 1900 can send messages and receive data, including program code, through the network(s), network link 1920 and communication interface 1918.

In the foregoing specification, the invention has been described with reference to specific embodiments thereof. It will, however, be evident that various modifications and changes may be made thereto without departing from the broader spirit and scope of the invention. For example, the operations performed by computer 110 can be performed by any combination of hardware and software within the scope of the invention, and should not be limited to particular embodiments comprising a particular definition of "computer". The specification and drawings are, accordingly, to be regarded in an illustrative rather than restrictive sense.

The invention claimed is:

1. A method for gating an application of radiation to a patient, comprising:
   directing a camera at a patient;
   generating image data representative of a position of the patient associated with a physiological movement of the patient;
   obtaining an amplitude value and a phase value based at least in part on the image data;
   combining the amplitude value and the phase value to form a vector;
   performing an analysis using the vector; and
   gating an application of radiation to the patient based upon a result from the act of performing the analysis.

2. The method of claim 1, further comprising locating a marker block on the patient.

3. The method of claim 2, wherein the marker block comprises two or more markers.

4. The method of claim 1, wherein the gating comprises predictively actuating a gating component.

5. The method of claim 1, further comprising determining deviation from periodicity based on the result from the act of performing the analysis.

6. The method of claim 1, wherein the act of performing the analysis using the vector comprises comparing, using an electronic processing unit, the vector with a cluster of values associated with previous respiration samples.

7. The method of claim 1, wherein the act of performing the analysis using the vector comprises:
   comparing, using an electronic processing unit, the vector with a cluster of values in a histogram, the cluster of values associated with previous respiration samples; and
   determining, using the electronic processing unit, whether there is deviation from periodicity based on a result from the act of comparing.

8. The method of claim 1, wherein the radiation comprises imaging radiation.

9. The method of claim 1, wherein the act of performing the analysis comprises processing the vector with histogram values.

10. The method of claim 9, wherein the histogram values comprise a plurality of previous vectors.

11. The method of claim 10, wherein each of the previous vectors comprises a breathing amplitude value, and a breathing phase value.

12. The method of claim 1, wherein the phase value is between 0 and $2\pi$.

13. The method of claim 6, wherein the cluster of values is a part of a histogram.

14. The method of claim 6, wherein the cluster of values comprises a plurality of previous vectors.

15. The method of claim 14, wherein each of the previous vectors comprises a breathing amplitude value, and a breathing phase value.

16. The method of claim 7, wherein the cluster of values comprises a plurality of previous vectors.

17. The method of claim 16, wherein each of the previous vectors comprises a breathing amplitude value, and a breathing phase value.

18. The method of claim 1, wherein the phase value is within a range of possible phase values, and wherein the possible phase values represent respectively different extents of a breathing in a respiratory cycle.

* * * * *